(12) United States Patent
Cadoret et al.

(10) Patent No.: US 8,728,761 B2
(45) Date of Patent: May 20, 2014

(54) PRODUCTION OF GLYCOSYLATED POLYPEPTIDES IN MICRO ALGAE

(75) Inventors: Jean-Paul Cadoret, Basse Goulaine (FR); Aude Carlier, Nantes (FR); Patrice Lerouge, Grand Couronne (FR); Muriel Bardor, Isneauville (FR); Carole Burel, Bourdainville (FR); Florian Maury, Mont Saint Aignan (FR)

(73) Assignees: Institut Francais de Recherche pour l'Exploitation de la Mer (IFREMER), Issy les Moulineaux (FR); Centre National de la Recherche Scientifique—CNRS, Paris (FR); Universite de Rouen, Mont-Saint-Aignan (FR)

( * ) Notice: Subject to any disclaimer, the term of this patent is extended or adjusted under 35 U.S.C. 154(b) by 549 days.

(21) Appl. No.: 12/867,279

(22) PCT Filed: Feb. 12, 2009

(86) PCT No.: PCT/EP2009/051672
§ 371 (c)(1),
(2), (4) Date: Nov. 2, 2010

(87) PCT Pub. No.: WO2009/101160
PCT Pub. Date: Aug. 20, 2009

(65) Prior Publication Data
US 2011/0045533 A1    Feb. 24, 2011

(30) Foreign Application Priority Data
Feb. 12, 2008 (EP) ................... 08300090

(51) Int. Cl.
| | |
|---|---|
| *C12P 21/00* | (2006.01) |
| *C12P 19/18* | (2006.01) |
| *C07K 16/00* | (2006.01) |
| *A61K 39/00* | (2006.01) |
| *A01H 11/00* | (2006.01) |
| *A01H 13/00* | (2006.01) |
| *C12N 1/13* | (2006.01) |

(52) U.S. Cl.
USPC ...... 435/69.1; 435/70.21; 435/97; 435/257.2; 530/387.1; 530/388.23; 800/296; 800/278; 536/23.2; 536/23.51; 536/23.52; 536/23.1

(58) Field of Classification Search
None
See application file for complete search history.

(56) References Cited

FOREIGN PATENT DOCUMENTS

| | | |
|---|---|---|
| WO | 2006/013572 A2 | 2/2006 |
| WO | 2007/130638 A2 | 11/2007 |
| WO | 2008/096250 A1 | 8/2008 |

OTHER PUBLICATIONS

Leon-Banares, et al. Transgenic microalgae as green cell-factories. (2004) Trends in Biotechnology; vol. 22; pp. 45-52.*
Siaut et al. Molecular toolbox for studying diatom biology in Phaeodactylum tricornutum. (2007) Gene; vol. 406; pp. 23-35.*
Walker et al (Plant Cell Rep, 24:629-641, 2005).*
Wuhrer et al (Journal of Chromatography B, 825: 124-133, 2005).*
Baiet et al (JBC, vol. 286(8), p. 6152-6164, 2011).*
International Search Report, dated Jul. 24, 2009, from corresponding PCT application.
Stephen P. Mayfield et al., "Expression and assembly of a fully active antibody in algae", PNAS, Jan. 21, 2003, pp. 438-442, vol. 100, No. 2, XP-002440629.
Rosa Leon-Banares et al., "Transgenic microalgae as green cell-factories", TRENDS in Biotechnology, Jan. 2004, pp. 45-52, vol. 22, No. 1.
Rosa Leon et al., "Nuclear Transformation of Eukaryotic Microalgae", Advances in Experimental Medicine and Biology, 2007, pp. 1-11, vol. 616, XP-009105948.
Yoram Tekoah et al., "Controlled glycosylation of therpeutic antibodies in plants", Archives of Biochemistry and Biophysics, 2004, pp. 266-278, vol. 426, No. 2.

\* cited by examiner

*Primary Examiner* — David T Fox
*Assistant Examiner* — Stephen Uyeno
(74) *Attorney, Agent, or Firm* — Young & Thompson

(57) ABSTRACT

Transformed microalgae capable of expressing glycosylated polypeptides and methods for producing said transformed microalgae and producing glycosylated polypeptides.

10 Claims, 10 Drawing Sheets

SEQUENCE LISTING

```
<160> NUMBER OF SEQ ID NOS: 67

<210> SEQ ID NO 1
<211> LENGTH: 579
<212> TYPE: DNA
<213> ORGANISM: Mus musculus

<400> SEQUENCE: 1 atggggtgc ccgaacgtcc caccctgctg cttttactct ccttgctact gattcctctg      60
ggcctcccag tcctctgtgc tcccccacgc ctcatctgcg acagtcgagt tctggagagg    120
tacatcttag aggccaagga ggcagaaaat gtcacgatgg ttgtgcaga aggtcccaga     180 ctgagtgaaa atattacagt cccagatacc aaagtcaact tctatgcttg gaaaagaatg    240
gaggtggaag aacaggccat agaagtttgg caaggcctgt ccctgctctc agaagccatc    300
ctgcaggccc aggccctgct agccaattcc tcccagccac cagagaccct tcagcttcat    360
atagacaaag ccatcagtgg tctacgtagc ctcacttcac tgcttcgggt actgggagct    420
cagaaggaat tgatgtcgcc tccagatacc accccacctg ctccactccg aacactcaca    480
gtggatactt tctgcaagct cttccgggtc tacgccaact tcctccgggg gaaactgaag    540
ctgtacacgg gagaggtctg caggagaggg gacaggtga                           579

<210> SEQ ID NO 2
<211> LENGTH: 28
<212> TYPE: DNA
<213> ORGANISM: artificial sequence
<220> FEATURE:
<223> OTHER INFORMATION: FE1epo primer

<400> SEQUENCE: 2
catgaattca tgggggtgcc cgaacgtc                                        28

<210> SEQ ID NO 3
<211> LENGTH: 28
<212> TYPE: DNA
<213> ORGANISM: artificial sequence
<220> FEATURE:
<223> OTHER INFORMATION: RH3epo primer

<400> SEQUENCE: 3
cataagcttt cacctgtccc ctctcctg                                        28

<210> SEQ ID NO 4
<211> LENGTH: 50
<212> TYPE: DNA
<213> ORGANISM: artificial sequence
<220> FEATURE:
<223> OTHER INFORMATION: RH3His6epo primer

<400> SEQUENCE: 4
cataagcttt cagtggtggt ggtggtggtg cctgtcccct ctcctgcaga                50
```

```
<210> SEQ ID NO 5
<211> LENGTH: 980
<212> TYPE: DNA
<213> ORGANISM: Homo sapiens

<400> SEQUENCE: 5
atgcatctcc ttgcgattct gttttgtgct ctctggtctg cagtgttggc cgagaactcg      60
gatgattatg atctcatgta tgtgaatttg dacaacgaaa tagacaatgg actccatccc     120
actgaggacc ccacgccgtg cgcctgcggt caggagcact cggaatggga caagctcttc     180
atcatgctgg agaactcgca gatgagagag cgcatgctgc tgcaagccac ggacgacgtc     240
ctgcggggcg agctgcagag gctgcgggag gagctgggcc ggctcgcgga aagcctggcg     300
aggccgtgcg cgccggggc tcccgcagag gccaggctga ccagtgctct ggacgagctg     360
ctgcaggcga cccgcgacgc gggccgcagg ctggcgcgta tggagggcgc ggaggcgcag     420
cgcccagagg aggcggggcg cgccctggcc gcggtgctag aggagctgcg gcagacgcga     480
gccgacctgc acgcggtgca gggctgggct gcccggagct ggctgccggc aggttgtgaa     540
acagctattt tattcccaat gcgttccaag aagattttg gaagcgtgca tccagtgaga       600
ccaatgaggc ttgagtcttt tagtgcctgc atttgggtca aagccacaga tgtattaaac     660
aaaaccatcc tgttttccta tggcacaaag aggaatccat atgaaatcca gctgtatctc     720
agctaccaat ccatagtgtt tgtggtgggt ggagaggaga caaaactggt tgctgaagcc     780
atggtttccc tgggaaggtg gacccacctg tgcggcacct ggaattcaga ggaagggctc     840
acatccttgt gggtaaatgg tgaactggcg gctaccactg ttgagatggc cacaggtcac     900
attgttcctg agggaggaat cctgcagatt ggccaagaaa agaatggctg ctgtgtgggt     960
ggtggctttg atgaaacatt                                                  980

<210> SEQ ID NO 6
<211> LENGTH: 29
<212> TYPE: DNA
<213> ORGANISM: artificial sequence
<220> FEATURE:
<223> OTHER INFORMATION: FE5PTX3 primer

<400> SEQUENCE: 6
catgatatca tgcatctcct tgcgattct                                         29

<210> SEQ ID NO 7
<211> LENGTH: 30
<212> TYPE: DNA
<213> ORGANISM: artificial sequence
<220> FEATURE:
<223> OTHER INFORMATION: RH3PTX3 primer

<400> SEQUENCE: 7
cctaagcttt tatgaaacat actgagctcc                                        30

<210> SEQ ID NO 8
<211> LENGTH: 24
<212> TYPE: DNA
<213> ORGANISM: artificial sequence
<220> FEATURE:
<223> OTHER INFORMATION: FRTepo primer

<400> SEQUENCE: 8
tcttagaggc caaggaggca gaaa                                              24
```

```
<210> SEQ ID NO 9
<211> LENGTH: 24
<212> TYPE: DNA
<213> ORGANISM: artificial sequence
<220> FEATURE:
<223> OTHER INFORMATION: Rrtepo primer

<400> SEQUENCE: 9
acccggaaga gcttgcagaa agta                                              24

<210> SEQ ID NO 10
<211> LENGTH: 19
<212> TYPE: DNA
<213> ORGANISM: artificial sequence
<220> FEATURE:
<223> OTHER INFORMATION: FrtPTX3 primer

<400> SEQUENCE: 10
ctagaggagc tgcggcaga                                                    19

<210> SEQ ID NO 11
<211> LENGTH: 23
<212> TYPE: DNA
<213> ORGANISM: artificial sequence
<220> FEATURE:
<223> OTHER INFORMATION: RrtPTX3 primer

<400> SEQUENCE: 11
cacccaccac aaacactatg gat                                               23

<210> SEQ ID NO 12
<211> LENGTH: 19
<212> TYPE: DNA
<213> ORGANISM: artificial sequence
<220> FEATURE:
<223> OTHER INFORMATION: Fepo primer

<400> SEQUENCE: 12
atgggggtgc ccgaacgtc                                                    19

<210> SEQ ID NO 13
<211> LENGTH: 19
<212> TYPE: DNA
<213> ORGANISM: artificial sequence
<220> FEATURE:
<223> OTHER INFORMATION: Repo primer

<400> SEQUENCE: 13
tcacctgtcc cctctcctg                                                    19

<210> SEQ ID NO 14
<211> LENGTH: 26
<212> TYPE: DNA
<213> ORGANISM: artificial sequence
<220> FEATURE:
<223> OTHER INFORMATION: FpZ primer

<400> SEQUENCE: 14
tcagttctgc acaaatttgt ctgccg                                            26

<210> SEQ ID NO 15
<211> LENGTH: 26
<212> TYPE: DNA
<213> ORGANISM: artificial sequence
<220> FEATURE:
<223> OTHER INFORMATION: RpZ primer

<400> SEQUENCE: 15
```

```
cacgtccctg gttgagttcg atagca                                              26

<210> SEQ ID NO 16
<211> LENGTH: 20
<212> TYPE: DNA
<213> ORGANISM: artificial sequence
<220> FEATURE:
<223> OTHER INFORMATION: FPTX3 primer

<400> SEQUENCE: 16
atgcatctcc ttgcgattct                                                     20

<210> SEQ ID NO 17
<211> LENGTH: 20
<212> TYPE: DNA
<213> ORGANISM: artificial sequence
<220> FEATURE:
<223> OTHER INFORMATION: RPTX3 primer

<400> SEQUENCE: 17
tgaaacatac tgagctcctc                                                     20

<210> SEQ ID NO 18
<211> LENGTH: 447
<212> TYPE: PRT
<213> ORGANISM: Mus musculus

<400> SEQUENCE: 18
```

Met Leu Lys Lys Gln Thr Ala Gly Leu Val Leu Trp Gly Ala Ile Ile
1               5                   10                  15

Phe Val Gly Trp Asn Ala Leu Leu Leu Phe Phe Trp Thr Arg Pro
            20                  25                  30

Ala Pro Gly Arg Leu Pro Ser Asp Ser Ala Leu Gly Asp Asp Pro Ala
        35                  40                  45

Ser Leu Thr Arg Glu Val Ile His Leu Ala Glu Asp Ala Glu Ala Glu
    50                  55                  60

Leu Glu Arg Gln Arg Gly Leu Leu Gln Gln Ile Lys Glu His Tyr Ala
65                  70                  75                  80

Leu Trp Arg Gln Arg Trp Arg Val Pro Thr Val Ala Pro Pro Ala Trp
                85                  90                  95

Pro Arg Val Pro Val Thr Pro Ser Pro Val Gln Ile Pro Ile Leu Val
            100                 105                 110

Ile Ala Cys Asp Arg Ser Thr Val Arg Arg Cys Leu Asp Lys Leu Leu
        115                 120                 125

His Tyr Arg Pro Ser Ala Glu Arg Phe Pro Ile Ile Val Ser Gln Asp
    130                 135                 140

Cys Gly His Glu Glu Thr Ala Gln Val Ile Ala Ser Tyr Gly Thr Ala
145                 150                 155                 160

Val Thr His Ile Arg Gln Pro Asp Leu Ser Asn Ile Ala Val Gln Pro
                165                 170                 175

Asp His Arg Lys Phe Gln Gly Tyr Tyr Lys Ile Ala Arg His Tyr Arg
            180                 185                 190

Trp Ala Leu Gly Gln Ile Phe Asn Lys Phe Lys Phe Pro Ala Ala Val
        195                 200                 205

Val Val Glu Asp Asp Leu Glu Val Ala Pro Asp Phe Phe Glu Tyr Phe
    210                 215                 220

Gln Ala Thr Tyr Pro Leu Leu Arg Thr Asp Pro Ser Leu Trp Cys Val
225                 230                 235                 240

```
Ser Ala Trp Asn Asp Asn Gly Lys Glu Gln Met Val Asp Ser Ser Lys
                245                 250                 255

Pro Glu Leu Leu Tyr Arg Thr Asp Phe Pro Gly Leu Gly Trp Leu
        260                 265                 270

Leu Leu Ala Asp Leu Trp Ala Glu Leu Glu Pro Lys Trp Pro Lys Ala
        275                 280                 285

Phe Trp Asp Asp Trp Met Arg Arg Pro Glu Gln Arg Lys Gly Arg Ala
    290                 295                 300

Cys Ile Arg Pro Glu Ile Ser Arg Thr Met Thr Phe Gly Arg Lys Gly
305                 310                 315                 320

Val Ser His Gly Gln Phe Phe Asp Gln His Leu Lys Phe Ile Lys Leu
                325                 330                 335

Asn Gln Gln Phe Val Pro Phe Thr Gln Leu Asp Leu Ser Tyr Leu Gln
            340                 345                 350

Gln Glu Ala Tyr Asp Arg Asp Phe Leu Ala Gln Val Tyr Gly Ala Pro
        355                 360                 365

Gln Leu Gln Val Glu Lys Val Arg Thr Asn Asp Gln Lys Glu Leu Gly
        370                 375                 380

Glu Val Arg Val Gln Tyr Thr Ser Arg Asp Ser Phe Lys Ala Phe Ala
385                 390                 395                 400

Lys Ala Leu Gly Val Met Asp Asp Leu Lys Ser Gly Val Pro Arg Ala
                405                 410                 415

Gly Tyr Arg Gly Ile Val Thr Phe Gln Phe Arg Gly Arg Val His
            420                 425                 430

Leu Ala Pro Pro Gln Thr Trp Thr Gly Tyr Asp Pro Ser Trp Asn
        435                 440                 445

<210> SEQ ID NO 19
<211> LENGTH: 445
<212> TYPE: PRT
<213> ORGANISM: Homo sapiens

<400> SEQUENCE: 19

Met Leu Lys Lys Gln Ser Ala Gly Leu Val Leu Trp Gly Ala Ile Leu
1               5                   10                  15

Phe Val Ala Trp Asn Ala Leu Leu Leu Phe Phe Trp Thr Arg Pro
            20                  25                  30

Ala Pro Gly Arg Pro Pro Ser Val Ser Ala Leu Asp Gly Asp Pro Ala
        35                  40                  45

Ser Leu Thr Arg Glu Val Ile Arg Leu Ala Gln Asp Ala Glu Val Glu
        50                  55                  60

Leu Glu Arg Gln Arg Gly Leu Leu Gln Gln Ile Gly Asp Ala Leu Ser
65                  70                  75                  80

Ser Gln Arg Gly Arg Val Pro Thr Ala Ala Pro Ala Gln Pro Arg
                85                  90                  95

Val Pro Val Thr Pro Ala Pro Ala Val Ile Pro Ile Leu Val Ile Ala
                100                 105                 110

Cys Asp Arg Ser Thr Val Arg Arg Cys Leu Asp Lys Leu Leu His Tyr
                115                 120                 125

Arg Pro Ser Ala Glu Leu Phe Pro Ile Ile Val Ser Gln Asp Cys Gly
    130                 135                 140

His Glu Glu Thr Ala Gln Ala Ile Ala Ser Tyr Gly Ser Ala Val Thr
145                 150                 155                 160

His Ile Arg Gln Pro Asp Leu Ser Ser Ile Ala Val Pro Pro Asp His
                165                 170                 175
```

```
Arg Lys Phe Gln Gly Tyr Tyr Lys Ile Ala Arg His Tyr Arg Trp Ala
            180                 185                 190

Leu Gly Gln Val Phe Arg Gln Phe Pro Ala Val Val Val
        195                 200                 205

Glu Asp Asp Leu Glu Val Ala Pro Asp Phe Phe Glu Tyr Phe Arg Ala
210                 215                 220

Thr Tyr Pro Leu Leu Lys Ala Asp Pro Ser Leu Trp Cys Val Ser Ala
225                 230                 235                 240

Trp Asn Asp Asn Gly Lys Glu Gln Met Val Asp Ala Ser Arg Pro Glu
                245                 250                 255

Leu Leu Tyr Arg Thr Asp Phe Phe Pro Gly Leu Gly Trp Leu Leu Leu
            260                 265                 270

Ala Glu Leu Trp Ala Glu Leu Glu Pro Lys Trp Pro Lys Ala Phe Trp
        275                 280                 285

Asp Asp Trp Met Arg Arg Pro Glu Gln Arg Gln Gly Arg Ala Cys Ile
290                 295                 300

Arg Pro Glu Ile Ser Arg Thr Met Thr Phe Gly Arg Lys Gly Val Ser
305                 310                 315                 320

His Gly Gln Phe Phe Asp Gln His Leu Lys Phe Ile Lys Leu Asn Gln
                325                 330                 335

Gln Phe Val His Phe Thr Gln Leu Asp Leu Ser Tyr Leu Gln Arg Glu
            340                 345                 350

Ala Tyr Asp Arg Asp Phe Leu Ala Arg Val Tyr Gly Ala Pro Gln Leu
        355                 360                 365

Gln Val Glu Lys Val Arg Thr Asn Asp Arg Lys Glu Leu Gly Glu Val
370                 375                 380

Arg Val Gln Tyr Thr Gly Arg Asp Ser Phe Lys Ala Phe Ala Lys Ala
385                 390                 395                 400

Leu Gly Val Met Asp Asp Leu Lys Ser Gly Val Pro Arg Ala Gly Tyr
                405                 410                 415

Arg Gly Ile Val Thr Phe Gln Phe Arg Gly Arg Val His Leu Ala
            420                 425                 430

Pro Pro Leu Thr Trp Glu Gly Tyr Asp Pro Ser Trp Asn
        435                 440                 445

<210> SEQ ID NO 20
<211> LENGTH: 442
<212> TYPE: PRT
<213> ORGANISM: Mus musculus

<400> SEQUENCE: 20

Met Arg Phe Arg Ile Tyr Lys Arg Lys Val Leu Ile Leu Thr Leu Val
1               5                   10                  15

Val Ala Ala Cys Gly Phe Val Leu Trp Ser Ser Asn Gly Arg Gln Arg
            20                  25                  30

Lys Ser Asp Ala Leu Gly Pro Pro Leu Leu Asp Ala Glu Pro Val Arg
        35                  40                  45

Gly Ala Gly His Leu Ala Val Ser Val Gly Ile Arg Arg Val Ser Asn
    50                  55                  60

Glu Ser Ala Ala Pro Leu Val Pro Ala Val Pro Arg Pro Glu Val Asp
65                  70                  75                  80

Asn Leu Thr Leu Arg Tyr Arg Ser Leu Val Tyr Gln Leu Asn Phe Asp
                85                  90                  95

Gln Met Leu Arg Asn Val Gly Asn Asp Gly Thr Trp Ser Pro Gly Glu
            100                 105                 110
```

```
Leu Val Leu Val Val Gln Val His Asn Arg Pro Glu Tyr Leu Arg Leu
        115                 120                 125

Leu Ile Asp Ser Leu Arg Lys Ala Gln Gly Ile Gln Glu Val Leu Val
130                 135                 140

Ile Phe Ser His Asp Phe Trp Ser Ala Glu Ile Asn Ser Leu Ile Ser
145                 150                 155                 160

Arg Val Asp Phe Cys Pro Val Leu Gln Val Phe Phe Pro Phe Ser Ile
                165                 170                 175

Gln Leu Tyr Pro Asn Glu Phe Pro Gly Ser Asp Pro Arg Asp Cys Pro
            180                 185                 190

Arg Asp Leu Lys Lys Asn Ala Ala Leu Lys Leu Gly Cys Ile Asn Ala
        195                 200                 205

Glu Tyr Pro Asp Ser Phe Gly His Tyr Arg Glu Ala Lys Phe Ser Gln
210                 215                 220

Thr Lys His His Trp Trp Lys Leu His Phe Val Trp Glu Arg Val
225                 230                 235                 240

Lys Val Leu Gln Asp Tyr Thr Gly Leu Ile Leu Phe Leu Glu Glu Asp
                245                 250                 255

His Tyr Leu Ala Pro Asp Phe Tyr His Val Phe Lys Lys Met Trp Lys
            260                 265                 270

Leu Lys Gln Gln Glu Cys Pro Gly Cys Asp Val Leu Ser Leu Gly Thr
        275                 280                 285

Tyr Thr Thr Ile Arg Ser Phe Tyr Gly Ile Ala Asp Lys Val Asp Val
290                 295                 300

Lys Thr Trp Lys Ser Thr Glu His Asn Met Gly Leu Ala Leu Thr Arg
305                 310                 315                 320

Asp Ala Tyr Gln Lys Leu Ile Glu Cys Thr Asp Thr Phe Cys Thr Tyr
                325                 330                 335

Asp Asp Tyr Asn Trp Asp Trp Thr Leu Gln Tyr Leu Thr Leu Ala Cys
            340                 345                 350

Leu Pro Lys Ile Trp Lys Val Leu Val Pro Gln Ala Pro Arg Ile Phe
        355                 360                 365

His Ala Gly Asp Cys Gly Met His His Lys Lys Thr Cys Arg Pro Ser
370                 375                 380

Thr Gln Ser Ala Gln Ile Glu Ser Leu Leu Asn Ser Asn Lys Gln Tyr
385                 390                 395                 400

Leu Phe Pro Glu Thr Leu Val Ile Gly Glu Lys Phe Pro Met Ala Ala
                405                 410                 415

Ile Ser Pro Pro Arg Lys Asn Gly Gly Trp Gly Asp Ile Arg Asp His
            420                 425                 430

Glu Leu Cys Lys Ser Tyr Arg Arg Leu Gln
        435                 440

<210> SEQ ID NO 21
<211> LENGTH: 447
<212> TYPE: PRT
<213> ORGANISM: Homo sapiens

<400> SEQUENCE: 21

Met Arg Phe Arg Ile Tyr Lys Arg Lys Val Leu Ile Leu Thr Leu Val
1               5                   10                  15

Val Ala Ala Cys Gly Phe Val Leu Trp Ser Ser Asn Gly Arg Gln Arg
                20                  25                  30

Lys Asn Glu Ala Leu Ala Pro Pro Leu Leu Asp Ala Glu Pro Ala Arg
        35                  40                  45
```

-continued

Gly Ala Gly Gly Arg Gly Gly Asp His Pro Ser Val Ala Gly Ile
         50                  55                  60

Arg Arg Val Ser Asn Val Ser Ala Ala Ser Leu Val Pro Ala Val Pro
 65                  70                  75                  80

Gln Pro Glu Ala Asp Asn Leu Thr Leu Arg Tyr Arg Ser Leu Val Tyr
                 85                  90                  95

Gln Leu Asn Phe Asp Gln Thr Leu Arg Asn Val Asp Lys Ala Gly Thr
                100                 105                 110

Trp Ala Pro Arg Glu Leu Val Leu Val Val Gln Val His Asn Arg Pro
                115                 120                 125

Glu Tyr Leu Arg Leu Leu Asp Ser Leu Arg Lys Ala Gln Gly Ile
        130                 135                 140

Asp Asn Val Leu Val Ile Phe Ser His Asp Phe Trp Ser Thr Glu Ile
145                 150                 155                 160

Asn Gln Leu Ile Ala Gly Val Asn Phe Cys Pro Val Leu Gln Val Phe
                165                 170                 175

Phe Pro Phe Ser Ile Gln Leu Tyr Pro Asn Glu Phe Pro Gly Ser Asp
                180                 185                 190

Pro Arg Asp Cys Pro Arg Asp Leu Pro Lys Asn Ala Ala Leu Lys Leu
                195                 200                 205

Gly Cys Ile Asn Ala Glu Tyr Pro Asp Ser Phe Gly His Tyr Arg Glu
        210                 215                 220

Ala Lys Phe Ser Gln Thr Lys His His Trp Trp Lys Leu His Phe
225                 230                 235                 240

Val Trp Glu Arg Val Lys Ile Leu Arg Asp Tyr Ala Gly Leu Ile Leu
                245                 250                 255

Phe Leu Glu Glu Asp His Tyr Leu Ala Pro Asp Phe Tyr His Val Phe
        260                 265                 270

Lys Lys Met Trp Lys Leu Lys Gln Gln Glu Cys Pro Glu Cys Asp Val
        275                 280                 285

Leu Ser Leu Gly Thr Tyr Ser Ala Ser Arg Ser Phe Tyr Gly Met Ala
        290                 295                 300

Asp Lys Val Asp Val Lys Thr Trp Lys Ser Thr Glu His Asn Met Gly
305                 310                 315                 320

Leu Ala Leu Thr Arg Asn Ala Tyr Gln Lys Leu Ile Glu Cys Thr Asp
                325                 330                 335

Thr Phe Cys Thr Tyr Asp Asp Tyr Asn Trp Asp Trp Thr Leu Gln Tyr
                340                 345                 350

Leu Thr Val Ser Cys Leu Pro Lys Phe Trp Lys Val Leu Val Pro Gln
        355                 360                 365

Ile Pro Arg Ile Phe His Ala Gly Asp Cys Gly Met His His Lys Lys
370                 375                 380

Thr Cys Arg Pro Ser Thr Gln Ser Ala Gln Ile Glu Ser Leu Leu Asn
385                 390                 395                 400

Asn Asn Lys Gln Tyr Met Phe Pro Glu Thr Leu Thr Ile Ser Glu Lys
                405                 410                 415

Phe Thr Val Val Ala Ile Ser Pro Pro Arg Lys Asn Gly Gly Trp Gly
                420                 425                 430

Asp Ile Arg Asp His Glu Leu Cys Lys Ser Tyr Arg Arg Leu Gln
        435                 440                 445

<210> SEQ ID NO 22
<211> LENGTH: 538
<212> TYPE: PRT
<213> ORGANISM: Mus musculus

<400> SEQUENCE: 22

```
Met Lys Met Arg Arg Tyr Lys Leu Phe Leu Met Phe Cys Met Ala Gly
1               5                   10                  15

Leu Cys Leu Ile Ser Phe Leu His Phe Phe Lys Thr Leu Ser Tyr Val
            20                  25                  30

Thr Phe Pro Arg Glu Leu Ala Ser Leu Ser Pro Asn Leu Val Ser Ser
        35                  40                  45

Phe Phe Trp Asn Asn Ala Pro Val Thr Pro Gln Ala Ser Pro Glu Pro
    50                  55                  60

Gly Gly Pro Asp Leu Leu Arg Thr Pro Leu Tyr Ser His Ser Pro Leu
65                  70                  75                  80

Leu Gln Pro Leu Ser Pro Ser Lys Ala Thr Glu Glu Leu His Arg Val
                85                  90                  95

Asp Phe Val Leu Pro Glu Asp Thr Thr Glu Tyr Phe Val Arg Thr Lys
            100                 105                 110

Ala Gly Gly Val Cys Phe Lys Pro Gly Thr Arg Met Leu Glu Lys Pro
        115                 120                 125

Ser Pro Gly Arg Thr Glu Glu Lys Pro Glu Val Ser Glu Gly Ser Ser
    130                 135                 140

Ala Arg Gly Pro Ala Arg Arg Pro Met Arg His Val Leu Ser Thr Arg
145                 150                 155                 160

Glu Arg Leu Gly Ser Arg Gly Thr Arg Arg Lys Trp Val Glu Cys Val
                165                 170                 175

Cys Leu Pro Gly Trp His Gly Pro Ser Cys Gly Val Pro Thr Val Val
            180                 185                 190

Gln Tyr Ser Asn Leu Pro Thr Lys Glu Arg Leu Val Pro Arg Glu Val
        195                 200                 205

Pro Arg Arg Val Ile Asn Ala Ile Asn Ile Asn His Glu Phe Asp Leu
    210                 215                 220

Leu Asp Val Arg Phe His Glu Leu Gly Asp Val Val Asp Ala Phe Val
225                 230                 235                 240

Val Cys Glu Ser Asn Phe Thr Ala Tyr Gly Glu Pro Arg Pro Leu Lys
                245                 250                 255

Phe Arg Glu Met Leu Thr Asn Gly Thr Phe Glu Tyr Ile Arg His Lys
            260                 265                 270

Val Leu Tyr Val Phe Leu Asp His Phe Pro Pro Gly Gly Arg Gln Asp
        275                 280                 285

Gly Trp Ile Ala Asp Asp Tyr Leu Arg Thr Phe Leu Thr Gln Asp Gly
    290                 295                 300

Val Ser Arg Leu Arg Asn Leu Arg Pro Asp Asp Val Phe Ile Ile Asp
305                 310                 315                 320

Asp Ala Asp Glu Ile Pro Ala Arg Asp Gly Val Leu Phe Leu Lys Leu
                325                 330                 335

Tyr Asp Gly Trp Thr Glu Pro Phe Ala Phe His Met Arg Lys Ser Leu
            340                 345                 350

Tyr Gly Phe Phe Trp Lys Gln Pro Gly Thr Leu Glu Val Val Ser Gly
        355                 360                 365

Cys Thr Met Asp Met Leu Gln Ala Val Tyr Gly Leu Asp Gly Ile Arg
    370                 375                 380

Leu Arg Arg Arg Gln Tyr Tyr Thr Met Pro Asn Phe Arg Gln Tyr Glu
385                 390                 395                 400

Asn Arg Thr Gly His Ile Leu Val Gln Trp Ser Leu Gly Ser Pro Leu
                405                 410                 415
```

His Phe Ala Gly Trp His Cys Ser Trp Cys Phe Thr Pro Glu Gly Ile
            420                 425                 430

Tyr Phe Lys Leu Val Ser Ala Gln Asn Gly Asp Phe Pro Arg Trp Gly
        435                 440                 445

Asp Tyr Glu Asp Lys Arg Asp Leu Asn Tyr Ile Arg Ser Leu Ile Arg
    450                 455                 460

Thr Gly Gly Trp Phe Asp Gly Thr Gln Gln Glu Tyr Pro Pro Ala Asp
465                 470                 475                 480

Pro Ser Glu His Met Tyr Ala Pro Lys Tyr Leu Lys Asn Tyr Asp
                485                 490                 495

Gln Phe Arg Tyr Leu Leu Glu Asn Pro Tyr Arg Glu Pro Lys Ser Thr
            500                 505                 510

Glu Glu Gly Gly Arg Arg Asn Gln Gly Ser Asp Gly Arg Pro Ser Ala
            515                 520                 525

Val Arg Gly Lys Leu Asp Thr Val Glu Gly
            530                 535

<210> SEQ ID NO 23
<211> LENGTH: 533
<212> TYPE: PRT
<213> ORGANISM: Homo sapiens

<400> SEQUENCE: 23

Met Lys Met Arg Arg Tyr Lys Leu Phe Leu Met Phe Cys Met Ala Gly
1               5                   10                  15

Leu Cys Leu Ile Ser Phe Leu His Phe Phe Lys Thr Leu Ser Tyr Val
            20                  25                  30

Thr Phe Pro Arg Glu Leu Ala Ser Leu Ser Pro Asn Leu Val Ser Ser
        35                  40                  45

Phe Phe Trp Asn Asn Ala Pro Val Thr Pro Gln Ala Ser Pro Glu Pro
    50                  55                  60

Gly Gly Pro Asp Leu Leu Arg Thr Pro Leu Tyr Ser His Ser Pro Leu
65                  70                  75                  80

Leu Gln Pro Leu Pro Pro Ser Lys Ala Ala Glu Glu Leu His Arg Val
                85                  90                  95

Asp Leu Val Leu Pro Glu Asp Thr Thr Glu Tyr Phe Val Arg Thr Lys
            100                 105                 110

Ala Gly Gly Val Cys Phe Lys Pro Gly Thr Lys Met Leu Glu Arg Pro
        115                 120                 125

Pro Pro Gly Arg Pro Glu Glu Lys Pro Glu Gly Ala Asn Gly Ser Ser
    130                 135                 140

Ala Arg Arg Pro Pro Arg Tyr Leu Leu Ser Ala Arg Glu Arg Thr Gly
145                 150                 155                 160

Gly Arg Gly Ala Arg Arg Lys Trp Val Glu Cys Val Cys Leu Pro Gly
                165                 170                 175

Trp His Gly Pro Ser Cys Gly Val Pro Thr Val Val Gln Tyr Ser Asn
            180                 185                 190

Leu Pro Thr Lys Glu Arg Leu Val Pro Arg Glu Val Pro Arg Arg Val
        195                 200                 205

Ile Asn Ala Ile Asn Val Asn His Glu Phe Asp Leu Leu Asp Val Arg
    210                 215                 220

Phe His Glu Leu Gly Asp Val Val Asp Ala Phe Val Val Cys Glu Ser
225                 230                 235                 240

Asn Phe Thr Ala Tyr Gly Glu Pro Arg Pro Leu Lys Phe Arg Glu Met
                245                 250                 255

Leu Thr Asn Gly Thr Phe Glu Tyr Ile Arg His Lys Val Leu Tyr Val
            260                 265                 270

Phe Leu Asp His Phe Pro Pro Gly Gly Arg Gln Asp Gly Trp Ile Ala
            275                 280                 285

Asp Asp Tyr Leu Arg Thr Phe Leu Thr Gln Asp Gly Val Ser Arg Leu
            290                 295                 300

Arg Asn Leu Arg Pro Asp Asp Val Phe Ile Ile Asp Ala Asp Glu
305                 310                 315                 320

Ile Pro Ala Arg Asp Gly Val Leu Phe Leu Lys Leu Tyr Asp Gly Trp
            325                 330                 335

Thr Glu Pro Phe Ala Phe His Met Arg Lys Ser Leu Tyr Gly Phe Phe
            340                 345                 350

Trp Lys Gln Pro Gly Thr Leu Glu Val Val Ser Gly Cys Thr Val Asp
            355                 360                 365

Met Leu Gln Ala Val Tyr Gly Leu Asp Gly Ile Arg Leu Arg Arg Arg
            370                 375                 380

Gln Tyr Tyr Thr Met Pro Asn Phe Arg Gln Tyr Glu Asn Arg Thr Gly
385                 390                 395                 400

His Ile Leu Val Gln Trp Ser Leu Gly Ser Pro Leu His Phe Ala Gly
            405                 410                 415

Trp His Cys Ser Trp Cys Phe Thr Pro Glu Gly Ile Tyr Phe Lys Leu
            420                 425                 430

Val Ser Ala Gln Asn Gly Asp Phe Pro Arg Trp Gly Asp Tyr Glu Asp
            435                 440                 445

Lys Arg Asp Leu Asn Tyr Ile Arg Gly Leu Ile Arg Thr Gly Gly Trp
            450                 455                 460

Phe Asp Gly Thr Gln Gln Glu Tyr Pro Pro Ala Asp Pro Ser Glu His
465                 470                 475                 480

Met Tyr Ala Pro Lys Tyr Leu Leu Lys Asn Tyr Asp Arg Phe His Tyr
            485                 490                 495

Leu Leu Asp Asn Pro Tyr Gln Glu Pro Arg Ser Thr Ala Ala Gly Gly
            500                 505                 510

Trp Arg His Arg Gly Pro Glu Gly Arg Pro Pro Ala Arg Gly Lys Leu
            515                 520                 525

Asp Glu Ala Glu Val
            530

<210> SEQ ID NO 24
<211> LENGTH: 535
<212> TYPE: PRT
<213> ORGANISM: Mus musculus

<400> SEQUENCE: 24

Met Arg Leu Arg Asn Gly Thr Val Ala Thr Ala Leu Val Phe Val Thr
1               5                   10                  15

Ser Phe Leu Thr Leu Ser Trp Tyr Thr Thr Trp Gln Asn Gly Lys Glu
            20                  25                  30

Lys Leu Ile Ala Tyr Gln Arg Glu Phe Leu Ala Leu Lys Glu Arg Leu
            35                  40                  45

Arg Val Ala Glu His Arg Ile Ser Gln Arg Ser Glu Leu Asn Thr
        50                  55                  60

Ile Val Gln Gln Phe Arg Arg Ala Gly Ala Glu Thr Asn Gly Ser Lys
65                  70                  75                  80

Thr Ala Leu Ser Thr Ile Ser Asp Asn Thr Ile Lys Leu Leu Lys Glu
            85                  90                  95

```
Leu Thr Ser Lys Lys Ser Leu Arg Val Pro Ser Ile Tyr Tyr His Leu
            100                 105                 110

Pro His Leu Leu Gln Asn Glu Arg Ser Leu Gln Pro Ala Val Gln Ile
            115                 120                 125

Gly Ser Gly Arg Thr Gly Val Ser Ile Val Met Gly Ile Pro Thr Val
130                 135                 140

Lys Arg Glu Val Lys Ser Tyr Leu Val Glu Thr Leu His Ser Leu Ile
145                 150                 155                 160

Asp Asn Leu Tyr Pro Glu Glu Lys Leu Asp Cys Val Ile Val Val Phe
                165                 170                 175

Ile Gly Glu Thr Asp Leu Asp Tyr Val His Ser Val Val Ala Asn Leu
            180                 185                 190

Glu Lys Glu Phe Ser Arg Glu Ile Ser Ser Gly Leu Leu Glu Ile Ile
            195                 200                 205

Ser Pro Pro Glu Ser Tyr Tyr Pro Asp Leu Thr Asn Leu Lys Glu Thr
210                 215                 220

Phe Gly Asp Ser Lys Glu Arg Val Arg Trp Arg Thr Lys Gln Asn Leu
225                 230                 235                 240

Asp Tyr Cys Phe Leu Met Met Tyr Ala Gln Glu Lys Gly Ile Tyr Tyr
                245                 250                 255

Ile Gln Leu Glu Asp Asp Ile Ile Val Lys Gln Asn Tyr Phe Asn Thr
            260                 265                 270

Ile Lys Asn Phe Ala Leu Gln Leu Ser Ser Glu Glu Trp Met Ile Leu
            275                 280                 285

Glu Phe Ser Gln Leu Gly Phe Ile Gly Lys Met Phe Gln Ala Pro Asp
            290                 295                 300

Leu Ala Leu Val Val Glu Phe Ile Leu Met Phe Tyr Lys Glu Lys Pro
305                 310                 315                 320

Ile Asp Trp Leu Leu Asp His Ile Leu Trp Val Lys Val Cys Asn Pro
                325                 330                 335

Glu Lys Asp Ala Lys His Cys Asp Arg Gln Lys Ala Asn Leu Arg Ile
            340                 345                 350

Arg Phe Arg Pro Ser Leu Phe Gln His Val Gly Leu His Ser Ser Leu
            355                 360                 365

Ser Gly Lys Ile Gln Lys Leu Thr Asp Lys Asp Tyr Met Lys Pro Leu
370                 375                 380

Leu Leu Lys Val His Val Asn Pro Pro Ala Glu Val Ser Thr Ser Leu
385                 390                 395                 400

Lys Val Tyr Gln Gly His Thr Leu Glu Lys Thr Tyr Met Gly Glu Asp
                405                 410                 415

Phe Phe Trp Ala Ile Thr Pro Thr Ala Gly Asp Tyr Ile Leu Phe Lys
            420                 425                 430

Phe Asp Lys Pro Val Asn Val Glu Ser Tyr Leu Phe His Ser Gly Asn
            435                 440                 445

Gln Glu His Pro Gly Asp Ile Leu Leu Asn Thr Thr Val Asp Val Leu
450                 455                 460

Pro Leu Lys Ser Asp Ser Leu Glu Ile Ser Lys Glu Thr Lys Asp Lys
465                 470                 475                 480

Arg Leu Glu Asp Gly Tyr Phe Arg Ile Gly Lys Phe Glu Tyr Gly Val
                485                 490                 495

Ala Glu Gly Ile Val Asp Pro Gly Leu Asn Pro Ile Ser Ala Phe Arg
            500                 505                 510

Leu Ser Val Ile Gln Asn Ser Ala Val Trp Ala Ile Leu Asn Glu Ile
```

```
                515                 520                 525
His Ile Lys Lys Val Thr Ser
    530                 535

<210> SEQ ID NO 25
<211> LENGTH: 548
<212> TYPE: PRT
<213> ORGANISM: Mus musculus

<400> SEQUENCE: 25

Met Arg Leu Arg Asn Gly Thr Phe Leu Thr Leu Leu Phe Cys Leu
1               5                   10                  15

Cys Ala Phe Leu Ser Leu Ser Trp Tyr Ala Ala Leu Ser Gly Gln Lys
            20                  25                  30

Gly Asp Val Val Asp Ile Tyr Gln Arg Glu Phe Leu Ala Leu Arg Asp
            35                  40                  45

Arg Leu His Ala Ala Glu Gln Glu Ser Leu Lys Arg Ser Lys Glu Leu
    50                  55                  60

Asn Leu Val Leu Glu Glu Ile Lys Arg Ala Val Ser Glu Arg Gln Ala
65                  70                  75                  80

Leu Arg Asp Gly Glu Gly Asn Arg Thr Trp Gly Arg Leu Thr Glu Asp
                85                  90                  95

Pro Arg Leu Lys Pro Trp Asn Val Ser His Arg His Val Leu His Leu
            100                 105                 110

Pro Thr Val Phe His His Leu Pro His Leu Leu Ala Lys Glu Ser Ser
            115                 120                 125

Leu Gln Pro Ala Val Arg Val Gly Gln Gly Arg Thr Gly Val Ser Val
    130                 135                 140

Val Met Gly Ile Pro Ser Val Arg Arg Glu Val His Ser Tyr Leu Thr
145                 150                 155                 160

Asp Thr Leu His Ser Leu Ile Ser Glu Leu Ser Pro Gln Glu Lys Glu
                165                 170                 175

Asp Ser Val Ile Val Val Leu Ile Ala Glu Thr Asp Pro Gln Tyr Thr
            180                 185                 190

Ser Ala Val Thr Glu Asn Ile Lys Ala Leu Phe Pro Thr Glu Ile His
            195                 200                 205

Ser Gly Leu Leu Glu Val Ile Ser Pro Ser Pro His Phe Tyr Pro Asp
    210                 215                 220

Phe Ser Arg Leu Arg Glu Ser Phe Gly Asp Pro Lys Glu Arg Val Arg
225                 230                 235                 240

Trp Arg Thr Lys Gln Asn Leu Asp Tyr Cys Phe Leu Met Met Tyr Ala
                245                 250                 255

Gln Ser Lys Gly Ile Tyr Tyr Val Gln Leu Glu Asp Asp Ile Val Ala
            260                 265                 270

Lys Pro Asn Tyr Leu Ser Thr Met Lys Asn Phe Ala Leu Gln Gln Pro
            275                 280                 285

Ser Glu Asp Trp Met Ile Leu Glu Phe Ser Gln Leu Gly Phe Ile Gly
    290                 295                 300

Lys Met Phe Lys Ser Leu Asp Leu Ser Leu Ile Val Glu Phe Ile Leu
305                 310                 315                 320

Met Phe Tyr Arg Asp Lys Pro Ile Asp Trp Leu Leu Asp His Ile Leu
                325                 330                 335

Trp Val Lys Val Cys Asn Pro Glu Lys Asp Ala Lys His Cys Asp Arg
            340                 345                 350

Gln Lys Ala Asn Leu Arg Ile Arg Phe Lys Pro Ser Leu Phe Gln His
```

```
                   355                 360                 365
Val Gly Thr His Ser Ser Leu Ala Gly Lys Ile Gln Lys Leu Lys Asp
370                 375                 380

Lys Asp Phe Gly Lys His Ala Leu Arg Lys Ser Tyr Val Asn Pro Pro
385                 390                 395                 400

Ala Glu Val Ser Thr Ser Leu Lys Thr Tyr Gln His Phe Thr Leu Glu
                405                 410                 415

Lys Ala Tyr Leu Arg Glu Asp Phe Phe Trp Ala Phe Thr Pro Ala Ala
                420                 425                 430

Gly Asp Phe Ile Arg Phe Arg Phe Gln Pro Leu Arg Leu Glu Arg
            435                 440                 445

Phe Phe Phe Arg Ser Gly Asn Ile Glu His Pro Glu Asp Lys Leu Phe
450                 455                 460

Asn Thr Ser Val Glu Val Leu Pro Phe Asp Asn Pro Gln Ser Glu Lys
465                 470                 475                 480

Glu Ala Leu Gln Glu Gly Arg Ser Ala Thr Leu Arg Tyr Pro Arg Ser
                485                 490                 495

Pro Asp Gly Tyr Leu Gln Ile Gly Ser Phe Tyr Lys Gly Val Ala Glu
            500                 505                 510

Gly Glu Val Asp Pro Ala Phe Gly Pro Leu Glu Ala Leu Arg Leu Ser
            515                 520                 525

Ile Gln Thr Asp Ser Pro Val Trp Val Ile Leu Ser Glu Ile Phe Leu
530                 535                 540

Lys Lys Ala Asp
545

<210> SEQ ID NO 26
<211> LENGTH: 478
<212> TYPE: PRT
<213> ORGANISM: Mus musculus

<400> SEQUENCE: 26

Met Leu Lys Phe Tyr Gln Met Lys Tyr Ile Phe Gln Ile Leu Asp Lys
1               5                   10                  15

Met Arg Cys Leu Arg Lys Arg Ser Thr Val Ser Phe Leu Gly Val Leu
                20                  25                  30

Val Val Phe Leu Leu Phe Met Asn Leu Tyr Ile Glu Asp Ser Tyr Val
            35                  40                  45

Leu Glu Gly Asp Lys Gln Leu Ile Arg Glu Thr Ser Thr His Gln Leu
        50                  55                  60

Asn Ser Glu Arg Tyr Val His Thr Phe Lys Asp Leu Ser Asn Phe Ser
65                  70                  75                  80

Gly Thr Ile Asn Val Thr Tyr Arg Tyr Leu Ala Ala Thr Pro Leu Gln
                85                  90                  95

Arg Lys Arg Tyr Leu Thr Ile Gly Leu Ser Ser Val Lys Arg Lys Lys
                100                 105                 110

Gly Asn Tyr Leu Leu Asp Thr Ile Lys Ser Ile Phe Glu Gln Ser Ser
            115                 120                 125

Tyr Glu Glu Leu Lys Glu Ile Ser Val Val His Leu Ala Asp Phe
130                 135                 140

Asn Ser Ser Trp Arg Asp Ala Met Val Gln Asp Ile Thr Gln Lys Phe
145                 150                 155                 160

Ala His His Ile Ile Ala Gly Arg Leu Met Val Ile His Ala Pro Glu
                165                 170                 175

Glu Tyr Tyr Pro Val Leu Asp Gly Leu Lys Arg Asn Tyr Asn Asp Pro
```

```
                180                 185                 190
Glu Asp Arg Val Arg Phe Arg Ser Lys Gln Asn Val Asp Tyr Ala Phe
            195                 200                 205

Leu Leu Asn Phe Cys Ala Asn Thr Ser Asp Tyr Tyr Val Met Leu Glu
        210                 215                 220

Asp Asp Val Arg Cys Ser Arg Asn Phe Leu Thr Ala Ile Lys Lys Val
225                 230                 235                 240

Ile Ala Ser Leu Glu Gly Thr Tyr Trp Val Thr Leu Glu Phe Ser Lys
                245                 250                 255

Leu Gly Tyr Ile Gly Lys Leu Tyr His Ser His Asp Leu Pro Arg Leu
            260                 265                 270

Ala His Phe Leu Leu Met Phe Tyr Gln Glu Met Pro Cys Asp Trp Leu
        275                 280                 285

Leu Thr His Phe Arg Gly Leu Leu Ala Gln Lys Asn Val Ile Arg Phe
        290                 295                 300

Lys Pro Ser Leu Phe Gln His Met Gly Tyr Tyr Ser Ser Tyr Lys Gly
305                 310                 315                 320

Thr Glu Asn Lys Leu Lys Asp Asp Phe Glu Glu Ser Phe Asp
                325                 330                 335

Ile Pro Asp Asn Pro Ala Ser Phe Tyr Thr Asn Met Asn Val Phe
                340                 345                 350

Glu Asn Tyr Glu Ala Ser Lys Ala Tyr Ser Ser Val Asp Glu Tyr Phe
                355                 360                 365

Trp Gly Lys Ser Pro Ser Met Gly Asp Thr Phe Val Ile Val Phe Glu
        370                 375                 380

Asn Pro Ile Thr Ile Lys Lys Ile Lys Val Asn Thr Gly Thr Glu Asp
385                 390                 395                 400

Arg Gln Asn Asp Ile Leu Gln His Gly Ala Leu Asp Val Gly Glu Lys
                405                 410                 415

Leu Ile Phe Ser Lys Gln Ile Arg Gln Cys Asp Thr Tyr Leu Arg Leu
                420                 425                 430

Gly Glu Phe Lys Asn Gly Tyr Phe Glu Met Ser Asp Val Asn Gln Lys
        435                 440                 445

Ile Pro Phe Asp Ile His Cys Met Arg Ile Cys Val Thr Lys Thr Gln
        450                 455                 460

Lys Glu Trp Leu Ile Ile Arg Ser Ile Ser Ile Trp Thr Ser
465                 470                 475

<210> SEQ ID NO 27
<211> LENGTH: 535
<212> TYPE: PRT
<213> ORGANISM: Homo sapiens

<400> SEQUENCE: 27

Met Arg Leu Arg Asn Gly Thr Val Ala Thr Ala Leu Ala Phe Ile Thr
1               5                   10                  15

Ser Phe Leu Thr Leu Ser Trp Tyr Thr Thr Trp Gln Asn Gly Lys Glu
            20                  25                  30

Lys Leu Ile Ala Tyr Gln Arg Glu Phe Leu Ala Leu Lys Glu Arg Leu
        35                  40                  45

Arg Ile Ala Glu His Arg Ile Ser Gln Arg Ser Glu Leu Asn Thr
    50                  55                  60

Ile Val Gln Gln Phe Lys Arg Val Gly Ala Glu Thr Asn Gly Ser Lys
65                  70                  75                  80

Asp Ala Leu Asn Lys Phe Ser Asp Asn Thr Leu Lys Leu Leu Lys Glu
```

```
                        85                  90                  95
Leu Thr Ser Lys Lys Ser Leu Gln Val Pro Ser Ile Tyr Tyr His Leu
                100                 105                 110

Pro His Leu Leu Lys Asn Glu Gly Ser Leu Gln Pro Ala Val Gln Ile
            115                 120                 125

Gly Asn Gly Arg Thr Gly Val Ser Ile Val Met Gly Ile Pro Thr Val
        130                 135                 140

Lys Arg Glu Val Lys Ser Tyr Leu Ile Glu Thr Leu His Ser Leu Ile
145                 150                 155                 160

Asp Asn Leu Tyr Pro Glu Glu Lys Leu Asp Cys Val Ile Val Val Phe
                165                 170                 175

Ile Gly Glu Thr Asp Ile Asp Tyr Val His Gly Val Val Ala Asn Leu
            180                 185                 190

Glu Lys Glu Phe Ser Lys Glu Ile Ser Ser Gly Leu Val Glu Val Ile
        195                 200                 205

Ser Pro Pro Glu Ser Tyr Tyr Pro Asp Leu Thr Asn Leu Lys Glu Thr
    210                 215                 220

Phe Gly Asp Ser Lys Glu Arg Val Arg Trp Arg Thr Lys Gln Asn Leu
225                 230                 235                 240

Asp Tyr Cys Phe Leu Met Met Tyr Ala Gln Glu Lys Gly Ile Tyr Tyr
                245                 250                 255

Ile Gln Leu Glu Asp Asp Ile Ile Val Lys Gln Asn Tyr Phe Asn Thr
            260                 265                 270

Ile Lys Asn Phe Ala Leu Gln Leu Ser Ser Glu Glu Trp Met Ile Leu
        275                 280                 285

Glu Phe Ser Gln Leu Gly Phe Ile Gly Lys Met Phe Gln Ala Pro Asp
    290                 295                 300

Leu Thr Leu Ile Val Glu Phe Ile Phe Met Phe Tyr Lys Glu Lys Pro
305                 310                 315                 320

Ile Asp Trp Leu Leu Asp His Ile Leu Trp Val Lys Val Cys Asn Pro
                325                 330                 335

Glu Lys Asp Ala Lys His Cys Asp Arg Gln Lys Ala Asn Leu Arg Ile
            340                 345                 350

Arg Phe Arg Pro Ser Leu Phe Gln His Val Gly Leu His Ser Ser Leu
        355                 360                 365

Ser Gly Lys Ile Gln Lys Leu Thr Asp Lys Asp Tyr Met Lys Pro Leu
    370                 375                 380

Leu Leu Lys Ile His Val Asn Pro Pro Ala Glu Val Ser Thr Ser Leu
385                 390                 395                 400

Lys Val Tyr Gln Gly His Thr Leu Glu Lys Thr Tyr Met Gly Glu Asp
                405                 410                 415

Phe Phe Trp Ala Ile Thr Pro Ile Ala Gly Asp Tyr Ile Leu Phe Lys
            420                 425                 430

Phe Asp Lys Pro Val Asn Val Glu Ser Tyr Leu Phe His Ser Gly Asn
        435                 440                 445

Gln Glu His Pro Gly Asp Ile Leu Leu Asn Thr Thr Val Glu Val Leu
    450                 455                 460

Pro Phe Lys Ser Glu Gly Leu Glu Ile Ser Lys Glu Thr Lys Asp Lys
465                 470                 475                 480

Arg Leu Glu Asp Gly Tyr Phe Arg Ile Gly Lys Phe Glu Asn Gly Val
                485                 490                 495

Ala Glu Gly Met Val Asp Pro Ser Leu Asn Pro Ile Ser Ala Phe Arg
            500                 505                 510
```

```
Leu Ser Val Ile Gln Asn Ser Ala Val Trp Ala Ile Leu Asn Glu Ile
        515                 520                 525

His Ile Lys Lys Ala Thr Asn
        530                 535
```

<210> SEQ ID NO 28
<211> LENGTH: 548
<212> TYPE: PRT
<213> ORGANISM: Homo sapiens

<400> SEQUENCE: 28

```
Met Arg Leu Arg Asn Gly Thr Phe Thr Leu Leu Leu Phe Cys Leu
1               5                   10                  15

Cys Ala Phe Leu Ser Leu Ser Trp Tyr Ala Ala Leu Ser Gly Gln Lys
                20                  25                  30

Gly Asp Val Val Asp Val Tyr Gln Arg Glu Phe Leu Ala Leu Arg Asp
            35                  40                  45

Arg Leu His Ala Ala Glu Gln Glu Ser Leu Lys Arg Ser Lys Glu Leu
50                  55                  60

Asn Leu Val Leu Asp Glu Ile Lys Arg Ala Val Ser Glu Arg Gln Ala
65                  70                  75                  80

Leu Arg Asp Gly Asp Gly Asn Arg Thr Trp Gly Arg Leu Thr Glu Asp
                85                  90                  95

Pro Arg Leu Lys Pro Trp Asn Gly Ser His Arg His Val Leu His Leu
            100                 105                 110

Pro Thr Val Phe His His Leu Pro His Leu Leu Ala Lys Glu Ser Ser
        115                 120                 125

Leu Gln Pro Ala Val Arg Val Gly Gln Gly Arg Thr Gly Val Ser Val
130                 135                 140

Val Met Gly Ile Pro Ser Val Arg Arg Glu Val His Ser Tyr Leu Thr
145                 150                 155                 160

Asp Thr Leu His Ser Leu Ile Ser Glu Leu Ser Pro Gln Glu Lys Glu
                165                 170                 175

Asp Ser Val Ile Val Val Leu Ile Ala Glu Thr Asp Ser Gln Tyr Thr
            180                 185                 190

Ser Ala Val Thr Glu Asn Ile Lys Ala Leu Phe Pro Thr Glu Ile His
        195                 200                 205

Ser Gly Leu Leu Glu Val Ile Ser Pro Ser Pro His Phe Tyr Pro Asp
210                 215                 220

Phe Ser Arg Leu Arg Glu Ser Phe Gly Asp Pro Lys Glu Arg Val Arg
225                 230                 235                 240

Trp Arg Thr Lys Gln Asn Leu Asp Tyr Cys Phe Leu Met Met Tyr Ala
                245                 250                 255

Gln Ser Lys Gly Ile Tyr Tyr Val Gln Leu Glu Asp Asp Ile Val Ala
            260                 265                 270

Lys Pro Asn Tyr Leu Ser Thr Met Lys Asn Phe Ala Leu Gln Gln Pro
        275                 280                 285

Ser Glu Asp Trp Met Ile Leu Glu Phe Ser Gln Leu Gly Phe Ile Gly
290                 295                 300

Lys Met Phe Lys Ser Leu Asp Leu Ser Leu Ile Val Glu Phe Ile Leu
305                 310                 315                 320

Met Phe Tyr Arg Asp Lys Pro Ile Asp Trp Leu Leu Asp His Ile Leu
                325                 330                 335

Trp Val Lys Val Cys Asn Pro Glu Lys Asp Ala Lys His Cys Asp Arg
            340                 345                 350
```

```
Gln Lys Ala Asn Leu Arg Ile Arg Phe Lys Pro Ser Leu Phe Gln His
        355                 360                 365

Val Gly Thr His Ser Ser Leu Ala Gly Lys Ile Gln Lys Leu Lys Asp
    370                 375                 380

Lys Asp Phe Gly Lys Gln Ala Leu Arg Lys Glu His Val Asn Pro Pro
385                 390                 395                 400

Ala Glu Val Ser Thr Ser Leu Lys Thr Tyr Gln His Phe Thr Leu Glu
                405                 410                 415

Lys Ala Tyr Leu Arg Glu Asp Phe Phe Trp Ala Phe Thr Pro Ala Ala
            420                 425                 430

Gly Asp Phe Ile Arg Phe Arg Phe Phe Gln Pro Leu Arg Leu Glu Arg
        435                 440                 445

Phe Phe Phe Arg Ser Gly Asn Ile Glu His Pro Glu Asp Lys Leu Phe
    450                 455                 460

Asn Thr Ser Val Glu Val Leu Pro Phe Asp Asn Pro Gln Ser Asp Lys
465                 470                 475                 480

Glu Ala Leu Gln Glu Gly Arg Thr Ala Thr Leu Arg Tyr Pro Arg Ser
                485                 490                 495

Pro Asp Gly Tyr Leu Gln Ile Gly Ser Phe Tyr Lys Gly Val Ala Glu
            500                 505                 510

Gly Glu Val Asp Pro Ala Phe Gly Pro Leu Glu Ala Leu Arg Leu Ser
        515                 520                 525

Ile Gln Thr Asp Ser Pro Val Trp Val Ile Leu Ser Glu Ile Phe Leu
    530                 535                 540

Lys Lys Ala Asp
545

<210> SEQ ID NO 29
<211> LENGTH: 563
<212> TYPE: PRT
<213> ORGANISM: Homo sapiens

<400> SEQUENCE: 29

Met Ser Arg Val Ala Gly Thr Arg Thr Asp Val Asn Glu Leu Leu Gln
1               5                   10                  15

Arg Trp Thr Pro Arg Cys Val Arg Trp His Thr Gly Gly Ala Arg Arg
            20                  25                  30

Val Ala Leu Asp Arg Pro Leu Val Thr Ala Cys Leu Pro Pro Ala Gly
        35                  40                  45

Asp Val Val Asp Val Tyr Gln Arg Glu Phe Leu Ala Leu Arg Asp Arg
    50                  55                  60

Leu His Ala Ala Glu Gln Glu Ser Leu Lys Arg Ser Lys Glu Leu Asn
65                  70                  75                  80

Leu Val Leu Asp Glu Ile Lys Arg Ala Val Ser Glu Arg Gln Ala Leu
                85                  90                  95

Arg Asp Gly Asp Gly Asn Arg Thr Trp Gly Arg Leu Thr Glu Asp Pro
            100                 105                 110

Arg Leu Lys Pro Trp Asn Gly Ser His Arg His Val Leu His Leu Pro
        115                 120                 125

Thr Val Phe His His Leu Pro His Leu Leu Ala Lys Glu Ser Ser Leu
    130                 135                 140

Gln Pro Ala Val Arg Val Gly Gln Gly Arg Thr Gly Val Ser Val Val
145                 150                 155                 160

Met Gly Ile Pro Ser Val Arg Glu Val His Ser Tyr Leu Thr Asp
                165                 170                 175
```

```
Thr Leu His Ser Leu Ile Ser Glu Leu Ser Pro Gln Glu Lys Glu Asp
            180                 185                 190

Ser Val Ile Val Val Leu Ile Ala Glu Thr Asp Ser Gln Tyr Thr Ser
        195                 200                 205

Ala Val Thr Glu Asn Ile Lys Ala Leu Phe Pro Thr Glu Ile His Ser
    210                 215                 220

Gly Leu Leu Glu Val Ile Ser Pro Ser Pro His Phe Tyr Pro Asp Phe
225                 230                 235                 240

Ser Arg Leu Arg Glu Ser Phe Gly Asp Pro Lys Glu Arg Val Arg Trp
                245                 250                 255

Arg Thr Lys Gln Asn Leu Asp Tyr Cys Phe Leu Met Met Tyr Ala Gln
            260                 265                 270

Ser Lys Gly Ile Tyr Tyr Val Gln Leu Glu Asp Asp Ile Val Ala Lys
        275                 280                 285

Pro Asn Tyr Leu Ser Thr Met Lys Asn Phe Ala Leu Gln Gln Pro Ser
    290                 295                 300

Glu Asp Trp Met Ile Leu Glu Phe Ser Gln Leu Gly Phe Ile Gly Lys
305                 310                 315                 320

Met Phe Lys Ser Leu Asp Leu Ser Leu Ile Val Glu Phe Ile Leu Met
                325                 330                 335

Phe Tyr Arg Asp Lys Pro Ile Asp Trp Leu Leu Asp His Ile Leu Trp
            340                 345                 350

Val Lys Val Cys Asn Pro Glu Lys Asp Ala Lys His Cys Asp Arg Gln
        355                 360                 365

Lys Ala Asn Leu Arg Ile Arg Phe Lys Pro Ser Leu Phe Gln His Val
    370                 375                 380

Gly Thr His Ser Ser Leu Ala Gly Lys Ile Gln Lys Leu Lys Asp Lys
385                 390                 395                 400

Asp Phe Gly Lys Gln Ala Leu Arg Lys Glu His Val Asn Pro Pro Ala
                405                 410                 415

Glu Val Ser Thr Ser Leu Lys Thr Tyr Gln His Phe Thr Leu Glu Lys
            420                 425                 430

Ala Tyr Leu Arg Glu Asp Phe Phe Trp Ala Phe Thr Pro Ala Ala Gly
        435                 440                 445

Asp Phe Ile Arg Phe Arg Phe Gln Pro Leu Arg Leu Glu Arg Phe
    450                 455                 460

Phe Phe Arg Ser Gly Asn Ile Glu His Pro Glu Asp Lys Leu Phe Asn
465                 470                 475                 480

Thr Ser Val Glu Val Leu Pro Phe Asp Asn Pro Gln Ser Asp Lys Glu
                485                 490                 495

Ala Leu Gln Glu Gly Arg Thr Ala Thr Leu Arg Tyr Pro Arg Ser Pro
            500                 505                 510

Asp Gly Tyr Leu Gln Ile Gly Ser Phe Tyr Lys Gly Val Ala Glu Gly
        515                 520                 525

Glu Val Asp Pro Ala Phe Gly Pro Leu Glu Ala Leu Arg Leu Ser Ile
    530                 535                 540

Gln Thr Asp Ser Pro Val Trp Val Ile Leu Ser Glu Ile Phe Leu Lys
545                 550                 555                 560

Lys Ala Asp

<210> SEQ ID NO 30
<211> LENGTH: 478
<212> TYPE: PRT
<213> ORGANISM: Homo sapiens
```

-continued

<400> SEQUENCE: 30

```
Met Phe Lys Phe His Gln Met Lys His Ile Phe Glu Ile Leu Asp Lys
1               5                   10                  15

Met Arg Cys Leu Arg Lys Arg Ser Thr Val Ser Phe Leu Gly Val Leu
            20                  25                  30

Val Ile Phe Leu Leu Phe Met Asn Leu Tyr Ile Glu Asp Ser Tyr Val
        35                  40                  45

Leu Glu Gly Asp Lys Gln Leu Ile Arg Glu Thr Ser Thr His Gln Leu
    50                  55                  60

Asn Ser Glu Arg Tyr Val His Thr Phe Lys Asp Leu Ser Asn Phe Ser
65                  70                  75                  80

Gly Ala Ile Asn Val Thr Tyr Arg Tyr Leu Ala Ala Thr Pro Leu Gln
                85                  90                  95

Arg Lys Arg Tyr Leu Thr Ile Gly Leu Ser Ser Val Lys Arg Lys Lys
            100                 105                 110

Gly Asn Tyr Leu Leu Glu Thr Ile Lys Ser Ile Phe Glu Gln Ser Ser
        115                 120                 125

Tyr Glu Glu Leu Lys Glu Ile Ser Val Val His Leu Ala Asp Phe
    130                 135                 140

Asn Ser Ser Trp Arg Asp Ala Met Val Gln Asp Ile Thr Gln Lys Phe
145                 150                 155                 160

Ala His His Ile Ile Ala Gly Arg Leu Met Val Ile His Ala Pro Glu
                165                 170                 175

Glu Tyr Tyr Pro Ile Leu Asp Gly Leu Lys Arg Asn Tyr Asn Asp Pro
            180                 185                 190

Glu Asp Arg Val Lys Phe Arg Ser Lys Gln Asn Val Asp Tyr Ala Phe
        195                 200                 205

Leu Leu Asn Phe Cys Ala Asn Thr Ser Asp Tyr Tyr Val Met Leu Glu
    210                 215                 220

Asp Asp Val Arg Cys Ser Lys Asn Phe Leu Thr Ala Ile Lys Lys Val
225                 230                 235                 240

Ile Ala Ser Leu Glu Gly Thr Tyr Trp Val Thr Leu Glu Phe Ser Lys
                245                 250                 255

Leu Gly Tyr Ile Gly Lys Leu Tyr His Ser His Asp Leu Pro Arg Leu
            260                 265                 270

Ala His Phe Leu Leu Met Phe Tyr Gln Glu Met Pro Cys Asp Trp Leu
        275                 280                 285

Leu Thr His Phe Arg Gly Leu Leu Ala Gln Lys Asn Val Ile Arg Phe
    290                 295                 300

Lys Pro Ser Leu Phe Gln His Met Gly Tyr Tyr Ser Ser Tyr Lys Gly
305                 310                 315                 320

Thr Glu Asn Lys Leu Lys Asp Asp Phe Glu Glu Ser Phe Asp
                325                 330                 335

Ile Pro Asp Asn Pro Pro Ala Ser Leu Tyr Thr Asn Met Asn Val Phe
            340                 345                 350

Glu Asn Tyr Glu Ala Ser Lys Ala Tyr Ser Ser Val Asp Glu Tyr Phe
        355                 360                 365

Trp Gly Lys Pro Pro Ser Thr Gly Asp Val Phe Val Ile Val Phe Glu
    370                 375                 380

Asn Pro Ile Ile Ile Lys Lys Ile Lys Val Asn Thr Gly Thr Glu Asp
385                 390                 395                 400

Arg Gln Asn Asp Ile Leu His His Gly Ala Leu Asp Val Gly Glu Asn
                405                 410                 415
```

-continued

Val Met Pro Ser Lys Gln Arg Arg Gln Cys Ser Thr Tyr Leu Arg Leu
                420                 425                 430

Gly Glu Phe Lys Asn Gly Asn Phe Glu Met Ser Gly Val Asn Gln Lys
            435                 440                 445

Ile Pro Phe Asp Ile His Cys Met Arg Ile Tyr Val Thr Lys Thr Gln
450                 455                 460

Lys Glu Trp Leu Ile Ile Arg Ser Ile Ser Ile Trp Thr Ser
465                 470                 475

<210> SEQ ID NO 31
<211> LENGTH: 740
<212> TYPE: PRT
<213> ORGANISM: Mus musculus

<400> SEQUENCE: 31

Met Ala Phe Phe Ser Pro Trp Lys Leu Ser Gln Lys Leu Gly Phe
1               5                   10                  15

Phe Leu Val Thr Phe Gly Phe Ile Trp Gly Met Met Leu Leu His Phe
            20                  25                  30

Thr Ile Gln Gln Arg Thr Gln Pro Glu Ser Ser Ser Met Leu Arg Glu
        35                  40                  45

Gln Ile Leu Asp Leu Ser Lys Arg Tyr Ile Lys Ala Leu Ala Glu Glu
    50                  55                  60

Asn Arg Asp Val Val Asp Gly Pro Tyr Ala Gly Val Met Thr Ala Tyr
65                  70                  75                  80

Asp Leu Lys Lys Thr Leu Ala Val Leu Leu Asp Asn Ile Leu Gln Arg
                85                  90                  95

Ile Gly Lys Leu Glu Ser Lys Val Asp Asn Leu Val Asn Gly Thr Gly
            100                 105                 110

Ala Asn Ser Thr Asn Ser Thr Thr Ala Val Pro Ser Leu Val Ser Leu
        115                 120                 125

Glu Lys Ile Asn Val Ala Asp Ile Ile Asn Gly Val Gln Glu Lys Cys
    130                 135                 140

Val Leu Pro Pro Met Asp Gly Tyr Pro His Cys Glu Gly Lys Ile Lys
145                 150                 155                 160

Trp Met Lys Asp Met Trp Arg Ser Asp Pro Cys Tyr Ala Asp Tyr Gly
                165                 170                 175

Val Asp Gly Thr Ser Cys Ser Phe Phe Ile Tyr Leu Ser Glu Val Glu
            180                 185                 190

Asn Trp Cys Pro Arg Leu Pro Trp Arg Ala Lys Asn Pro Tyr Glu Glu
        195                 200                 205

Ala Asp His Asn Ser Leu Ala Glu Ile Arg Thr Asp Phe Asn Ile Leu
    210                 215                 220

Tyr Gly Met Met Lys Lys His Glu Glu Phe Arg Trp Met Arg Leu Arg
225                 230                 235                 240

Ile Arg Arg Met Ala Asp Ala Trp Ile Gln Ala Ile Lys Ser Leu Ala
                245                 250                 255

Glu Lys Gln Asn Leu Glu Lys Arg Lys Arg Lys Lys Ile Leu Val His
            260                 265                 270

Leu Gly Leu Leu Thr Lys Glu Ser Gly Phe Lys Ile Ala Glu Thr Ala
        275                 280                 285

Phe Ser Gly Gly Pro Leu Gly Glu Leu Val Gln Trp Ser Asp Leu Ile
    290                 295                 300

Thr Ser Leu Tyr Leu Leu Gly His Asp Ile Arg Ile Ser Ala Ser Leu
305                 310                 315                 320

-continued

```
Ala Glu Leu Lys Glu Ile Met Lys Lys Val Gly Asn Arg Ser Gly
            325                 330                 335

Cys Pro Thr Val Gly Asp Arg Ile Val Glu Leu Ile Tyr Ile Asp Ile
            340                 345                 350

Val Gly Leu Ala Gln Phe Lys Lys Thr Leu Gly Pro Ser Trp Val His
            355                 360                 365

Tyr Gln Cys Met Leu Arg Val Leu Asp Ser Phe Gly Thr Glu Pro Glu
    370                 375                 380

Phe Asn His Ala Ser Tyr Ala Gln Ser Lys Gly His Lys Thr Pro Trp
385                 390                 395                 400

Gly Lys Trp Asn Leu Asn Pro Gln Gln Phe Tyr Thr Met Phe Pro His
                405                 410                 415

Thr Pro Asp Asn Ser Phe Leu Gly Phe Val Val Glu Gln His Leu Asn
                420                 425                 430

Ser Ser Asp Ile His His Ile Asn Glu Ile Lys Arg Gln Asn Gln Ser
                435                 440                 445

Leu Val Tyr Gly Lys Val Asp Ser Phe Trp Lys Asn Lys Lys Ile Tyr
    450                 455                 460

Leu Asp Ile Ile His Thr Tyr Met Glu Val His Ala Thr Val Tyr Gly
465                 470                 475                 480

Ser Ser Thr Lys Asn Ile Pro Ser Tyr Val Lys Asn His Gly Ile Leu
                485                 490                 495

Ser Gly Arg Asp Leu Gln Phe Leu Leu Arg Glu Thr Lys Leu Phe Val
                500                 505                 510

Gly Leu Gly Phe Pro Tyr Glu Gly Pro Ala Pro Leu Glu Ala Ile Ala
            515                 520                 525

Asn Gly Cys Ala Phe Leu Asn Pro Lys Phe Asn Pro Pro Lys Ser Ser
            530                 535                 540

Lys Asn Thr Asp Phe Phe Ile Gly Lys Pro Thr Leu Arg Glu Leu Thr
545                 550                 555                 560

Ser Gln His Pro Tyr Ala Glu Val Phe Ile Gly Arg Pro His Val Trp
                565                 570                 575

Thr Val Asp Leu Asn Asn Arg Glu Glu Val Glu Asp Ala Val Lys Ala
                580                 585                 590

Ile Leu Asn Gln Lys Ile Glu Pro Tyr Met Pro Tyr Glu Phe Thr Cys
                595                 600                 605

Glu Gly Met Leu Gln Arg Ile Asn Ala Phe Ile Glu Lys Gln Asp Phe
    610                 615                 620

Cys His Gly Gln Val Met Trp Pro Pro Leu Ser Ala Leu Gln Val Lys
625                 630                 635                 640

Leu Ala Glu Pro Gly Gln Ser Cys Lys Gln Val Cys Gln Glu Ser Gln
                645                 650                 655

Leu Ile Cys Glu Pro Ser Phe Phe Gln His Leu Asn Lys Glu Lys Asp
                660                 665                 670

Leu Leu Lys Tyr Lys Val Thr Cys Gln Ser Ser Glu Leu Tyr Lys Asp
            675                 680                 685

Ile Leu Val Pro Ser Phe Tyr Pro Lys Ser Lys His Cys Val Phe Gln
            690                 695                 700

Gly Asp Leu Leu Leu Phe Ser Cys Ala Gly Ala His Pro Thr His Gln
705                 710                 715                 720

Arg Ile Cys Pro Cys Arg Asp Phe Ile Lys Gly Gln Val Ala Leu Cys
                725                 730                 735

Lys Asp Cys Leu
            740
```

<210> SEQ ID NO 32
<211> LENGTH: 792
<212> TYPE: PRT
<213> ORGANISM: Mus musculus

<400> SEQUENCE: 32

Met Ile Thr Val Asn Pro Asp Gly Lys Ile Met Val Arg Arg Cys Leu
1               5                   10                  15

Val Thr Leu Arg Pro Phe Arg Leu Phe Val Leu Gly Ile Gly Phe Phe
            20                  25                  30

Thr Leu Cys Phe Leu Met Thr Ser Leu Gly Gly Gln Phe Ser Ala Arg
        35                  40                  45

Arg Leu Gly Asp Ser Pro Phe Thr Ile Arg Thr Glu Val Pro Gly Ser
    50                  55                  60

Pro Glu Ser Arg Gly Ala Leu Arg Lys Met Ser Asp Leu Leu Glu Leu
65                  70                  75                  80

Met Val Lys Arg Met Asp Met Leu Ala Arg Leu Glu Asn Ser Ser Glu
                85                  90                  95

Leu His Arg Thr Ala Ser Val Ala His Leu Ala Ala Asp Arg Leu Thr
            100                 105                 110

Pro Gly Ala Ser Leu Ile Glu Arg Ile Gln Ala Ile Ala Gln Asn Val
        115                 120                 125

Ser Asp Ile Ala Val Lys Val Asp Gln Ile Leu Arg His Ser Leu Ile
    130                 135                 140

Leu His Ser Lys Val Ser Glu Gly Arg Arg Asp Gln Cys Glu Ala Pro
145                 150                 155                 160

Ser Asp Pro Lys Phe Pro Asp Cys Ser Gly Lys Val Glu Trp Met Arg
                165                 170                 175

Ala Arg Trp Thr Ser Asp Pro Cys Tyr Ala Phe Phe Gly Val Asp Gly
            180                 185                 190

Thr Glu Cys Ser Phe Leu Ile Tyr Leu Ser Glu Val Glu Trp Phe Cys
        195                 200                 205

Pro Pro Leu Pro Trp Arg Asn Gln Thr Ala Ala Arg Thr Ala Pro Lys
    210                 215                 220

Ser Leu Pro Arg Val Gln Ala Val Phe Arg Ser Asn Leu Ser His Leu
225                 230                 235                 240

Leu Glu Leu Met Gly Ser Gly Lys Glu Ser Leu Ile Phe Met Lys Lys
                245                 250                 255

Arg Thr Arg Arg Phe Thr Ala Gln Trp Thr Lys Ala Ala Lys Tyr Leu
            260                 265                 270

Ala Gln Lys Leu Gly Asp Ile Arg Arg Asp Gln Lys Gln Ile Leu Val
        275                 280                 285

His Ile Gly Phe Leu Thr Glu Glu Ser Gly Asp Val Phe Ser Pro Arg
    290                 295                 300

Val Leu Lys Gly Gly Pro Leu Gly Glu Met Val Gln Trp Ala Asp Ile
305                 310                 315                 320

Leu Ala Ala Leu Tyr Val Leu Gly His Ser Leu Arg Ile Thr Val Ser
                325                 330                 335

Leu Lys Glu Leu Gln Ser Asn Leu Gly Val Pro Pro Gly Arg Gly Asn
            340                 345                 350

Cys Pro Leu Thr Val Pro Leu Pro Phe Asp Leu Ile Tyr Thr Asp Tyr
        355                 360                 365

His Gly Leu Gln Gln Met Lys Gln His Met Gly Leu Ser Phe Lys Lys
    370                 375                 380

```
Tyr Arg Cys Arg Ile Arg Val Ile Asp Thr Phe Gly Thr Glu Pro Ala
385                 390                 395                 400

Tyr Asn His Glu Glu Tyr Ala Thr Leu His Gly Tyr Arg Thr Asn Trp
                405                 410                 415

Gly Tyr Trp Asn Leu Asn Pro Lys Gln Phe Met Thr Met Phe Pro His
            420                 425                 430

Thr Pro Asp Asn Ser Phe Met Gly Phe Val Ser Glu Glu Leu Asn Glu
        435                 440                 445

Thr Glu Lys Gln Leu Ile Lys Asp Gly Lys Ala Ser Asn Met Ala Val
    450                 455                 460

Val Tyr Gly Lys Glu Ala Ser Ile Trp Lys Leu Gln Gly Lys Glu Lys
465                 470                 475                 480

Phe Leu Ala Val Leu Asn Lys Tyr Met Glu Ile His Gly Thr Val Tyr
                485                 490                 495

Tyr Glu Ser Gln Arg Pro Pro Glu Val Pro Ala Phe Val Lys Asn His
            500                 505                 510

Gly Leu Leu Pro Gln Pro Glu Phe Gln Gln Leu Leu Arg Lys Ala Lys
            515                 520                 525

Leu Phe Ile Gly Phe Gly Phe Pro Tyr Glu Gly Pro Ala Pro Leu Glu
        530                 535                 540

Ala Ile Ala Asn Gly Cys Ile Phe Leu Gln Ser Arg Phe Ser Pro Pro
545                 550                 555                 560

His Ser Ser Leu Asn His Glu Phe Phe Arg Gly Lys Pro Thr Ser Arg
                565                 570                 575

Glu Val Phe Ser Gln His Pro Tyr Ala Glu Asn Phe Ile Gly Lys Pro
            580                 585                 590

His Val Trp Thr Val Asp Tyr Asn Asn Ser Asp Glu Phe Glu Thr Ala
            595                 600                 605

Ile Lys Ala Ile Met Asn Thr Gln Val Asp Pro Tyr Leu Pro Tyr Glu
        610                 615                 620

Tyr Thr Cys Ala Gly Met Leu Glu Arg Ile Asn Ala Tyr Ile Gln His
625                 630                 635                 640

Gln Asp Phe Cys Val Gly Pro Ser Pro Leu Pro Pro Gly Ala Ser Thr
                645                 650                 655

Ala Gln Ser Pro Phe Val Leu Ala Pro Asn Ala Thr His Leu Glu Trp
            660                 665                 670

Ala Gln Asn Ile Ser Ser Val Pro Gly Ala Trp Pro Pro Thr His Ser
            675                 680                 685

Leu Arg Ala Trp Leu Ala Ala Pro Gly Arg Ala Cys Thr Asp Ala Cys
        690                 695                 700

Leu Asp His Gly Leu Ile Cys Glu Pro Ser Phe Pro Phe Leu Asn
705                 710                 715                 720

Ser Gln Asn Ser Phe Leu Lys Leu Gln Val Pro Cys Asp Ser Thr Glu
                725                 730                 735

Trp Glu Met His His Leu Tyr Pro Ala Phe Ala Gln Pro Gly Gln Glu
            740                 745                 750

Cys Tyr Leu Gln Lys Glu Pro Leu Leu Phe Ser Cys Ala Gly Ala Ser
            755                 760                 765

Thr Lys Tyr Gln Arg Leu Cys Pro Cys Arg Asp Phe Arg Lys Gly Gln
        770                 775                 780

Val Ala Leu Cys Gln Gly Cys Leu
785                 790
```

```
<210> SEQ ID NO 33
<211> LENGTH: 741
<212> TYPE: PRT
<213> ORGANISM: Homo sapiens

<400> SEQUENCE: 33

Met Ala Leu Phe Thr Pro Trp Lys Leu Ser Ser Gln Lys Leu Gly Phe
1               5                   10                  15

Phe Leu Val Thr Phe Gly Phe Ile Trp Gly Met Met Leu Leu His Phe
            20                  25                  30

Thr Ile Gln Gln Arg Thr Gln Pro Glu Ser Ser Met Leu Arg Glu
        35                  40                  45

Gln Ile Leu Asp Leu Ser Lys Arg Tyr Ile Lys Ala Leu Ala Glu Glu
    50                  55                  60

Asn Arg Asn Val Val Asp Gly Pro Tyr Ala Gly Val Met Thr Ala Tyr
65                  70                  75                  80

Asp Leu Lys Lys Thr Leu Ala Val Leu Leu Asp Asn Ile Leu Gln Arg
                85                  90                  95

Ile Gly Lys Leu Glu Ser Lys Val Asp Asn Leu Val Val Asn Gly Thr
            100                 105                 110

Gly Thr Asn Ser Thr Asn Ser Thr Ala Val Pro Ser Leu Val Ala
            115                 120                 125

Leu Glu Lys Ile Asn Val Ala Asp Ile Ile Asn Gly Ala Gln Glu Lys
130                 135                 140

Cys Val Leu Pro Pro Met Asp Gly Tyr Pro His Cys Glu Gly Lys Ile
145                 150                 155                 160

Lys Trp Met Lys Asp Met Trp Arg Ser Asp Pro Cys Tyr Ala Asp Tyr
                165                 170                 175

Gly Val Asp Gly Ser Thr Cys Ser Phe Phe Ile Tyr Leu Ser Glu Val
            180                 185                 190

Glu Asn Trp Cys Pro His Leu Pro Trp Arg Ala Lys Asn Pro Tyr Glu
            195                 200                 205

Glu Ala Asp His Asn Ser Leu Ala Glu Ile Arg Thr Asp Phe Asn Ile
    210                 215                 220

Leu Tyr Ser Met Met Lys Lys His Glu Glu Phe Arg Trp Met Arg Leu
225                 230                 235                 240

Arg Ile Arg Arg Met Ala Asp Ala Trp Ile Gln Ala Ile Lys Ser Leu
                245                 250                 255

Ala Glu Lys Gln Asn Leu Glu Lys Arg Lys Arg Lys Lys Val Leu Val
            260                 265                 270

His Leu Gly Leu Leu Thr Lys Glu Ser Gly Phe Lys Ile Ala Glu Thr
        275                 280                 285

Ala Phe Ser Gly Gly Pro Leu Gly Glu Leu Val Gln Trp Ser Asp Leu
    290                 295                 300

Ile Thr Ser Leu Tyr Leu Leu Gly His Asp Ile Arg Ile Ser Ala Ser
305                 310                 315                 320

Leu Ala Glu Leu Lys Glu Ile Met Lys Lys Val Val Gly Asn Arg Ser
                325                 330                 335

Gly Cys Pro Thr Val Gly Asp Arg Ile Val Glu Leu Ile Tyr Ile Asp
            340                 345                 350

Ile Val Gly Leu Ala Gln Phe Lys Lys Thr Leu Gly Pro Ser Trp Val
        355                 360                 365

His Tyr Gln Cys Met Leu Arg Val Leu Asp Ser Phe Gly Thr Glu Pro
    370                 375                 380

Glu Phe Asn His Ala Asn Tyr Ala Gln Ser Lys Gly His Lys Thr Pro
```

```
                385                 390                 395                 400
Trp Gly Lys Trp Asn Leu Asn Pro Gln Gln Phe Tyr Thr Met Phe Pro
                405                 410                 415

His Thr Pro Asp Asn Ser Phe Leu Gly Phe Val Val Glu Gln His Leu
            420                 425                 430

Asn Ser Ser Asp Ile His His Ile Asn Glu Ile Lys Arg Gln Asn Gln
        435                 440                 445

Ser Leu Val Tyr Gly Lys Val Asp Ser Phe Trp Lys Asn Lys Lys Ile
    450                 455                 460

Tyr Leu Asp Ile Ile His Thr Tyr Met Glu Val His Ala Thr Val Tyr
465                 470                 475                 480

Gly Ser Ser Thr Lys Asn Ile Pro Ser Tyr Val Lys Asn His Gly Ile
                485                 490                 495

Leu Ser Gly Arg Asp Leu Gln Phe Leu Leu Arg Glu Thr Lys Leu Phe
            500                 505                 510

Val Gly Leu Gly Phe Pro Tyr Glu Gly Pro Ala Pro Leu Glu Ala Ile
        515                 520                 525

Ala Asn Gly Cys Ala Phe Leu Asn Pro Lys Phe Asn Pro Pro Lys Ser
    530                 535                 540

Ser Lys Asn Thr Asp Phe Phe Ile Gly Lys Pro Thr Leu Arg Glu Leu
545                 550                 555                 560

Thr Ser Gln His Pro Tyr Ala Glu Val Phe Ile Gly Arg Pro His Val
                565                 570                 575

Trp Thr Val Asp Leu Asn Asn Gln Glu Glu Val Glu Asp Ala Val Lys
            580                 585                 590

Ala Ile Leu Asn Gln Lys Ile Glu Pro Tyr Met Pro Tyr Glu Phe Thr
        595                 600                 605

Cys Glu Gly Met Leu Gln Arg Ile Asn Ala Phe Ile Glu Lys Gln Asp
    610                 615                 620

Phe Cys His Gly Gln Val Met Trp Pro Leu Ser Ala Leu Gln Val
625                 630                 635                 640

Lys Leu Ala Glu Pro Gly Gln Ser Cys Lys Gln Val Cys Gln Glu Ser
                645                 650                 655

Gln Leu Ile Cys Glu Pro Ser Phe Phe Gln His Leu Asn Lys Asp Lys
            660                 665                 670

Asp Met Leu Lys Tyr Lys Val Thr Cys Gln Ser Ser Glu Leu Ala Lys
        675                 680                 685

Asp Ile Leu Val Pro Ser Phe Asp Pro Lys Asn Lys His Cys Val Phe
    690                 695                 700

Gln Gly Asp Leu Leu Leu Phe Ser Cys Ala Gly Ala His Pro Arg His
705                 710                 715                 720

Gln Arg Val Cys Pro Cys Arg Asp Phe Ile Lys Gly Gln Val Ala Leu
                725                 730                 735

Cys Lys Asp Cys Leu
            740

<210> SEQ ID NO 34
<211> LENGTH: 790
<212> TYPE: PRT
<213> ORGANISM: Homo sapiens

<400> SEQUENCE: 34

Met Ile Thr Val Asn Pro Asp Gly Lys Ile Met Val Arg Arg Cys Leu
1               5                   10                  15

Val Thr Leu Arg Pro Phe Arg Leu Phe Val Leu Gly Ile Gly Phe Phe
```

```
                    20                  25                  30
Thr Leu Cys Phe Leu Met Thr Ser Leu Gly Gly Gln Phe Ser Ala Arg
                35                  40                  45
Arg Leu Gly Asp Ser Pro Phe Thr Ile Arg Thr Glu Val Met Gly Gly
            50                  55                  60
Pro Glu Ser Arg Gly Val Leu Arg Lys Met Ser Asp Leu Leu Glu Leu
65                  70                  75                  80
Met Val Lys Arg Met Asp Ala Leu Ala Arg Leu Glu Asn Ser Ser Glu
                85                  90                  95
Leu His Arg Ala Gly Gly Asp Leu His Phe Pro Ala Asp Arg Met Pro
            100                 105                 110
Pro Gly Ala Gly Leu Met Glu Arg Ile Gln Ala Ile Ala Gln Asn Val
            115                 120                 125
Ser Asp Ile Ala Val Lys Val Asp Gln Ile Leu Arg His Ser Leu Leu
            130                 135                 140
Leu His Ser Lys Val Ser Glu Gly Arg Arg Asp Gln Cys Glu Ala Pro
145                 150                 155                 160
Ser Asp Pro Lys Phe Pro Asp Cys Ser Gly Lys Val Glu Trp Met Arg
                165                 170                 175
Ala Arg Trp Thr Ser Asp Pro Cys Tyr Ala Phe Phe Gly Val Asp Gly
            180                 185                 190
Thr Glu Cys Ser Phe Leu Ile Tyr Leu Ser Glu Val Glu Trp Phe Cys
            195                 200                 205
Pro Pro Leu Pro Trp Arg Asn Gln Thr Ala Ala Gln Arg Ala Pro Lys
            210                 215                 220
Pro Leu Pro Lys Val Gln Ala Val Phe Arg Ser Asn Leu Ser His Leu
225                 230                 235                 240
Leu Asp Leu Met Gly Ser Gly Lys Glu Ser Leu Ile Phe Met Lys Lys
                245                 250                 255
Arg Thr Lys Arg Leu Thr Ala Gln Trp Ala Leu Ala Ala Gln Arg Leu
                260                 265                 270
Ala Gln Lys Leu Gly Ala Thr Gln Arg Asp Gln Lys Gln Ile Leu Val
            275                 280                 285
His Ile Gly Phe Leu Thr Glu Glu Ser Gly Asp Val Phe Ser Pro Arg
            290                 295                 300
Val Leu Lys Gly Gly Pro Leu Gly Glu Met Val Gln Trp Ala Asp Ile
305                 310                 315                 320
Leu Thr Ala Leu Tyr Val Leu Gly His Gly Leu Arg Val Thr Val Ser
                325                 330                 335
Leu Lys Glu Leu Gln Ser Asn Leu Gly Val Pro Pro Gly Arg Gly Ser
                340                 345                 350
Cys Pro Leu Thr Met Pro Leu Pro Phe Asp Leu Ile Tyr Thr Asp Tyr
            355                 360                 365
His Gly Leu Gln Gln Met Lys His Met Gly Leu Ser Phe Lys Lys
            370                 375                 380
Tyr Arg Cys Arg Ile Arg Val Ile Asp Thr Phe Gly Thr Glu Pro Ala
385                 390                 395                 400
Tyr Asn His Glu Glu Tyr Ala Thr Leu His Gly Tyr Arg Thr Asn Trp
                405                 410                 415
Gly Tyr Trp Asn Leu Asn Pro Lys Gln Phe Met Thr Met Phe Pro His
            420                 425                 430
Thr Pro Asp Asn Ser Phe Met Gly Phe Val Ser Glu Glu Leu Asn Glu
            435                 440                 445
```

```
Thr Glu Lys Arg Leu Ile Lys Gly Gly Lys Ala Ser Asn Met Ala Val
        450                 455                 460

Val Tyr Gly Lys Glu Ala Ser Ile Trp Lys Gly Lys Glu Lys Phe Leu
465                 470                 475                 480

Gly Ile Leu Asn Lys Tyr Met Glu Ile His Gly Thr Val Tyr Tyr Glu
                485                 490                 495

Ser Gln Arg Pro Pro Glu Val Pro Ala Phe Val Lys Asn His Gly Leu
            500                 505                 510

Leu Pro Gln Pro Glu Phe Gln Gln Leu Leu Arg Lys Ala Lys Leu Phe
        515                 520                 525

Ile Gly Phe Gly Phe Pro Tyr Glu Gly Pro Ala Pro Leu Glu Ala Ile
    530                 535                 540

Ala Asn Gly Cys Ile Phe Leu Gln Ser Arg Phe Ser Pro Pro His Ser
545                 550                 555                 560

Ser Leu Asn His Glu Phe Phe Arg Gly Lys Pro Thr Ser Arg Glu Val
                565                 570                 575

Phe Ser Gln His Pro Tyr Ala Glu Asn Phe Ile Gly Lys Pro His Val
            580                 585                 590

Trp Thr Val Asp Tyr Asn Asn Ser Glu Glu Phe Glu Ala Ala Ile Lys
        595                 600                 605

Ala Ile Met Arg Thr Gln Val Asp Pro Tyr Leu Pro Tyr Glu Tyr Thr
    610                 615                 620

Cys Glu Gly Met Leu Glu Arg Ile His Ala Tyr Ile Gln His Gln Asp
625                 630                 635                 640

Phe Cys Arg Ala Pro Asp Pro Ala Leu Pro Glu Ala His Ala Pro Gln
                645                 650                 655

Ser Pro Phe Val Leu Ala Pro Asn Ala Thr His Leu Glu Trp Ala Arg
            660                 665                 670

Asn Thr Ser Leu Ala Pro Gly Ala Trp Pro Ala His Ala Leu Arg
        675                 680                 685

Ala Trp Leu Ala Val Pro Gly Arg Ala Cys Thr Asp Thr Cys Leu Asp
    690                 695                 700

His Gly Leu Ile Cys Glu Pro Ser Phe Phe Pro Phe Leu Asn Ser Gln
705                 710                 715                 720

Asp Ala Phe Leu Lys Leu Gln Val Pro Cys Asp Ser Thr Glu Ser Glu
                725                 730                 735

Met Asn His Leu Tyr Pro Ala Phe Ala Gln Pro Gly Gln Glu Cys Tyr
            740                 745                 750

Leu Gln Lys Glu Pro Leu Leu Phe Ser Cys Ala Gly Ser Asn Thr Lys
        755                 760                 765

Tyr Arg Arg Leu Cys Pro Cys Arg Asp Phe Arg Lys Gly Gln Val Ala
    770                 775                 780

Leu Cys Gln Gly Cys Leu
785                 790

<210> SEQ ID NO 35
<211> LENGTH: 801
<212> TYPE: PRT
<213> ORGANISM: Homo sapiens

<400> SEQUENCE: 35

Met His Ser Phe Val Lys His Leu Cys Ser Arg Tyr Val Val Glu Arg
1               5                   10                  15

Gln Gly Thr Met Ala Leu Pro Ala Leu Leu Thr Arg Leu Leu Pro Leu
            20                  25                  30
```

-continued

```
Arg Arg Leu Phe Val Leu Gly Ile Gly Phe Thr Leu Cys Phe Leu
        35                  40                  45

Met Thr Ser Leu Gly Gly Gln Phe Ser Ala Arg Arg Leu Gly Asp Ser
 50                  55                  60

Pro Phe Thr Ile Arg Thr Glu Val Met Gly Pro Glu Ser Arg Gly
 65                  70                  75                  80

Val Leu Arg Lys Met Ser Asp Leu Leu Glu Leu Met Val Lys Arg Met
                 85                  90                  95

Asp Ala Leu Ala Arg Leu Glu Asn Ser Ser Glu Leu His Arg Ala Gly
                100                 105                 110

Gly Asp Leu His Phe Pro Ala Asp Arg Met Pro Pro Gly Ala Gly Leu
                115                 120                 125

Met Glu Arg Ile Gln Ala Ile Ala Gln Asn Val Ser Asp Ile Ala Val
130                 135                 140

Lys Val Asp Gln Ile Leu Arg His Ser Leu Leu Leu His Ser Lys Val
145                 150                 155                 160

Ser Glu Gly Arg Arg Asp Gln Cys Glu Ala Pro Ser Asp Pro Lys Phe
                165                 170                 175

Pro Asp Cys Ser Gly Lys Val Glu Trp Met Arg Ala Arg Trp Thr Ser
                180                 185                 190

Asp Pro Cys Tyr Ala Phe Phe Gly Val Asp Gly Thr Glu Cys Ser Phe
                195                 200                 205

Leu Ile Tyr Leu Ser Glu Val Glu Trp Phe Cys Pro Pro Leu Pro Trp
210                 215                 220

Arg Asn Gln Thr Ala Ala Gln Arg Ala Pro Lys Pro Leu Pro Lys Val
225                 230                 235                 240

Gln Ala Val Phe Arg Ser Asn Leu Ser His Leu Leu Asp Leu Met Gly
                245                 250                 255

Ser Gly Lys Glu Ser Leu Ile Phe Met Lys Lys Arg Thr Lys Arg Leu
                260                 265                 270

Thr Ala Gln Trp Ala Leu Ala Ala Gln Arg Leu Ala Gln Lys Leu Gly
                275                 280                 285

Ala Thr Gln Arg Asp Gln Lys Gln Ile Leu Val His Ile Gly Phe Leu
290                 295                 300

Thr Glu Glu Ser Gly Asp Val Phe Ser Pro Arg Val Leu Lys Gly Gly
305                 310                 315                 320

Pro Leu Gly Glu Met Val Gln Trp Ala Asp Ile Leu Thr Ala Leu Tyr
                325                 330                 335

Val Leu Gly His Gly Leu Arg Val Thr Val Ser Leu Lys Glu Leu Gln
                340                 345                 350

Ser Asn Leu Gly Val Pro Pro Gly Arg Gly Ser Cys Pro Leu Thr Met
                355                 360                 365

Pro Leu Pro Phe Asp Leu Ile Tyr Thr Asp Tyr His Gly Leu Gln Gln
370                 375                 380

Met Lys Arg His Met Gly Leu Ser Phe Lys Lys Tyr Arg Cys Arg Ile
385                 390                 395                 400

Arg Val Ile Asp Thr Phe Gly Thr Glu Pro Ala Tyr Asn His Glu Glu
                405                 410                 415

Tyr Ala Thr Leu His Gly Tyr Arg Thr Asn Trp Gly Tyr Trp Asn Leu
                420                 425                 430

Asn Pro Lys Gln Phe Met Thr Met Phe Pro His Thr Pro Asp Asn Ser
                435                 440                 445

Phe Met Gly Phe Val Ser Glu Glu Leu Asn Glu Thr Glu Lys Arg Leu
450                 455                 460
```

Ile Lys Gly Gly Lys Ala Ser Asn Met Ala Val Val Tyr Lys Glu
465                 470                 475                 480

Ala Ser Ile Trp Lys Gly Lys Glu Lys Phe Leu Gly Ile Leu Asn Lys
            485                 490                 495

Tyr Met Glu Ile His Gly Thr Val Tyr Tyr Glu Ser Gln Arg Pro Pro
                500                 505                 510

Glu Val Pro Ala Phe Val Lys Asn His Gly Leu Leu Pro Gln Pro Glu
            515                 520                 525

Phe Gln Gln Leu Leu Arg Lys Ala Lys Leu Phe Ile Gly Phe Gly Phe
530                 535                 540

Pro Tyr Glu Gly Pro Ala Pro Leu Glu Ala Ile Ala Asn Gly Cys Ile
545                 550                 555                 560

Phe Leu Gln Ser Arg Phe Ser Pro Pro His Ser Ser Leu Asn His Glu
                565                 570                 575

Phe Phe Arg Gly Lys Pro Thr Ser Arg Glu Val Phe Ser Gln His Pro
            580                 585                 590

Tyr Ala Glu Asn Phe Ile Gly Lys Pro His Val Trp Thr Val Asp Tyr
                595                 600                 605

Asn Asn Ser Glu Glu Phe Glu Ala Ala Ile Lys Ala Ile Met Arg Thr
610                 615                 620

Gln Val Asp Pro Tyr Leu Pro Tyr Glu Tyr Thr Cys Glu Gly Met Leu
625                 630                 635                 640

Glu Arg Ile His Ala Tyr Ile Gln His Gln Asp Phe Cys Arg Ala Pro
                645                 650                 655

Asp Pro Ala Leu Pro Glu Ala His Ala Pro Gln Ser Pro Phe Val Leu
            660                 665                 670

Ala Pro Asn Ala Thr His Leu Glu Trp Ala Arg Asn Thr Ser Leu Ala
                675                 680                 685

Pro Gly Ala Trp Pro Pro Ala His Ala Leu Arg Ala Trp Leu Ala Val
690                 695                 700

Pro Gly Arg Ala Cys Thr Asp Thr Cys Leu Asp His Gly Leu Ile Cys
705                 710                 715                 720

Glu Pro Ser Phe Phe Pro Phe Leu Asn Ser Gln Asp Ala Phe Leu Lys
                725                 730                 735

Leu Gln Val Pro Cys Asp Ser Thr Glu Ser Glu Met Asn His Leu Tyr
            740                 745                 750

Pro Ala Phe Ala Gln Pro Gly Gln Glu Cys Tyr Leu Gln Lys Glu Pro
                755                 760                 765

Leu Leu Phe Ser Cys Ala Gly Ser Asn Thr Lys Tyr Arg Arg Leu Cys
770                 775                 780

Pro Cys Arg Asp Phe Arg Lys Gly Gln Val Ala Leu Cys Gln Gly Cys
785                 790                 795                 800

Leu

<210> SEQ ID NO 36
<211> LENGTH: 464
<212> TYPE: PRT
<213> ORGANISM: Gallus gallus

<400> SEQUENCE: 36

Met Arg Cys Ser Pro Lys Arg Ser Leu Thr Ala Val Ile Ala Ala Ser
1               5                   10                  15

Phe Leu Leu Leu Leu Leu Leu Leu Leu His Arg Gly Ser Trp Gln
            20                  25                  30

```
Asp Pro Gln Glu Val Gln Phe Arg Asp Leu Pro Ser Asp Ala Val Leu
    35                  40                  45

Lys Ile Leu Lys Gln Gly Ser Leu His Ile Leu Gln Asp Thr Asp Asn
50                  55                  60

Leu Cys Ala Leu His Asn Ile Ser Tyr His Leu Leu Ala Gly Ser Pro
65                  70                  75                  80

Leu Pro His Lys Lys Phe Leu Ala Val Gly Leu Ser Ser Val Arg Arg
                85                  90                  95

Pro Arg Gly Tyr Tyr Leu Pro Asp Thr Leu Gln Ser Leu Phe Lys Gln
            100                 105                 110

Ser Ser Glu Glu Glu Leu Gln Glu Met Val Val Val His Leu Ala
        115                 120                 125

Asp Ala Asp Pro Ile Trp Asn Ala Gln Val Ala Ala Asp Ile Ser His
    130                 135                 140

Arg Phe Ala His His Ile Leu Leu Gly Arg Leu Val Leu Ile His Thr
145                 150                 155                 160

Pro His Glu Phe Tyr Pro Thr Leu Glu Gly Leu Lys Arg Asn Tyr Asn
                165                 170                 175

Asp Pro Glu Glu Arg Val Lys Phe Arg Ser Lys Gln Asn Val Asp Tyr
            180                 185                 190

Ala Phe Leu Phe Thr Phe Ala Ala Asn Leu Ser Ser Tyr Tyr Leu Met
        195                 200                 205

Ile Glu Asp Asp Val Trp Ser Ala Lys Ser Phe Phe Thr Ala Ile Arg
    210                 215                 220

Lys Ala Val Ala Ser Gln Glu Gly Ser Asn Trp Ala Thr Leu Glu Phe
225                 230                 235                 240

Ser Lys Leu Gly Tyr Ile Gly Lys Leu Tyr Arg Ser Ser Asp Leu Pro
                245                 250                 255

Arg Leu Ala Arg Phe Leu Leu Leu Phe Tyr Gln Glu Met Pro Cys Asp
            260                 265                 270

Trp Leu Leu Thr His Phe Arg Leu Leu Thr Gln Lys Asp Val Ile
        275                 280                 285

Arg Phe Lys Pro Ser Leu Phe Gln His Met Gly Leu Tyr Ser Ser Phe
    290                 295                 300

Gln Gly Thr Val Asn Arg Leu Glu Asp Glu Phe Gln Ala Asp Ala
305                 310                 315                 320

Met Asp Leu Pro Asp Asn Pro Ala Ala Leu Phe Thr Asn Met Val
                325                 330                 335

Val Phe Glu Asn Tyr Glu Pro Ser Lys Ala Tyr Ser Thr Ala Arg Gly
            340                 345                 350

Tyr Phe Trp Gly Lys Asn Pro Ala Val Gly Ser Ile Phe Ser Ile Val
        355                 360                 365

Phe His Gln Pro Ala Arg Val Thr Arg Val Gln Thr Gly Ser
    370                 375                 380

Ser Glu Arg Pro Gly Asp Phe Leu His Ala Gly Val Leu Glu Leu Gly
385                 390                 395                 400

Arg Gly Arg Arg Ala Asp Gly Arg Asp Cys Ser Val Tyr Thr Thr Val
                405                 410                 415

Gly Thr Phe Glu Lys Gly Asn Leu Glu Trp Arg Gly Leu Glu Lys Gly
            420                 425                 430

Met Pro Asn Pro Val Glu Cys Val Arg Ile Arg Val Thr Gln Ser Gln
        435                 440                 445

Ser Glu Trp Leu Ile Ile Gln Ser Ile Gly Ile Trp Thr Ala Gly Thr
    450                 455                 460
```

<210> SEQ ID NO 37
<211> LENGTH: 1150
<212> TYPE: PRT
<213> ORGANISM: Mus musculus

<400> SEQUENCE: 37

```
Met Lys Leu Ser Arg Gln Phe Thr Val Phe Gly Ser Ala Ile Phe Cys
1               5                   10                  15

Val Val Ile Phe Ser Leu Tyr Leu Met Leu Asp Arg Gly His Leu Asp
            20                  25                  30

Tyr Pro Arg Gly Pro Arg Gln Glu Gly Ser Phe Pro Gln Gly Gln Leu
        35                  40                  45

Ser Ile Leu Gln Glu Lys Ile Asp His Leu Glu Arg Leu Leu Ala Glu
50                  55                  60

Asn Asn Glu Ile Ile Ser Asn Ile Arg Asp Ser Val Ile Asn Leu Ser
65                  70                  75                  80

Glu Ser Val Glu Asp Gly Pro Arg Gly Ser Pro Gly Asn Ala Ser Gln
                85                  90                  95

Gly Ser Ile His Leu His Ser Pro Gln Leu Ala Leu Gln Ala Asp Pro
            100                 105                 110

Arg Asp Cys Leu Phe Ala Ser Gln Ser Gly Ser Gln Pro Arg Asp Val
        115                 120                 125

Gln Met Leu Asp Val Tyr Asp Leu Ile Pro Phe Asp Asn Pro Asp Gly
130                 135                 140

Gly Val Trp Lys Gln Gly Phe Asp Ile Lys Tyr Glu Ala Asp Glu Trp
145                 150                 155                 160

Asp His Glu Pro Leu Gln Val Phe Val Val Pro His Ser His Asn Asp
                165                 170                 175

Pro Gly Trp Leu Lys Thr Phe Asn Asp Tyr Phe Arg Asp Lys Thr Gln
            180                 185                 190

Tyr Ile Phe Asn Asn Met Val Leu Lys Leu Lys Glu Asp Ser Ser Arg
        195                 200                 205

Lys Phe Met Trp Ser Glu Ile Ser Tyr Leu Ala Lys Trp Trp Asp Ile
210                 215                 220

Ile Asp Ile Pro Lys Lys Glu Ala Val Lys Ser Leu Leu Gln Asn Gly
225                 230                 235                 240

Gln Leu Glu Ile Val Thr Gly Gly Trp Val Met Pro Asp Glu Ala Thr
                245                 250                 255

Pro His Tyr Phe Ala Leu Ile Asp Gln Leu Ile Glu Gly His Gln Trp
            260                 265                 270

Leu Glu Lys Asn Leu Gly Val Lys Pro Arg Ser Gly Trp Ala Ile Asp
        275                 280                 285

Pro Phe Gly His Ser Pro Thr Met Ala Tyr Leu Leu Lys Arg Ala Gly
290                 295                 300

Phe Ser His Met Leu Ile Gln Arg Val His Tyr Ala Ile Lys Lys His
305                 310                 315                 320

Phe Ser Leu His Lys Thr Leu Glu Phe Phe Trp Arg Gln Asn Trp Asp
                325                 330                 335

Leu Gly Ser Ala Thr Asp Ile Leu Cys His Met Met Pro Phe Tyr Ser
            340                 345                 350

Tyr Asp Ile Pro His Thr Cys Gly Pro Asp Pro Lys Ile Cys Cys Gln
        355                 360                 365

Phe Asp Phe Lys Arg Leu Pro Gly Gly Arg Tyr Gly Cys Pro Trp Gly
370                 375                 380
```

-continued

```
Val Pro Pro Glu Ala Ile Ser Pro Gly Asn Val Gln Ser Arg Ala Gln
385                 390                 395                 400

Met Leu Leu Asp Gln Tyr Arg Lys Lys Ser Lys Leu Phe Arg Thr Lys
            405                 410                 415

Val Leu Leu Ala Pro Leu Gly Asp Asp Phe Arg Phe Ser Glu Tyr Thr
            420                 425                 430

Glu Trp Asp Leu Gln Cys Arg Asn Tyr Glu Gln Leu Phe Ser Tyr Met
        435                 440                 445

Asn Ser Gln Pro His Leu Lys Val Lys Ile Gln Phe Gly Thr Leu Ser
    450                 455                 460

Asp Tyr Phe Asp Ala Leu Glu Lys Ala Val Ala Ala Glu Lys Lys Ser
465                 470                 475                 480

Ser Gln Ser Val Phe Pro Ala Leu Ser Gly Asp Phe Thr Tyr Ala
            485                 490                 495

Asp Arg Asp Asp His Tyr Trp Ser Gly Tyr Phe Thr Ser Arg Pro Phe
            500                 505                 510

Tyr Lys Arg Met Asp Arg Ile Met Glu Ser Arg Ile Arg Ala Ala Glu
            515                 520                 525

Ile Leu Tyr Gln Leu Ala Leu Lys Gln Ala Gln Lys Tyr Lys Ile Asn
            530                 535                 540

Lys Phe Leu Ser Ser Pro His Tyr Thr Thr Leu Thr Glu Ala Arg Arg
545                 550                 555                 560

Asn Leu Gly Leu Phe Gln His His Asp Ala Ile Thr Gly Thr Ala Lys
            565                 570                 575

Asp Trp Val Val Asp Tyr Gly Thr Arg Leu Phe Gln Ser Leu Asn
            580                 585                 590

Ser Leu Glu Lys Ile Ile Gly Asp Ser Ala Phe Leu Leu Ile Leu Lys
            595                 600                 605

Asp Lys Lys Leu Tyr Gln Ser Asp Pro Ser Lys Ala Phe Leu Glu Met
            610                 615                 620

Asp Thr Lys Gln Ser Ser Gln Asp Ser Leu Pro Gln Lys Ile Ile Ile
625                 630                 635                 640

Gln Leu Ser Ala Gln Glu Pro Arg Tyr Leu Val Tyr Asn Pro Phe
            645                 650                 655

Glu Gln Glu Arg His Ser Val Val Ser Ile Arg Val Asn Ser Ala Thr
            660                 665                 670

Gly Lys Val Leu Ser Asp Ser Gly Lys Pro Val Glu Val Gln Val Ser
            675                 680                 685

Ala Val Trp Asn Asp Met Arg Thr Ile Ser Gln Ala Ala Tyr Glu Val
            690                 695                 700

Ser Phe Leu Ala His Ile Pro Pro Leu Gly Leu Lys Val Phe Lys Ile
705                 710                 715                 720

Leu Glu Ser Gln Ser Ser Ser His Leu Ala Asp Tyr Val Leu Tyr
            725                 730                 735

Asn Asn Asp Gly Leu Ala Glu Asn Gly Ile Phe His Val Lys Asn Met
            740                 745                 750

Val Asp Ala Gly Asp Ala Ile Thr Ile Glu Asn Pro Phe Leu Ala Ile
            755                 760                 765

Trp Phe Asp Arg Ser Gly Leu Met Glu Lys Val Arg Arg Lys Glu Asp
            770                 775                 780

Ser Arg Gln His Glu Leu Lys Val Gln Phe Leu Trp Tyr Gly Thr Thr
785                 790                 795                 800

Asn Lys Arg Asp Lys Ser Gly Ala Tyr Leu Phe Leu Pro Asp Gly Gln
```

```
                    805                 810                 815
Gly Gln Pro Tyr Val Ser Leu Arg Pro Pro Phe Val Arg Val Thr Arg
                820                 825                 830

Gly Arg Ile Tyr Ser Asp Val Thr Cys Phe Leu Glu His Val Thr His
            835                 840                 845

Lys Val Arg Leu Tyr Asn Ile Gln Gly Ile Glu Gly Gln Ser Met Glu
        850                 855                 860

Val Ser Asn Ile Val Asn Ile Arg Asn Val His Asn Arg Glu Ile Val
865                 870                 875                 880

Met Arg Ile Ser Ser Lys Ile Asn Asn Gln Asn Arg Tyr Tyr Thr Asp
                885                 890                 895

Leu Asn Gly Tyr Gln Ile Gln Pro Arg Arg Thr Met Ser Lys Leu Pro
            900                 905                 910

Leu Gln Ala Asn Val Tyr Pro Met Cys Thr Met Ala Tyr Ile Gln Asp
        915                 920                 925

Ala Glu His Arg Leu Thr Leu Leu Ser Ala Gln Ser Leu Gly Ala Ser
    930                 935                 940

Ser Met Ala Ser Gly Gln Ile Glu Val Phe Met Asp Arg Arg Leu Met
945                 950                 955                 960

Gln Asp Asp Asn Arg Gly Leu Gly Gln Gly Val His Asp Asn Lys Ile
                965                 970                 975

Thr Ala Asn Leu Phe Arg Ile Leu Leu Glu Lys Arg Ser Ala Val Asn
            980                 985                 990

Met Glu Glu Glu Lys Lys Ser Pro  Val Ser Tyr Pro Ser  Leu Leu Ser
        995                 1000                1005

His Met  Thr Ser Ser Phe Leu  Asn His Pro Phe Leu  Pro Met Val
    1010                1015                1020

Leu Ser  Gly Gln Leu Pro Ser  Pro Ala Phe Glu Leu  Leu Ser Glu
    1025                1030                1035

Phe Pro  Leu Leu Gln Ser Ser  Leu Pro Cys Asp Ile  His Leu Val
    1040                1045                1050

Asn Leu  Arg Thr Ile Gln Ser  Lys Met Gly Lys Gly  Tyr Ser Asp
    1055                1060                1065

Glu Ala  Ala Leu Ile Leu His  Arg Lys Gly Phe Asp  Cys Gln Phe
    1070                1075                1080

Ser Ser  Arg Gly Ile Gly Leu  Pro Cys Ser Thr Thr  Gln Gly Lys
    1085                1090                1095

Met Ser  Val Leu Lys Leu Phe  Asn Lys Phe Ala Val  Glu Ser Leu
    1100                1105                1110

Val Pro  Ser Ser Leu Ser Leu  Met His Ser Pro Pro  Asp Ala Gln
    1115                1120                1125

Asn Met  Ser Glu Val Ser Leu  Ser Pro Met Glu Ile  Ser Thr Phe
    1130                1135                1140

Arg Ile  Arg Leu Arg Trp Thr
    1145                1150

<210> SEQ ID NO 38
<211> LENGTH: 1144
<212> TYPE: PRT
<213> ORGANISM: Homo sapiens

<400> SEQUENCE: 38

Met Lys Leu Ser Arg Gln Phe Thr Val Phe Gly Ser Ala Ile Phe Cys
1               5                   10                  15

Val Val Ile Phe Ser Leu Tyr Leu Met Leu Asp Arg Gly His Leu Asp
```

-continued

```
                20                  25                  30
Tyr Pro Arg Asn Pro Arg Arg Glu Gly Ser Phe Pro Gln Gly Gln Leu
                35                  40                  45

Ser Met Leu Gln Glu Lys Ile Asp His Leu Glu Arg Leu Leu Ala Glu
    50                  55                  60

Asn Asn Glu Ile Ile Ser Asn Ile Arg Asp Ser Val Ile Asn Leu Ser
65                  70                  75                  80

Glu Ser Val Glu Asp Gly Pro Lys Ser Ser Gln Ser Asn Phe Ser Gln
                85                  90                  95

Gly Ala Gly Ser His Leu Leu Pro Ser Gln Leu Ser Leu Ser Val Asp
            100                 105                 110

Thr Ala Asp Cys Leu Phe Ala Ser Gln Ser Gly Ser His Asn Ser Asp
            115                 120                 125

Val Gln Met Leu Asp Val Tyr Ser Leu Ile Ser Phe Asp Asn Pro Asp
        130                 135                 140

Gly Gly Val Trp Lys Gln Gly Phe Asp Ile Thr Tyr Glu Ser Asn Glu
145                 150                 155                 160

Trp Asp Thr Glu Pro Leu Gln Val Phe Val Pro His Ser His Asn
            165                 170                 175

Asp Pro Gly Trp Leu Lys Thr Phe Asn Asp Tyr Phe Arg Asp Lys Thr
            180                 185                 190

Gln Tyr Ile Phe Asn Asn Met Val Leu Lys Leu Lys Glu Asp Ser Arg
        195                 200                 205

Arg Lys Phe Ile Trp Ser Glu Ile Ser Tyr Leu Ser Lys Trp Trp Asp
    210                 215                 220

Ile Ile Asp Ile Gln Lys Lys Asp Ala Val Lys Ser Leu Ile Glu Asn
225                 230                 235                 240

Gly Gln Leu Glu Ile Val Thr Gly Gly Trp Val Met Pro Asp Glu Ala
            245                 250                 255

Thr Pro His Tyr Phe Ala Leu Ile Asp Gln Leu Ile Glu Gly His Gln
            260                 265                 270

Trp Leu Glu Asn Asn Ile Gly Val Lys Pro Arg Ser Gly Trp Ala Ile
        275                 280                 285

Asp Pro Phe Gly His Ser Pro Thr Met Ala Tyr Leu Leu Asn Arg Ala
    290                 295                 300

Gly Leu Ser His Met Leu Ile Gln Arg Val His Tyr Ala Val Lys Lys
305                 310                 315                 320

His Phe Ala Leu His Lys Thr Leu Glu Phe Phe Trp Arg Gln Asn Trp
            325                 330                 335

Asp Leu Gly Ser Val Thr Asp Ile Leu Cys His Met Met Pro Phe Tyr
            340                 345                 350

Ser Tyr Asp Ile Pro His Thr Cys Gly Pro Asp Pro Lys Ile Cys Cys
        355                 360                 365

Gln Phe Asp Phe Lys Arg Leu Pro Gly Gly Arg Phe Gly Cys Pro Trp
    370                 375                 380

Gly Val Pro Pro Glu Thr Ile His Pro Gly Asn Val Gln Ser Arg Ala
385                 390                 395                 400

Arg Met Leu Leu Asp Gln Tyr Arg Lys Lys Ser Lys Leu Phe Arg Thr
            405                 410                 415

Lys Val Leu Leu Ala Pro Leu Gly Asp Asp Phe Arg Tyr Cys Glu Tyr
            420                 425                 430

Thr Glu Trp Asp Leu Gln Phe Lys Asn Tyr Gln Gln Leu Phe Asp Tyr
        435                 440                 445
```

```
Met Asn Ser Gln Ser Lys Phe Lys Val Lys Ile Gln Phe Gly Thr Leu
450                 455                 460
Ser Asp Phe Phe Asp Ala Leu Asp Lys Ala Asp Glu Thr Gln Arg Asp
465                 470                 475                 480
Lys Gly Gln Ser Met Phe Pro Val Leu Ser Gly Asp Phe Phe Thr Tyr
                    485                 490                 495
Ala Asp Arg Asp His Tyr Trp Ser Gly Tyr Phe Thr Ser Arg Pro
            500                 505                 510
Phe Tyr Lys Arg Met Asp Arg Ile Met Glu Ser His Leu Arg Ala Ala
        515                 520                 525
Glu Ile Leu Tyr Tyr Phe Ala Leu Arg Gln Ala His Lys Tyr Lys Ile
530                 535                 540
Asn Lys Phe Leu Ser Ser Ser Leu Tyr Thr Ala Leu Thr Glu Ala Arg
545                 550                 555                 560
Arg Asn Leu Gly Leu Phe Gln His His Asp Ala Ile Thr Gly Thr Ala
                565                 570                 575
Lys Asp Trp Val Val Asp Tyr Gly Thr Arg Leu Phe His Ser Leu
            580                 585                 590
Met Val Leu Glu Lys Ile Ile Gly Asn Ser Ala Phe Leu Leu Ile Leu
        595                 600                 605
Lys Asp Lys Leu Thr Tyr Asp Ser Tyr Ser Pro Asp Thr Phe Leu Glu
            610                 615                 620
Met Asp Leu Lys Gln Lys Ser Gln Asp Ser Leu Pro Gln Lys Asn Ile
625                 630                 635                 640
Ile Arg Leu Ser Ala Glu Pro Arg Tyr Leu Val Val Tyr Asn Pro Leu
                645                 650                 655
Glu Gln Asp Arg Ile Ser Leu Val Ser Val Tyr Val Ser Ser Pro Thr
            660                 665                 670
Val Gln Val Phe Ser Ala Ser Gly Lys Pro Val Glu Val Gln Val Ser
        675                 680                 685
Ala Val Trp Asp Thr Ala Asn Thr Ile Ser Glu Thr Ala Tyr Glu Ile
            690                 695                 700
Ser Phe Arg Ala His Ile Pro Pro Leu Gly Leu Lys Val Tyr Lys Ile
705                 710                 715                 720
Leu Glu Ser Ala Ser Ser Asn Ser His Leu Ala Asp Tyr Val Leu Tyr
                725                 730                 735
Lys Asn Lys Val Glu Asp Ser Gly Ile Phe Thr Ile Lys Asn Met Ile
            740                 745                 750
Asn Thr Glu Glu Gly Ile Thr Leu Glu Asn Ser Phe Val Leu Leu Arg
            755                 760                 765
Phe Asp Gln Thr Gly Leu Met Lys Gln Met Met Thr Lys Glu Asp Gly
770                 775                 780
Lys His His Glu Val Asn Val Gln Phe Ser Trp Tyr Gly Thr Thr Ile
785                 790                 795                 800
Lys Arg Asp Lys Ser Gly Ala Tyr Leu Phe Leu Pro Asp Gly Asn Ala
                805                 810                 815
Lys Pro Tyr Val Tyr Thr Thr Pro Pro Phe Val Arg Val Thr His Gly
            820                 825                 830
Arg Ile Tyr Ser Glu Val Thr Cys Phe Phe Asp His Val Thr His Arg
        835                 840                 845
Val Arg Leu Tyr His Ile Gln Gly Ile Glu Gly Gln Ser Val Glu Val
        850                 855                 860
Ser Asn Ile Val Asp Ile Arg Lys Val Tyr Asn Arg Glu Ile Ala Met
865                 870                 875                 880
```

```
Lys Ile Ser Ser Asp Ile Lys Ser Gln Asn Arg Phe Tyr Thr Asp Leu
                885                 890                 895

Asn Gly Tyr Gln Ile Gln Pro Arg Met Thr Leu Ser Lys Leu Pro Leu
            900                 905                 910

Gln Ala Asn Val Tyr Pro Met Thr Thr Met Ala Tyr Ile Gln Asp Ala
        915                 920                 925

Lys His Arg Leu Thr Leu Leu Ser Ala Gln Ser Leu Gly Val Ser Ser
    930                 935                 940

Leu Asn Ser Gly Gln Ile Glu Val Ile Met Asp Arg Arg Leu Met Gln
945                 950                 955                 960

Asp Asp Asn Arg Gly Leu Glu Gln Gly Ile Gln Asp Asn Lys Ile Thr
                965                 970                 975

Ala Asn Leu Phe Arg Ile Leu Leu Glu Lys Arg Ser Ala Val Asn Thr
            980                 985                 990

Glu Glu Glu Lys Lys Ser Val Ser Tyr Pro Ser Leu Leu Ser His Ile
        995                 1000                1005

Thr Ser Ser Leu Met Asn His Pro Val Ile Pro Met Ala Asn Lys
    1010                1015                1020

Phe Ser Ser Pro Thr Leu Glu Leu Gln Gly Glu Phe Ser Pro Leu
    1025                1030                1035

Gln Ser Ser Leu Pro Cys Asp Ile His Leu Val Asn Leu Arg Thr
    1040                1045                1050

Ile Gln Ser Lys Val Gly Asn Gly His Ser Asn Glu Ala Ala Leu
    1055                1060                1065

Ile Leu His Arg Lys Gly Phe Asp Cys Arg Phe Ser Ser Lys Gly
    1070                1075                1080

Thr Gly Leu Phe Cys Ser Thr Thr Gln Gly Lys Ile Leu Val Gln
    1085                1090                1095

Lys Leu Leu Asn Lys Phe Ile Val Glu Ser Leu Thr Pro Ser Ser
    1100                1105                1110

Leu Ser Leu Met His Ser Pro Pro Gly Thr Gln Asn Ile Ser Glu
    1115                1120                1125

Ile Asn Leu Ser Pro Met Glu Ile Ser Thr Phe Arg Ile Gln Leu
    1130                1135                1140

Arg

<210> SEQ ID NO 39
<211> LENGTH: 575
<212> TYPE: PRT
<213> ORGANISM: Mus musculus

<400> SEQUENCE: 39

Met Arg Ala Trp Thr Gly Ser Trp Arg Trp Ile Met Leu Ile Leu Phe
1               5                   10                  15

Ala Trp Gly Thr Leu Leu Phe Tyr Ile Gly Gly His Leu Val Arg Asp
            20                  25                  30

Asn Asp His Pro Asp His Ser Ser Arg Glu Leu Ser Lys Ile Leu Ala
        35                  40                  45

Lys Leu Glu Arg Leu Lys Gln Gln Asn Glu Asp Leu Arg Arg Met Ala
    50                  55                  60

Glu Ser Leu Arg Ile Pro Glu Gly Pro Ile Asp Gln Gly Thr Ala Thr
65                  70                  75                  80

Gly Arg Val Arg Val Leu Glu Glu Gln Leu Val Lys Ala Lys Glu Gln
                85                  90                  95
```

```
Ile Glu Asn Tyr Lys Lys Gln Ala Arg Asn Gly Leu Gly Lys Asp His
            100                 105                 110

Glu Ile Leu Arg Arg Ile Glu Asn Gly Ala Lys Glu Leu Trp Phe
        115                 120                 125

Phe Leu Gln Ser Glu Leu Lys Lys Leu Lys His Leu Glu Gly Asn Glu
130                 135                 140

Leu Gln Arg His Ala Asp Glu Ile Leu Leu Asp Leu Gly His His Glu
145                 150                 155                 160

Arg Ser Ile Met Thr Asp Leu Tyr Tyr Leu Ser Gln Thr Asp Gly Ala
                165                 170                 175

Gly Asp Trp Arg Glu Lys Glu Ala Lys Asp Leu Thr Glu Leu Val Gln
            180                 185                 190

Arg Arg Ile Thr Tyr Leu Gln Asn Pro Lys Asp Cys Ser Lys Ala Arg
        195                 200                 205

Lys Leu Val Cys Asn Ile Asn Lys Gly Cys Gly Tyr Gly Cys Gln Leu
    210                 215                 220

His His Val Val Tyr Cys Phe Met Ile Ala Tyr Gly Thr Gln Arg Thr
225                 230                 235                 240

Leu Ile Leu Glu Ser Gln Asn Trp Arg Tyr Ala Thr Gly Gly Trp Glu
                245                 250                 255

Thr Val Phe Arg Pro Val Ser Glu Thr Cys Thr Asp Arg Ser Gly Leu
            260                 265                 270

Ser Thr Gly His Trp Ser Gly Glu Val Asn Asp Lys Asn Ile Gln Val
        275                 280                 285

Val Glu Leu Pro Ile Val Asp Ser Leu His Pro Arg Pro Pro Tyr Leu
    290                 295                 300

Pro Leu Ala Val Pro Glu Asp Leu Ala Asp Arg Leu Leu Arg Val His
305                 310                 315                 320

Gly Asp Pro Ala Val Trp Trp Val Ser Gln Phe Val Lys Tyr Leu Ile
                325                 330                 335

Arg Pro Gln Pro Trp Leu Glu Lys Glu Ile Glu Ala Thr Lys Lys
            340                 345                 350

Leu Gly Phe Lys His Pro Val Ile Gly Val His Val Arg Arg Thr Asp
        355                 360                 365

Lys Val Gly Thr Glu Ala Ala Phe His Pro Ile Glu Glu Tyr Met Val
    370                 375                 380

His Val Glu Glu His Phe Gln Leu Leu Ala Arg Arg Met Gln Val Asp
385                 390                 395                 400

Lys Lys Arg Val Tyr Leu Ala Thr Asp Asp Pro Thr Leu Leu Lys Glu
                405                 410                 415

Ala Lys Thr Lys Tyr Ser Asn Tyr Glu Phe Ile Ser Asp Asn Ser Ile
            420                 425                 430

Ser Trp Ser Ala Gly Leu His Asn Arg Tyr Thr Glu Asn Ser Leu Arg
        435                 440                 445

Gly Val Ile Leu Asp Ile His Phe Leu Ser Gln Ala Asp Phe Leu Val
    450                 455                 460

Cys Thr Phe Ser Ser Gln Val Cys Arg Val Ala Tyr Glu Ile Met Gln
465                 470                 475                 480

Thr Leu His Pro Asp Ala Ser Ala Asn Phe His Ser Leu Asp Asp Ile
                485                 490                 495

Tyr Tyr Phe Gly Gly Gln Asn Ala His Asn Gln Ile Ala Val Tyr Pro
            500                 505                 510

His Lys Pro Arg Thr Glu Glu Glu Ile Pro Met Glu Pro Gly Asp Ile
        515                 520                 525
```

```
Ile Gly Val Ala Gly Asn His Trp Asp Gly Tyr Ser Lys Gly Ile Asn
    530                 535                 540

Arg Lys Leu Gly Lys Thr Gly Leu Tyr Pro Ser Tyr Lys Val Arg Glu
545                 550                 555                 560

Lys Ile Glu Thr Val Lys Tyr Pro Thr Tyr Pro Glu Ala Glu Lys
                565                 570                 575

<210> SEQ ID NO 40
<211> LENGTH: 575
<212> TYPE: PRT
<213> ORGANISM: Homo sapiens

<400> SEQUENCE: 40

Met Arg Pro Trp Thr Gly Ser Trp Arg Trp Ile Met Leu Ile Leu Phe
1               5                   10                  15

Ala Trp Gly Thr Leu Leu Phe Tyr Ile Gly Gly His Leu Val Arg Asp
                20                  25                  30

Asn Asp His Pro Asp His Ser Ser Arg Glu Leu Ser Lys Ile Leu Ala
            35                  40                  45

Lys Leu Glu Arg Leu Lys Gln Gln Asn Glu Asp Leu Arg Arg Met Ala
    50                  55                  60

Glu Ser Leu Arg Ile Pro Glu Gly Pro Ile Asp Gln Gly Pro Ala Ile
65                  70                  75                  80

Gly Arg Val Arg Val Leu Glu Glu Gln Leu Val Lys Ala Lys Glu Gln
                85                  90                  95

Ile Glu Asn Tyr Lys Lys Gln Thr Arg Asn Gly Leu Gly Lys Asp His
            100                 105                 110

Glu Ile Leu Arg Arg Arg Ile Glu Asn Gly Ala Lys Glu Leu Trp Phe
    115                 120                 125

Phe Leu Gln Ser Glu Leu Lys Lys Leu Lys Asn Leu Glu Gly Asn Glu
130                 135                 140

Leu Gln Arg His Ala Asp Glu Phe Leu Leu Asp Leu Gly His His Glu
145                 150                 155                 160

Arg Ser Ile Met Thr Asp Leu Tyr Tyr Leu Ser Gln Thr Asp Gly Ala
                165                 170                 175

Gly Asp Trp Arg Glu Lys Glu Ala Lys Asp Leu Thr Glu Leu Val Gln
            180                 185                 190

Arg Arg Ile Thr Tyr Leu Gln Asn Pro Lys Asp Cys Ser Lys Ala Lys
    195                 200                 205

Lys Leu Val Cys Asn Ile Asn Lys Gly Cys Gly Tyr Gly Cys Gln Leu
210                 215                 220

His His Val Val Tyr Cys Phe Met Ile Ala Tyr Gly Thr Gln Arg Thr
225                 230                 235                 240

Leu Ile Leu Glu Ser Gln Asn Trp Arg Tyr Ala Thr Gly Gly Trp Glu
                245                 250                 255

Thr Val Phe Arg Pro Val Ser Glu Thr Cys Thr Asp Arg Ser Gly Ile
            260                 265                 270

Ser Thr Gly His Trp Ser Gly Glu Val Lys Asp Lys Asn Val Gln Val
    275                 280                 285

Val Glu Leu Pro Ile Val Asp Ser Leu His Pro Arg Pro Pro Tyr Leu
290                 295                 300

Pro Leu Ala Val Pro Glu Asp Leu Ala Asp Arg Leu Val Arg Val His
305                 310                 315                 320

Gly Asp Pro Ala Val Trp Trp Val Ser Gln Phe Val Lys Tyr Leu Ile
                325                 330                 335
```

Arg Pro Gln Pro Trp Leu Glu Lys Glu Ile Glu Glu Ala Thr Lys Lys
                340                 345                 350

Leu Gly Phe Lys His Pro Val Ile Gly Val His Val Arg Arg Thr Asp
                355                 360                 365

Lys Val Gly Thr Glu Ala Ala Phe His Pro Ile Glu Glu Tyr Met Val
370                 375                 380

His Val Glu Glu His Phe Gln Leu Leu Ala Arg Arg Met Gln Val Asp
385                 390                 395                 400

Lys Lys Arg Val Tyr Leu Ala Thr Asp Asp Pro Ser Leu Leu Lys Glu
                405                 410                 415

Ala Lys Thr Lys Tyr Pro Asn Tyr Glu Phe Ile Ser Asp Asn Ser Ile
                420                 425                 430

Ser Trp Ser Ala Gly Leu His Asn Arg Tyr Thr Glu Asn Ser Leu Arg
                435                 440                 445

Gly Val Ile Leu Asp Ile His Phe Leu Ser Gln Ala Asp Phe Leu Val
            450                 455                 460

Cys Thr Phe Ser Ser Gln Val Cys Arg Val Ala Tyr Glu Ile Met Gln
465                 470                 475                 480

Thr Leu His Pro Asp Ala Ser Ala Asn Phe His Ser Leu Asp Asp Ile
                485                 490                 495

Tyr Tyr Phe Gly Gly Gln Asn Ala His Asn Gln Ile Ala Ile Tyr Ala
            500                 505                 510

His Gln Pro Arg Thr Ala Asp Glu Ile Pro Met Glu Pro Gly Asp Ile
                515                 520                 525

Ile Gly Val Ala Gly Asn His Trp Asp Gly Tyr Ser Lys Gly Val Asn
            530                 535                 540

Arg Lys Leu Gly Arg Thr Gly Leu Tyr Pro Ser Tyr Lys Val Arg Glu
545                 550                 555                 560

Lys Ile Glu Thr Val Lys Tyr Pro Thr Tyr Pro Glu Ala Glu Lys
                565                 570                 575

<210> SEQ ID NO 41
<211> LENGTH: 438
<212> TYPE: PRT
<213> ORGANISM: Mus musculus

<400> SEQUENCE: 41

Met Lys Pro His Leu Lys Gln Trp Arg Gln Arg Met Leu Phe Gly Ile
1               5                   10                  15

Phe Val Trp Gly Leu Leu Phe Leu Ala Ile Phe Ile Tyr Phe Thr Asn
                20                  25                  30

Ser Asn Pro Ala Ala Pro Met Pro Ser Ser Phe Ser Phe Leu Glu Arg
            35                  40                  45

Arg Gly Leu Leu Pro Leu Gln Gly Lys Gln Arg Val Ile Met Gly Ala
        50                  55                  60

Leu Gln Glu Pro Ser Leu Pro Arg Ser Leu Asp Ala Ser Lys Val Leu
65                  70                  75                  80

Leu Asp Ser His Pro Glu Asn Pro Phe His Pro Trp Pro Gly Asp Pro
                85                  90                  95

Gln Lys Trp Asp Gln Ala Pro Asn Gly Phe Asp Asn Gly Asp Glu Phe
            100                 105                 110

Phe Thr Ser Gln Val Gly Arg Lys Ser Gln Ser Ala Phe Tyr Pro Glu
        115                 120                 125

Glu Asp Ser Tyr Phe Phe Val Ala Asp Gln Pro Glu Leu Tyr His His
    130                 135                 140

```
Arg Gln Gly Ala Leu Glu Leu Pro Ser Pro Gly Glu Thr Ser Trp Arg
145                 150                 155                 160

Ser Gly Pro Val Gln Pro Lys Gln Lys Leu Leu His Pro Arg Arg Gly
            165                 170                 175

Ser Leu Pro Glu Glu Ala Tyr Asp Ser Asp Met Leu Ser Ala Ser Met
            180                 185                 190

Ser Arg Ala Phe Leu Tyr Arg Leu Trp Lys Gly Ala Val Ser Ser Lys
        195                 200                 205

Met Leu Asn Pro Arg Leu Gln Lys Ala Met Arg Tyr Tyr Met Ser Phe
    210                 215                 220

Asn Lys His Gly Val Arg Phe Arg Arg Gly Arg Arg Glu Ala Thr
225                 230                 235                 240

Arg Thr Gly Pro Glu Leu Leu Cys Glu Met Arg Arg Val Arg Val
            245                 250                 255

Arg Thr Leu Asp Gly Arg Glu Ala Pro Phe Ser Gly Leu Gly Trp Arg
            260                 265                 270

Pro Leu Val Pro Gly Val Pro Leu Ser Gln Leu His Pro Arg Gly Leu
        275                 280                 285

Ser Ser Cys Ala Val Val Met Ser Ala Gly Ala Ile Leu Asn Ser Ser
        290                 295                 300

Leu Gly Glu Glu Ile Asp Ser His Asp Ala Val Leu Arg Phe Asn Ser
305                 310                 315                 320

Ala Pro Thr Arg Gly Tyr Glu Lys Asp Val Gly Asn Lys Thr Thr Val
            325                 330                 335

Arg Ile Ile Asn Ser Gln Ile Leu Ala Asn Pro Ser His His Phe Ile
            340                 345                 350

Asp Ser Ala Leu Tyr Lys Asp Val Ile Leu Val Ala Trp Asp Pro Ala
        355                 360                 365

Pro Tyr Ser Ala Asn Leu Asn Leu Trp Tyr Lys Lys Pro Asp Tyr Asn
    370                 375                 380

Leu Phe Thr Pro Tyr Ile Gln His Arg Arg Lys Tyr Pro Thr Gln Pro
385                 390                 395                 400

Phe Tyr Ile Leu His Pro Lys Phe Ile Trp Gln Leu Trp Asp Ile Ile
            405                 410                 415

Gln Glu Asn Thr Arg Glu Lys Ile Gln Pro Asn Pro Pro Ser Ser Gly
            420                 425                 430

Phe Ile Gly Thr Cys Val
        435

<210> SEQ ID NO 42
<211> LENGTH: 406
<212> TYPE: PRT
<213> ORGANISM: Homo sapiens

<400> SEQUENCE: 42

Met Ile His Thr Asn Leu Lys Lys Lys Phe Ser Cys Cys Val Leu Val
1               5                   10                  15

Phe Leu Leu Phe Ala Val Ile Cys Val Trp Lys Glu Lys Lys Lys Gly
            20                  25                  30

Ser Tyr Tyr Asp Ser Phe Lys Leu Gln Thr Lys Glu Phe Gln Val Leu
        35                  40                  45

Lys Ser Leu Gly Lys Leu Ala Met Gly Ser Asp Ser Gln Ser Val Ser
    50                  55                  60

Ser Ser Ser Thr Gln Asp Pro His Arg Gly Arg Gln Thr Leu Gly Ser
65                  70                  75                  80
```

Leu Arg Gly Leu Ala Lys Ala Lys Pro Glu Ala Ser Phe Gln Val Trp
            85                  90                  95

Asn Lys Asp Ser Ser Lys Asn Leu Ile Pro Arg Leu Gln Lys Ile
        100                 105                 110

Trp Lys Asn Tyr Leu Ser Met Asn Lys Tyr Lys Val Ser Tyr Lys Gly
            115                 120                 125

Pro Gly Pro Gly Ile Lys Phe Ser Ala Glu Ala Leu Arg Cys His Leu
        130                 135                 140

Arg Asp His Val Asn Val Ser Met Val Glu Val Thr Asp Phe Pro Phe
145                 150                 155                 160

Asn Thr Ser Glu Trp Glu Gly Tyr Leu Pro Lys Ser Ile Arg Thr
            165                 170                 175

Lys Ala Gly Pro Trp Gly Arg Cys Ala Val Val Ser Ser Ala Gly Ser
        180                 185                 190

Leu Lys Ser Ser Gln Leu Gly Arg Glu Ile Asp Asp His Asp Ala Val
            195                 200                 205

Leu Arg Phe Asn Gly Ala Pro Thr Ala Asn Phe Gln Gln Asp Val Gly
        210                 215                 220

Thr Lys Thr Thr Ile Arg Leu Met Asn Ser Gln Leu Val Thr Thr Glu
225                 230                 235                 240

Lys Arg Phe Leu Lys Asp Ser Leu Tyr Asn Glu Gly Ile Leu Ile Val
            245                 250                 255

Trp Asp Pro Ser Val Tyr His Ser Asp Ile Pro Lys Trp Tyr Gln Asn
        260                 265                 270

Pro Asp Tyr Asn Phe Phe Asn Asn Tyr Lys Thr Tyr Arg Lys Leu His
        275                 280                 285

Pro Asn Gln Pro Phe Tyr Ile Leu Lys Pro Gln Met Pro Trp Glu Leu
        290                 295                 300

Trp Asp Ile Leu Gln Glu Ile Ser Pro Glu Glu Ile Gln Pro Asn Pro
305                 310                 315                 320

Pro Ser Ser Gly Met Leu Gly Ile Ile Met Met Thr Leu Cys Asp
            325                 330                 335

Gln Val Asp Ile Tyr Glu Phe Leu Pro Ser Lys Arg Lys Thr Asp Val
            340                 345                 350

Cys Tyr Tyr Tyr Gln Lys Phe Phe Asp Ser Ala Cys Thr Met Gly Ala
            355                 360                 365

Tyr His Pro Leu Leu Tyr Glu Lys Asn Leu Val Lys His Leu Asn Gln
        370                 375                 380

Gly Thr Asp Glu Asp Ile Tyr Leu Leu Gly Lys Ala Thr Leu Pro Gly
385                 390                 395                 400

Phe Arg Thr Ile His Cys
            405

<210> SEQ ID NO 43
<211> LENGTH: 175
<212> TYPE: PRT
<213> ORGANISM: Homo sapiens

<400> SEQUENCE: 43

Met Asn Ser Gln Leu Val Thr Thr Glu Lys Arg Phe Leu Lys Asp Ser
1               5                   10                  15

Leu Tyr Asn Glu Gly Ile Leu Ile Val Trp Asp Pro Ser Val Tyr His
            20                  25                  30

Ser Asp Ile Pro Lys Trp Tyr Gln Asn Pro Asp Tyr Asn Phe Phe Asn
        35                  40                  45

```
Asn Tyr Lys Thr Tyr Arg Lys Leu His Pro Asn Gln Pro Phe Tyr Ile
     50                  55                  60

Leu Lys Pro Gln Met Pro Trp Glu Leu Trp Asp Ile Leu Gln Glu Ile
 65                  70                  75                  80

Ser Pro Glu Glu Ile Gln Pro Asn Pro Ser Ser Gly Met Leu Gly
                 85                  90                  95

Ile Ile Ile Met Met Thr Leu Cys Asp Gln Val Asp Ile Tyr Glu Phe
                100                 105                 110

Leu Pro Ser Lys Arg Lys Thr Asp Val Cys Tyr Tyr Gln Lys Phe
            115                 120                 125

Phe Asp Ser Ala Cys Thr Met Gly Ala Tyr His Pro Leu Leu Tyr Glu
    130                 135                 140

Lys Asn Leu Val Lys His Leu Asn Gln Gly Thr Asp Glu Asp Ile Tyr
145                 150                 155                 160

Leu Leu Gly Lys Ala Thr Leu Pro Gly Phe Arg Thr Ile His Cys
                165                 170                 175

<210> SEQ ID NO 44
<211> LENGTH: 337
<212> TYPE: PRT
<213> ORGANISM: Mus musculus

<400> SEQUENCE: 44

Met Arg Arg Lys Thr Leu Lys Tyr Leu Thr Phe Phe Leu Leu Phe Ile
 1               5                  10                  15

Phe Leu Thr Ser Phe Val Leu Asn Tyr Ser Asn Thr Gly Val Pro Ser
                 20                  25                  30

Ala Trp Phe Pro Lys Gln Met Leu Leu Glu Leu Ser Glu Asn Phe Arg
             35                  40                  45

Arg Phe Ile Lys Ser Gln Pro Cys Thr Cys Arg His Cys Ile Ser Gln
     50                  55                  60

Asp Lys Val Ser Tyr Trp Phe Asp Gln Arg Phe Asn Lys Thr Met Gln
 65                  70                  75                  80

Pro Leu Leu Thr Val His Asn Ala Leu Met Glu Glu Asp Thr Tyr Arg
                 85                  90                  95

Trp Trp Leu Arg Leu Gln Arg Glu Arg Lys Pro Asn Asn Leu Ser Asp
            100                 105                 110

Thr Val Lys Glu Leu Phe Arg Leu Val Pro Gly Asn Val Asp Pro Met
115                 120                 125

Leu Asn Lys Arg Leu Val Gly Cys Arg Arg Cys Ala Val Val Gly Asn
130                 135                 140

Ser Gly Asn Leu Lys Asp Ser Ser Tyr Gly Pro Glu Ile Asp Ser His
145                 150                 155                 160

Asp Phe Val Leu Arg Met Asn Lys Ala Pro Thr Val Gly Phe Glu Ala
                165                 170                 175

Asp Val Gly Ser Arg Thr Thr His His Leu Val Tyr Pro Glu Ser Phe
            180                 185                 190

Arg Glu Leu Gly Glu Asn Val Asn Met Val Leu Val Pro Phe Lys Thr
        195                 200                 205

Thr Asp Leu Gln Trp Val Ile Ser Ala Thr Thr Gly Thr Ile Thr
210                 215                 220

His Thr Tyr Val Pro Val Pro Pro Lys Ile Lys Val Lys Gln Glu Lys
225                 230                 235                 240

Ile Leu Ile Tyr His Pro Ala Phe Ile Lys Tyr Val Phe Asp Asn Trp
                245                 250                 255
```

```
Leu Gln Gly His Gly Arg Tyr Pro Ser Thr Gly Ile Leu Ser Ile Ile
            260                 265                 270

Phe Ser Ile His Ile Cys Asp Glu Val Asp Leu Tyr Gly Phe Gly Ala
            275                 280                 285

Asp Ser Lys Gly Asn Trp His Tyr Trp Glu Asn Asn Pro Ser Ala
            290                 295                 300

Gly Ala Phe Arg Lys Thr Gly Val His Asp Gly Asp Phe Glu Tyr Asn
305                 310                 315                 320

Ile Thr Thr Thr Leu Ala Ala Ile Asn Lys Ile Arg Ile Phe Lys Gly
                    325                 330                 335

Arg

<210> SEQ ID NO 45
<211> LENGTH: 340
<212> TYPE: PRT
<213> ORGANISM: Homo sapiens

<400> SEQUENCE: 45

Met Val Thr Leu Arg Lys Arg Thr Leu Lys Val Leu Thr Phe Leu Val
1               5                   10                  15

Leu Phe Ile Phe Leu Thr Ser Phe Phe Leu Asn Tyr Ser His Thr Met
                20                  25                  30

Val Ala Thr Thr Trp Phe Pro Lys Gln Met Val Leu Glu Leu Ser Glu
            35                  40                  45

Asn Leu Lys Arg Leu Ile Lys His Arg Pro Cys Thr Cys Thr His Cys
        50                  55                  60

Ile Gly Gln Arg Lys Leu Ser Ala Trp Phe Asp Glu Arg Phe Asn Gln
65                  70                  75                  80

Thr Met Gln Pro Leu Leu Thr Ala Gln Asn Ala Leu Leu Glu Asp Asp
                85                  90                  95

Thr Tyr Arg Trp Trp Leu Arg Leu Gln Arg Glu Lys Lys Pro Asn Asn
            100                 105                 110

Leu Asn Asp Thr Ile Lys Glu Leu Phe Arg Val Val Pro Gly Asn Val
        115                 120                 125

Asp Pro Met Leu Glu Lys Arg Ser Val Gly Cys Arg Arg Cys Ala Val
130                 135                 140

Val Gly Asn Ser Gly Asn Leu Arg Glu Ser Ser Tyr Gly Pro Glu Ile
145                 150                 155                 160

Asp Ser His Asp Phe Val Leu Arg Met Asn Lys Ala Pro Thr Ala Gly
                165                 170                 175

Phe Glu Ala Asp Val Gly Thr Lys Thr Thr His His Leu Val Tyr Pro
            180                 185                 190

Glu Ser Phe Arg Glu Leu Gly Asp Asn Val Ser Met Ile Leu Val Pro
        195                 200                 205

Phe Lys Thr Ile Asp Leu Glu Trp Val Val Ser Ala Ile Thr Thr Gly
        210                 215                 220

Thr Ile Ser His Thr Tyr Ile Pro Val Pro Ala Lys Ile Arg Val Lys
225                 230                 235                 240

Gln Asp Lys Ile Leu Ile Tyr His Pro Ala Phe Ile Lys Tyr Val Phe
                245                 250                 255

Asp Asn Trp Leu Gln Gly His Gly Arg Tyr Pro Ser Thr Gly Ile Leu
            260                 265                 270

Ser Val Ile Phe Ser Met His Val Cys Asp Glu Val Asp Leu Tyr Gly
        275                 280                 285
```

```
Phe Gly Ala Asp Ser Lys Gly Asn Trp His His Tyr Trp Glu Asn Asn
        290                 295                 300

Pro Ser Ala Gly Ala Phe Arg Lys Thr Gly Val His Asp Ala Asp Phe
305                 310                 315                 320

Glu Ser Asn Val Thr Ala Thr Leu Ala Ser Ile Asn Lys Ile Arg Ile
                325                 330                 335

Phe Lys Gly Arg
            340

<210> SEQ ID NO 46
<211> LENGTH: 350
<212> TYPE: PRT
<213> ORGANISM: Homo sapiens

<400> SEQUENCE: 46

Met Lys Cys Ser Leu Arg Val Trp Phe Leu Ser Val Ala Phe Leu Leu
1               5                   10                  15

Val Phe Ile Met Ser Leu Leu Phe Thr Tyr Ser His Ser Met Ala
            20                  25                  30

Thr Leu Pro Tyr Leu Asp Ser Gly Ala Leu Asp Gly Thr His Arg Val
            35                  40                  45

Lys Leu Val Pro Gly Tyr Ala Gly Leu Gln Arg Leu Ser Lys Glu Arg
50                  55                  60

Leu Ser Gly Lys Ser Cys Ala Cys Arg Arg Cys Met Gly Asp Ala Gly
65                  70                  75                  80

Ala Ser Asp Trp Phe Asp Ser His Phe Asp Gly Asn Ile Ser Pro Val
                85                  90                  95

Trp Thr Arg Glu Asn Met Asp Leu Pro Pro Asp Val Gln Arg Trp Trp
            100                 105                 110

Met Met Leu Gln Pro Gln Phe Lys Ser His Asn Thr Asn Glu Val Leu
            115                 120                 125

Glu Lys Leu Phe Gln Ile Val Pro Gly Glu Asn Pro Tyr Arg Phe Arg
        130                 135                 140

Asp Pro His Gln Cys Arg Arg Cys Ala Val Val Gly Asn Ser Gly Asn
145                 150                 155                 160

Leu Arg Gly Ser Gly Tyr Gly Gln Asp Val Asp Gly His Asn Phe Ile
                165                 170                 175

Met Arg Met Asn Gln Ala Pro Thr Val Gly Phe Glu Gln Asp Val Gly
            180                 185                 190

Ser Arg Thr Thr His His Phe Met Tyr Pro Glu Ser Ala Lys Asn Leu
        195                 200                 205

Pro Ala Asn Val Ser Phe Val Leu Val Pro Phe Lys Val Leu Asp Leu
210                 215                 220

Leu Trp Ile Ala Ser Ala Leu Ser Thr Gly Gln Ile Arg Phe Thr Tyr
225                 230                 235                 240

Ala Pro Val Lys Ser Phe Leu Arg Val Asp Lys Glu Lys Val Gln Ile
                245                 250                 255

Tyr Asn Pro Ala Phe Phe Lys Tyr Ile His Asp Arg Trp Thr Glu His
            260                 265                 270

His Gly Arg Tyr Pro Ser Thr Gly Met Leu Val Leu Phe Phe Ala Leu
        275                 280                 285

His Val Cys Asp Glu Val Asn Val Tyr Gly Phe Gly Ala Asp Ser Arg
    290                 295                 300

Gly Asn Trp His His Tyr Trp Glu Asn Asn Arg Tyr Ala Gly Glu Phe
305                 310                 315                 320
```

```
Arg Lys Thr Gly Val His Asp Ala Asp Phe Glu Ala His Ile Ile Asp
                325                 330                 335
Met Leu Ala Lys Ala Ser Lys Ile Glu Val Tyr Arg Gly Asn
            340                 345                 350
```

<210> SEQ ID NO 47
<211> LENGTH: 444
<212> TYPE: PRT
<213> ORGANISM: Homo sapiens

<400> SEQUENCE: 47

```
Met Gly Leu Leu Val Phe Val Arg Asn Leu Leu Ala Leu Cys Leu
1               5                   10                  15
Phe Leu Val Leu Gly Phe Leu Tyr Tyr Ser Ala Trp Lys Leu His Leu
                20                  25                  30
Leu Gln Trp Glu Glu Asp Ser Ser Lys Tyr Ser His Ser Ser Ser Pro
                35                  40                  45
Gln Glu Lys Pro Val Ala Asp Ser Val Val Leu Ser Phe Asp Ser Ala
            50                  55                  60
Gly Gln Thr Leu Gly Ser Glu Tyr Asp Arg Leu Gly Phe Leu Leu Asn
65                  70                  75                  80
Leu Asp Ser Lys Leu Ser Pro Arg Thr Leu Cys Thr Val Val Phe Gly
                85                  90                  95
Leu Asp Cys Ile Leu Glu Ser Pro Gly Glu Pro Lys Lys Leu Leu Met
                100                 105                 110
Pro Ala Ser His Pro Leu Glu Ile Leu Lys Ser Leu Ser Glu Asp Ala
                115                 120                 125
Ala Phe Ala Leu Gly Phe Leu Lys Leu Pro Arg Pro Ala Glu Leu Ala
            130                 135                 140
Thr Lys Tyr Ala Asn Phe Ser Glu Gly Ala Cys Lys Pro Gly Tyr Ala
145                 150                 155                 160
Ser Ala Leu Met Thr Ala Ile Phe Pro Arg Phe Ser Lys Pro Ala Pro
                165                 170                 175
Met Phe Leu Asp Asp Ser Phe Arg Lys Trp Ala Arg Ile Arg Glu Phe
                180                 185                 190
Val Pro Pro Phe Gly Ile Lys Gly Gln Asp Asn Leu Ile Lys Ala Ile
                195                 200                 205
Leu Ser Val Thr Lys Glu Tyr Arg Leu Thr Pro Ala Leu Asp Ser Leu
            210                 215                 220
Arg Cys Arg Arg Cys Ile Ile Val Gly Asn Gly Gly Val Leu Ala Asn
225                 230                 235                 240
Lys Ser Leu Gly Ser Arg Ile Asp Asp Tyr Asp Ile Val Val Arg Leu
                245                 250                 255
Asn Ser Ala Pro Val Lys Gly Phe Glu Lys Asp Val Gly Ser Lys Thr
                260                 265                 270
Thr Leu Arg Ile Thr Tyr Pro Glu Gly Ala Met Gln Arg Pro Glu Gln
            275                 280                 285
Tyr Glu Arg Asp Ser Leu Phe Val Leu Ala Gly Phe Lys Trp Gln Asp
290                 295                 300
Phe Lys Trp Leu Lys Tyr Ile Val Tyr Lys Glu Arg Val Ser Ala Ser
305                 310                 315                 320
Asp Gly Phe Trp Lys Ser Val Ala Thr Arg Val Pro Lys Glu Pro Pro
                325                 330                 335
Glu Ile Arg Ile Leu Asn Pro Tyr Phe Ile Gln Glu Ala Ala Phe Thr
                340                 345                 350
```

```
Leu Ile Gly Leu Pro Phe Asn Gly Leu Met Gly Arg Gly Asn Ile
        355                 360                 365

Pro Thr Leu Gly Ser Val Ala Val Thr Met Ala Leu His Gly Cys Asp
    370                 375                 380

Glu Val Ala Val Ala Gly Phe Gly Tyr Asp Met Ser Thr Pro Asn Ala
385                 390                 395                 400

Pro Leu His Tyr Tyr Glu Thr Val Arg Met Ala Ala Ile Lys Glu Ser
                405                 410                 415

Trp Thr His Asn Ile Gln Arg Glu Lys Glu Phe Leu Arg Lys Leu Val
                420                 425                 430

Lys Ala Arg Val Ile Thr Asp Leu Ser Ser Gly Ile
                435                 440

<210> SEQ ID NO 48
<211> LENGTH: 390
<212> TYPE: PRT
<213> ORGANISM: Homo sapiens

<400> SEQUENCE: 48

Met Gly Leu Leu Val Phe Val Arg Asn Leu Leu Leu Ala Leu Cys Leu
1               5                   10                  15

Phe Leu Val Leu Gly Phe Leu Tyr Tyr Ser Ala Trp Lys Leu His Leu
                20                  25                  30

Leu Gln Trp Glu Glu Asp Ser Ser Lys Tyr Ser His Ser Ser Ser Pro
            35                  40                  45

Gln Glu Lys Pro Val Ala Asp Ser Val Val Leu Ser Phe Asp Ser Ala
        50                  55                  60

Gly Gln Thr Leu Gly Ser Glu Tyr Asp Arg Leu Gly Phe Leu Leu Asn
65                  70                  75                  80

Leu Asp Ser Lys Leu Pro Ala Glu Leu Ala Thr Lys Tyr Ala Asn Phe
                85                  90                  95

Ser Glu Gly Ala Cys Lys Pro Gly Tyr Ala Ser Ala Leu Met Thr Ala
                100                 105                 110

Ile Phe Pro Arg Phe Ser Lys Pro Ala Pro Met Phe Leu Asp Asp Ser
            115                 120                 125

Phe Arg Lys Trp Ala Arg Ile Arg Glu Phe Val Pro Pro Phe Gly Ile
    130                 135                 140

Lys Gly Gln Asp Asn Leu Ile Lys Ala Ile Leu Ser Val Thr Lys Glu
145                 150                 155                 160

Tyr Arg Leu Thr Pro Ala Leu Asp Ser Leu Arg Cys Arg Arg Cys Ile
                165                 170                 175

Ile Val Gly Asn Gly Gly Val Leu Ala Asn Lys Ser Leu Gly Ser Arg
                180                 185                 190

Ile Asp Asp Tyr Asp Ile Val Val Arg Leu Asn Ser Ala Pro Val Lys
            195                 200                 205

Gly Phe Glu Lys Asp Val Gly Ser Lys Thr Thr Leu Arg Ile Thr Tyr
    210                 215                 220

Pro Glu Gly Ala Met Gln Arg Pro Glu Gln Tyr Glu Arg Asp Ser Leu
225                 230                 235                 240

Phe Val Leu Ala Gly Phe Lys Trp Gln Asp Phe Lys Trp Leu Lys Tyr
                245                 250                 255

Ile Val Tyr Lys Glu Arg Val Ser Ala Ser Asp Gly Phe Trp Lys Ser
                260                 265                 270

Val Ala Thr Arg Val Pro Lys Glu Pro Pro Glu Ile Arg Ile Leu Asn
            275                 280                 285
```

Pro Tyr Phe Ile Gln Glu Ala Ala Phe Thr Leu Ile Gly Leu Pro Phe
           290                 295                 300

Asn Asn Gly Leu Met Gly Arg Gly Asn Ile Pro Thr Leu Gly Ser Val
305                 310                 315                 320

Ala Val Thr Met Ala Leu His Gly Cys Asp Glu Val Ala Val Ala Gly
                325                 330                 335

Phe Gly Tyr Asp Met Ser Thr Pro Asn Ala Pro Leu His Tyr Tyr Glu
                340                 345                 350

Thr Val Arg Met Ala Ala Ile Lys Glu Ser Trp Thr His Asn Ile Gln
            355                 360                 365

Arg Glu Lys Glu Phe Leu Arg Lys Leu Val Lys Ala Arg Val Ile Thr
    370                 375                 380

Asp Leu Ser Ser Gly Ile
385                 390

<210> SEQ ID NO 49
<211> LENGTH: 170
<212> TYPE: PRT
<213> ORGANISM: Homo sapiens

<400> SEQUENCE: 49

Met Gly Leu Leu Val Phe Val Arg Asn Leu Leu Ala Leu Cys Leu
1               5                   10                  15

Phe Leu Val Leu Gly Phe Leu Tyr Tyr Ser Ala Trp Lys Leu His Leu
                20                  25                  30

Leu Gln Trp Glu Glu Asp Ser Ser Lys Tyr Ser His Ser Ser Ser Pro
            35                  40                  45

Gln Glu Lys Pro Val Ala Asp Ser Val Val Leu Ser Phe Asp Ser Ala
    50                  55                  60

Gly Gln Thr Leu Gly Ser Glu Tyr Asp Arg Leu Gly Phe Leu Leu Asn
65                  70                  75                  80

Leu Asp Ser Lys Leu Pro Ala Glu Leu Ala Thr Lys Tyr Ala Asn Phe
                85                  90                  95

Ser Glu Gly Ala Cys Lys Pro Gly Tyr Ala Ser Ala Leu Met Thr Ala
                100                 105                 110

Ile Phe Pro Arg Phe Ser Lys Pro Ala Pro Met Phe Leu Asp Asp Ser
            115                 120                 125

Phe Arg Lys Trp Ala Arg Ile Arg Glu Phe Val Pro Pro Phe Gly Ile
130                 135                 140

Lys Gly Gln Val Leu Asp Ala Gln Tyr Pro Ala Arg Glu Arg Val Ser
145                 150                 155                 160

Ala Glu Ala Gly Glu Ser Ser Arg His His
                165                 170

<210> SEQ ID NO 50
<211> LENGTH: 429
<212> TYPE: PRT
<213> ORGANISM: Homo sapiens

<400> SEQUENCE: 50

Met Gly Leu Leu Val Phe Val Arg Asn Leu Leu Ala Leu Cys Leu
1               5                   10                  15

Phe Leu Val Leu Gly Phe Leu Tyr Tyr Ser Ala Trp Lys Leu His Leu
                20                  25                  30

Leu Gln Trp Glu Glu Asp Ser Asn Ser Val Val Leu Ser Phe Asp Ser
            35                  40                  45

Ala Gly Gln Thr Leu Gly Ser Glu Tyr Asp Arg Leu Gly Phe Leu Leu

```
                        50                  55                  60
Asn Leu Asp Ser Lys Leu Ser Pro Arg Thr Leu Cys Thr Val Val Phe
 65                  70                  75                  80

Gly Leu Asp Cys Ile Leu Glu Ser Pro Gly Glu Pro Lys Lys Leu Leu
                 85                  90                  95

Met Pro Ala Ser His Pro Leu Glu Ile Leu Lys Ser Leu Ser Glu Asp
                100                 105                 110

Ala Ala Phe Ala Leu Gly Phe Leu Lys Leu Pro Arg Pro Ala Glu Leu
                115                 120                 125

Ala Thr Lys Tyr Ala Asn Phe Ser Glu Gly Ala Cys Lys Pro Gly Tyr
                130                 135                 140

Ala Ser Ala Leu Met Thr Ala Ile Phe Pro Arg Phe Ser Lys Pro Ala
145                 150                 155                 160

Pro Met Phe Leu Asp Asp Ser Phe Arg Lys Trp Ala Arg Ile Arg Glu
                165                 170                 175

Phe Val Pro Pro Phe Gly Ile Lys Gly Gln Asp Asn Leu Ile Lys Ala
                180                 185                 190

Ile Leu Ser Val Thr Lys Glu Tyr Arg Leu Thr Pro Ala Leu Asp Ser
                195                 200                 205

Leu Arg Cys Arg Arg Cys Ile Ile Val Gly Asn Gly Gly Val Leu Ala
                210                 215                 220

Asn Lys Ser Leu Gly Ser Arg Ile Asp Asp Tyr Asp Ile Val Val Arg
225                 230                 235                 240

Leu Asn Ser Ala Pro Val Lys Gly Phe Glu Lys Asp Val Gly Ser Lys
                245                 250                 255

Thr Thr Leu Arg Ile Thr Tyr Pro Glu Gly Ala Met Gln Arg Pro Glu
                260                 265                 270

Gln Tyr Glu Arg Asp Ser Leu Phe Val Leu Ala Gly Phe Lys Trp Gln
                275                 280                 285

Asp Phe Lys Trp Leu Lys Tyr Ile Val Tyr Lys Glu Arg Val Ser Ala
                290                 295                 300

Ser Asp Gly Phe Trp Lys Ser Val Ala Thr Arg Val Pro Lys Glu Pro
305                 310                 315                 320

Pro Glu Ile Arg Ile Leu Asn Pro Tyr Phe Ile Gln Glu Ala Ala Phe
                325                 330                 335

Thr Leu Ile Gly Leu Pro Phe Asn Asn Gly Leu Met Gly Arg Gly Asn
                340                 345                 350

Ile Pro Thr Leu Gly Ser Val Ala Val Thr Met Ala Leu His Gly Cys
                355                 360                 365

Asp Glu Val Ala Val Ala Gly Phe Gly Tyr Asp Met Ser Thr Pro Asn
                370                 375                 380

Ala Pro Leu His Tyr Tyr Glu Thr Val Arg Met Ala Ala Ile Lys Glu
385                 390                 395                 400

Ser Trp Thr His Asn Ile Gln Arg Glu Lys Phe Leu Arg Lys Leu
                405                 410                 415

Val Lys Ala Arg Val Ile Thr Asp Leu Ser Ser Gly Ile
                420                 425
```

<210> SEQ ID NO 51
<211> LENGTH: 375
<212> TYPE: PRT
<213> ORGANISM: Homo sapiens

<400> SEQUENCE: 51

Met Gly Leu Leu Val Phe Val Arg Asn Leu Leu Leu Ala Leu Cys Leu

```
 1               5                  10                 15
Phe Leu Val Leu Gly Phe Leu Tyr Tyr Ser Ala Trp Lys Leu His Leu
                20                  25                 30

Leu Gln Trp Glu Glu Asp Ser Asn Ser Val Val Leu Ser Phe Asp Ser
                35                  40                 45

Ala Gly Gln Thr Leu Gly Ser Glu Tyr Asp Arg Leu Gly Phe Leu Leu
 50                  55                  60

Asn Leu Asp Ser Lys Leu Pro Ala Glu Leu Ala Thr Lys Tyr Ala Asn
 65                  70                  75                  80

Phe Ser Glu Gly Ala Cys Lys Pro Gly Tyr Ala Ser Ala Leu Met Thr
                85                  90                  95

Ala Ile Phe Pro Arg Phe Ser Lys Pro Ala Pro Met Phe Leu Asp Asp
                100                 105                110

Ser Phe Arg Lys Trp Ala Arg Ile Arg Glu Phe Val Pro Pro Phe Gly
                115                 120                125

Ile Lys Gly Gln Asp Asn Leu Ile Lys Ala Ile Leu Ser Val Thr Lys
                130                 135                140

Glu Tyr Arg Leu Thr Pro Ala Leu Asp Ser Leu Arg Cys Arg Arg Cys
145                 150                 155                160

Ile Ile Val Gly Asn Gly Gly Val Leu Ala Asn Lys Ser Leu Gly Ser
                165                 170                175

Arg Ile Asp Asp Tyr Asp Ile Val Arg Leu Asn Ser Ala Pro Val
                180                 185                190

Lys Gly Phe Glu Lys Asp Val Gly Ser Lys Thr Thr Leu Arg Ile Thr
                195                 200                205

Tyr Pro Glu Gly Ala Met Gln Arg Pro Glu Gln Tyr Glu Arg Asp Ser
                210                 215                220

Leu Phe Val Leu Ala Gly Phe Lys Trp Gln Asp Phe Lys Trp Leu Lys
225                 230                 235                240

Tyr Ile Val Tyr Lys Glu Arg Val Ser Ala Ser Asp Gly Phe Trp Lys
                245                 250                255

Ser Val Ala Thr Arg Val Pro Lys Glu Pro Pro Glu Ile Arg Ile Leu
                260                 265                270

Asn Pro Tyr Phe Ile Gln Glu Ala Ala Phe Thr Leu Ile Gly Leu Pro
                275                 280                285

Phe Asn Asn Gly Leu Met Gly Arg Gly Asn Ile Pro Thr Leu Gly Ser
                290                 295                300

Val Ala Val Thr Met Ala Leu His Gly Cys Asp Glu Val Ala Val Ala
305                 310                 315                320

Gly Phe Gly Tyr Asp Met Ser Thr Pro Asn Ala Pro Leu His Tyr Tyr
                325                 330                335

Glu Thr Val Arg Met Ala Ala Ile Lys Glu Ser Trp Thr His Asn Ile
                340                 345                350

Gln Arg Glu Lys Glu Phe Leu Arg Lys Leu Val Lys Ala Arg Val Ile
                355                 360                365

Thr Asp Leu Ser Ser Gly Ile
                370                 375

<210> SEQ ID NO 52
<211> LENGTH: 277
<212> TYPE: PRT
<213> ORGANISM: Homo sapiens

<400> SEQUENCE: 52

Met Gly Leu Leu Val Phe Val Arg Asn Leu Leu Leu Ala Leu Cys Leu
```

```
                1               5                  10                 15
Phe Leu Val Leu Gly Phe Leu Tyr Tyr Ser Ala Trp Lys Leu His Leu
                20                 25                 30

Leu Gln Trp Glu Glu Asp Ser Asn Ser Val Val Leu Ser Phe Asp Ser
                35                 40                 45

Ala Gly Gln Thr Leu Gly Ser Glu Tyr Asp Arg Leu Gly Phe Leu Leu
 50                 55                 60

Asn Leu Asp Ser Lys Leu Pro Ala Glu Leu Ala Thr Lys Tyr Ala Asn
 65                 70                 75                 80

Phe Ser Glu Gly Ala Cys Lys Pro Gly Tyr Ala Ser Ala Leu Met Thr
                85                 90                 95

Ala Ile Phe Pro Arg Phe Ser Lys Pro Ala Pro Met Phe Leu Asp Asp
                100                105                110

Ser Phe Arg Lys Trp Ala Arg Ile Arg Glu Phe Val Pro Pro Phe Gly
                115                120                125

Ile Lys Gly Gln Asp Asn Leu Ile Lys Ala Ile Leu Ser Val Thr Lys
                130                135                140

Glu Tyr Arg Leu Thr Pro Ala Leu Asp Ser Leu Arg Cys Arg Arg Cys
145                 150                155                160

Ile Ile Val Gly Asn Gly Gly Val Leu Ala Asn Lys Ser Leu Gly Ser
                165                170                175

Arg Ile Asp Asp Tyr Asp Ile Val Val Arg Leu Asn Ser Ala Pro Val
                180                185                190

Lys Gly Phe Glu Lys Asp Val Gly Ser Lys Thr Thr Leu Arg Ile Thr
                195                200                205

Tyr Pro Glu Gly Ala Met Gln Arg Pro Glu Gln Tyr Glu Arg Asp Ser
                210                215                220

Leu Phe Val Leu Ala Gly Phe Lys Trp Gln Asp Phe Lys Trp Leu Lys
225                 230                235                240

Tyr Ile Val Tyr Lys Glu Arg Val Ser Trp Thr His Asn Ile Gln Arg
                245                250                255

Glu Lys Glu Phe Leu Arg Lys Leu Val Lys Ala Arg Val Ile Thr Asp
                260                265                270

Leu Ser Ser Gly Ile
            275

<210> SEQ ID NO 53
<211> LENGTH: 155
<212> TYPE: PRT
<213> ORGANISM: Homo sapiens

<400> SEQUENCE: 53

Met Gly Leu Leu Val Phe Val Arg Asn Leu Leu Leu Ala Leu Cys Leu
1               5                  10                 15

Phe Leu Val Leu Gly Phe Leu Tyr Tyr Ser Ala Trp Lys Leu His Leu
                20                 25                 30

Leu Gln Trp Glu Glu Asp Ser Asn Ser Val Val Leu Ser Phe Asp Ser
                35                 40                 45

Ala Gly Gln Thr Leu Gly Ser Glu Tyr Asp Arg Leu Gly Phe Leu Leu
 50                 55                 60

Asn Leu Asp Ser Lys Leu Pro Ala Glu Leu Ala Thr Lys Tyr Ala Asn
 65                 70                 75                 80

Phe Ser Glu Gly Ala Cys Lys Pro Gly Tyr Ala Ser Ala Leu Met Thr
                85                 90                 95

Ala Ile Phe Pro Arg Phe Ser Lys Pro Ala Pro Met Phe Leu Asp Asp
```

```
              100                 105                 110
Ser Phe Arg Lys Trp Ala Arg Ile Arg Glu Phe Val Pro Pro Phe Gly
            115                 120                 125

Ile Lys Gly Gln Val Leu Asp Ala Gln Tyr Pro Ala Arg Glu Arg Val
130                 135                 140

Ser Ala Glu Ala Gly Glu Ser Ser Arg His His
145                 150                 155

<210> SEQ ID NO 54
<211> LENGTH: 413
<212> TYPE: PRT
<213> ORGANISM: Homo sapiens

<400> SEQUENCE: 54

Met Gly Leu Leu Val Phe Val Arg Asn Leu Leu Ala Leu Cys Leu
1               5                   10                  15

Phe Leu Val Leu Gly Phe Leu Tyr Tyr Ser Ala Trp Lys Leu His Leu
                20                  25                  30

Leu Gln Trp Glu Glu Asp Ser Lys Tyr Asp Arg Leu Gly Phe Leu Leu
            35                  40                  45

Asn Leu Asp Ser Lys Leu Ser Pro Arg Thr Leu Cys Thr Val Val Phe
50                  55                  60

Gly Leu Asp Cys Ile Leu Glu Ser Pro Gly Glu Pro Lys Lys Leu Leu
65                  70                  75                  80

Met Pro Ala Ser His Pro Leu Glu Ile Leu Lys Ser Leu Ser Glu Asp
                85                  90                  95

Ala Ala Phe Ala Leu Gly Phe Leu Lys Leu Pro Arg Pro Ala Glu Leu
            100                 105                 110

Ala Thr Lys Tyr Ala Asn Phe Ser Glu Gly Ala Cys Lys Pro Gly Tyr
        115                 120                 125

Ala Ser Ala Leu Met Thr Ala Ile Phe Pro Arg Phe Ser Lys Pro Ala
    130                 135                 140

Pro Met Phe Leu Asp Asp Ser Phe Arg Lys Trp Ala Arg Ile Arg Glu
145                 150                 155                 160

Phe Val Pro Pro Phe Gly Ile Lys Gly Gln Asp Asn Leu Ile Lys Ala
                165                 170                 175

Ile Leu Ser Val Thr Lys Glu Tyr Arg Leu Thr Pro Ala Leu Asp Ser
            180                 185                 190

Leu Arg Cys Arg Arg Cys Ile Ile Val Gly Asn Gly Gly Val Leu Ala
        195                 200                 205

Asn Lys Ser Leu Gly Ser Arg Ile Asp Asp Tyr Asp Ile Val Val Arg
    210                 215                 220

Leu Asn Ser Ala Pro Val Lys Gly Phe Glu Lys Asp Val Gly Ser Lys
225                 230                 235                 240

Thr Thr Leu Arg Ile Thr Tyr Pro Glu Gly Ala Met Gln Arg Pro Glu
                245                 250                 255

Gln Tyr Glu Arg Asp Ser Leu Phe Val Leu Ala Gly Phe Lys Trp Gln
            260                 265                 270

Asp Phe Lys Trp Leu Lys Tyr Ile Val Tyr Lys Glu Arg Val Ser Ala
        275                 280                 285

Ser Asp Gly Phe Trp Lys Ser Val Ala Thr Arg Val Pro Lys Glu Pro
    290                 295                 300

Pro Glu Ile Arg Ile Leu Asn Pro Tyr Phe Ile Gln Glu Ala Ala Phe
305                 310                 315                 320

Thr Leu Ile Gly Leu Pro Phe Asn Asn Gly Leu Met Gly Arg Gly Asn
```

```
                    325                 330                 335
Ile Pro Thr Leu Gly Ser Val Ala Val Thr Met Ala Leu His Gly Cys
                340                 345                 350

Asp Glu Val Ala Val Ala Gly Phe Gly Tyr Asp Met Ser Thr Pro Asn
            355                 360                 365

Ala Pro Leu His Tyr Tyr Glu Thr Val Arg Met Ala Ala Ile Lys Glu
        370                 375                 380

Ser Trp Thr His Asn Ile Gln Arg Glu Lys Phe Leu Arg Lys Leu
385                 390                 395                 400

Val Lys Ala Arg Val Ile Thr Asp Leu Ser Ser Gly Ile
                405                 410

<210> SEQ ID NO 55
<211> LENGTH: 359
<212> TYPE: PRT
<213> ORGANISM: Homo sapiens

<400> SEQUENCE: 55

Met Gly Leu Leu Val Phe Val Arg Asn Leu Leu Ala Leu Cys Leu
1               5                   10                  15

Phe Leu Val Leu Gly Phe Leu Tyr Tyr Ser Ala Trp Lys Leu His Leu
            20                  25                  30

Leu Gln Trp Glu Glu Asp Ser Lys Tyr Asp Arg Leu Gly Phe Leu Leu
        35                  40                  45

Asn Leu Asp Ser Lys Leu Pro Ala Glu Leu Ala Thr Lys Tyr Ala Asn
    50                  55                  60

Phe Ser Glu Gly Ala Cys Lys Pro Gly Tyr Ala Ser Ala Leu Met Thr
65                  70                  75                  80

Ala Ile Phe Pro Arg Phe Ser Lys Pro Ala Pro Met Phe Leu Asp Asp
                85                  90                  95

Ser Phe Arg Lys Trp Ala Arg Ile Arg Glu Phe Val Pro Pro Phe Gly
            100                 105                 110

Ile Lys Gly Gln Asp Asn Leu Ile Lys Ala Ile Leu Ser Val Thr Lys
        115                 120                 125

Glu Tyr Arg Leu Thr Pro Ala Leu Asp Ser Leu Arg Cys Arg Arg Cys
    130                 135                 140

Ile Ile Val Gly Asn Gly Gly Val Leu Ala Asn Lys Ser Leu Gly Ser
145                 150                 155                 160

Arg Ile Asp Asp Tyr Asp Ile Val Val Arg Leu Asn Ser Ala Pro Val
                165                 170                 175

Lys Gly Phe Glu Lys Asp Val Gly Ser Lys Thr Thr Leu Arg Ile Thr
            180                 185                 190

Tyr Pro Glu Gly Ala Met Gln Arg Pro Glu Gln Tyr Glu Arg Asp Ser
        195                 200                 205

Leu Phe Val Leu Ala Gly Phe Lys Trp Gln Asp Phe Lys Trp Leu Lys
    210                 215                 220

Tyr Ile Val Tyr Lys Glu Arg Val Ser Ala Ser Asp Gly Phe Trp Lys
225                 230                 235                 240

Ser Val Ala Thr Arg Val Pro Lys Glu Pro Pro Glu Ile Arg Ile Leu
                245                 250                 255

Asn Pro Tyr Phe Ile Gln Glu Ala Ala Phe Thr Leu Ile Gly Leu Pro
            260                 265                 270

Phe Asn Asn Gly Leu Met Gly Arg Gly Asn Ile Pro Thr Leu Gly Ser
        275                 280                 285

Val Ala Val Thr Met Ala Leu His Gly Cys Asp Glu Val Ala Val Ala
```

```
                290                 295                 300
Gly Phe Gly Tyr Asp Met Ser Thr Pro Asn Ala Pro Leu His Tyr Tyr
305                 310                 315                 320

Glu Thr Val Arg Met Ala Ala Ile Lys Glu Ser Trp Thr His Asn Ile
                325                 330                 335

Gln Arg Glu Lys Glu Phe Leu Arg Lys Leu Val Lys Ala Arg Val Ile
            340                 345                 350

Thr Asp Leu Ser Ser Gly Ile
        355

<210> SEQ ID NO 56
<211> LENGTH: 139
<212> TYPE: PRT
<213> ORGANISM: Homo sapiens

<400> SEQUENCE: 56

Met Gly Leu Leu Val Phe Val Arg Asn Leu Leu Ala Leu Cys Leu
1               5                  10                  15

Phe Leu Val Leu Gly Phe Leu Tyr Tyr Ser Ala Trp Lys Leu His Leu
                20                  25                  30

Leu Gln Trp Glu Glu Asp Ser Lys Tyr Asp Arg Leu Gly Phe Leu Leu
            35                  40                  45

Asn Leu Asp Ser Lys Leu Pro Ala Glu Leu Ala Thr Lys Tyr Ala Asn
50                  55                  60

Phe Ser Glu Gly Ala Cys Lys Pro Gly Tyr Ala Ser Ala Leu Met Thr
65                  70                  75                  80

Ala Ile Phe Pro Arg Phe Ser Lys Pro Ala Pro Met Phe Leu Asp Asp
                85                  90                  95

Ser Phe Arg Lys Trp Ala Arg Ile Arg Glu Phe Val Pro Pro Phe Gly
            100                 105                 110

Ile Lys Gly Gln Val Leu Asp Ala Gln Tyr Pro Ala Arg Glu Arg Val
        115                 120                 125

Ser Ala Glu Ala Gly Glu Ser Ser Arg His His
    130                 135

<210> SEQ ID NO 57
<211> LENGTH: 331
<212> TYPE: PRT
<213> ORGANISM: Homo sapiens

<400> SEQUENCE: 57

Met Arg Gly Tyr Leu Val Ala Ile Phe Leu Ser Ala Val Phe Leu Tyr
1               5                   10                  15

Tyr Val Leu His Cys Ile Leu Trp Gly Thr Asn Val Tyr Trp Val Ala
                20                  25                  30

Pro Val Glu Met Lys Arg Arg Asn Lys Ile Gln Pro Cys Leu Ser Lys
            35                  40                  45

Pro Ala Phe Ala Ser Leu Leu Arg Phe His Gln Phe His Pro Phe Leu
    50                  55                  60

Cys Ala Ala Asp Phe Arg Lys Ile Ala Ser Leu Tyr Gly Ser Asp Lys
65                  70                  75                  80

Phe Asp Leu Pro Tyr Gly Met Arg Thr Ser Ala Glu Tyr Phe Arg Leu
                85                  90                  95

Ala Leu Ser Lys Leu Gln Ser Cys Asp Leu Phe Asp Glu Phe Asp Asn
            100                 105                 110

Ile Pro Cys Lys Lys Cys Val Val Val Gly Asn Gly Gly Val Leu Lys
        115                 120                 125
```

```
Asn Lys Thr Leu Gly Glu Lys Ile Asp Ser Tyr Asp Val Ile Ile Arg
        130                 135                 140

Met Asn Asn Gly Pro Val Leu Gly His Glu Glu Val Gly Arg Arg
145                 150                 155                 160

Thr Thr Phe Arg Leu Phe Tyr Pro Glu Ser Val Phe Ser Asp Pro Ile
                165                 170                 175

His Asn Asp Pro Asn Thr Thr Val Ile Leu Thr Ala Phe Lys Pro His
            180                 185                 190

Asp Leu Arg Trp Leu Leu Glu Leu Leu Met Gly Asp Lys Ile Asn Thr
        195                 200                 205

Asn Gly Phe Trp Lys Lys Pro Ala Leu Asn Leu Ile Tyr Lys Pro Tyr
    210                 215                 220

Gln Ile Arg Ile Leu Asp Pro Phe Ile Ile Arg Thr Ala Ala Tyr Glu
225                 230                 235                 240

Leu Leu His Phe Pro Lys Val Phe Pro Lys Asn Gln Lys Pro Lys His
                245                 250                 255

Pro Thr Thr Gly Ile Ile Ala Ile Thr Leu Ala Phe Tyr Ile Cys His
            260                 265                 270

Glu Val His Leu Ala Gly Phe Lys Tyr Asn Phe Ser Asp Leu Lys Ser
        275                 280                 285

Pro Leu His Tyr Tyr Gly Asn Ala Thr Met Ser Leu Met Asn Lys Asn
    290                 295                 300

Ala Tyr His Asn Val Thr Ala Glu Gln Leu Phe Leu Lys Asp Ile Ile
305                 310                 315                 320

Glu Lys Asn Leu Val Ile Asn Leu Thr Gln Asp
                325                 330

<210> SEQ ID NO 58
<211> LENGTH: 722
<212> TYPE: PRT
<213> ORGANISM: Mus musculus

<400> SEQUENCE: 58

Met Glu Lys Asn Gly Asn Asn Arg Lys Leu Arg Val Cys Val Ala Thr
1               5                   10                  15

Cys Asn Arg Ala Asp Tyr Ser Lys Leu Ala Pro Ile Met Phe Gly Ile
                20                  25                  30

Lys Thr Glu Pro Ala Phe Phe Glu Leu Asp Val Val Leu Gly Ser
            35                  40                  45

His Leu Ile Asp Asp Tyr Gly Asn Thr Tyr Arg Met Ile Glu Gln Asp
    50                  55                  60

Asp Phe Asp Ile Asn Thr Arg Leu His Thr Ile Val Arg Gly Glu Asp
65                  70                  75                  80

Glu Ala Ala Met Val Glu Ser Val Gly Leu Ala Leu Val Lys Leu Pro
                85                  90                  95

Asp Val Leu Asn Arg Leu Lys Pro Asp Ile Met Ile Val His Gly Asp
                100                 105                 110

Arg Phe Asp Ala Leu Ala Leu Ala Thr Ser Ala Ala Leu Met Asn Ile
            115                 120                 125

Arg Ile Leu His Ile Glu Gly Gly Glu Val Ser Gly Thr Ile Asp Asp
        130                 135                 140

Ser Ile Arg His Ala Ile Thr Lys Leu Ala His Tyr His Val Cys Cys
145                 150                 155                 160

Thr Arg Ser Ala Glu Gln His Leu Ile Ser Met Cys Glu Asp His Asp
                165                 170                 175
```

-continued

```
Arg Ile Leu Leu Ala Gly Cys Pro Ser Tyr Asp Lys Leu Leu Ser Ala
            180                 185                 190

Lys Asn Lys Asp Tyr Met Ser Ile Arg Met Trp Leu Gly Asp Asp
        195                 200                 205

Val Lys Cys Lys Asp Tyr Ile Val Ala Leu Gln His Pro Val Thr Thr
    210                 215                 220

Asp Ile Lys His Ser Ile Lys Met Phe Glu Leu Thr Leu Asp Ala Leu
225                 230                 235                 240

Ile Ser Phe Asn Lys Arg Thr Leu Val Leu Phe Pro Asn Ile Asp Ala
                245                 250                 255

Gly Ser Lys Glu Met Val Arg Val Met Arg Lys Lys Gly Ile Glu His
            260                 265                 270

His Pro Asn Phe Arg Ala Val Lys His Val Pro Phe Asp Gln Phe Ile
        275                 280                 285

Gln Leu Val Ala His Ala Gly Cys Met Ile Gly Asn Ser Ser Cys Gly
    290                 295                 300

Val Arg Glu Val Gly Ala Phe Gly Thr Pro Val Ile Asn Leu Gly Thr
305                 310                 315                 320

Arg Gln Ile Gly Arg Glu Thr Gly Glu Asn Val Leu His Val Arg Asp
                325                 330                 335

Ala Asp Thr Gln Asp Lys Ile Leu Gln Ala Leu His Leu Gln Phe Gly
            340                 345                 350

Lys Gln Tyr Pro Cys Ser Lys Ile Tyr Gly Asp Gly Asn Ala Val Pro
        355                 360                 365

Arg Ile Leu Lys Phe Leu Lys Ser Ile Asp Leu Gln Glu Pro Leu Gln
    370                 375                 380

Lys Lys Phe Cys Phe Pro Pro Val Lys Glu Asn Ile Ser Gln Asp Ile
385                 390                 395                 400

Asp His Ile Leu Glu Thr Leu Ser Ala Leu Ala Val Asp Leu Gly Gly
                405                 410                 415

Thr Asn Leu Arg Val Ala Ile Val Ser Met Lys Gly Glu Ile Val Lys
            420                 425                 430

Lys Tyr Thr Gln Phe Asn Pro Lys Thr Tyr Glu Arg Ile Ser Leu
        435                 440                 445

Ile Leu Gln Met Cys Val Glu Ala Ala Glu Ala Val Lys Leu Asn
    450                 455                 460

Cys Arg Ile Leu Gly Val Gly Ile Ser Thr Gly Gly Arg Val Asn Pro
465                 470                 475                 480

Gln Glu Gly Val Val Leu His Ser Thr Lys Leu Ile Gln Glu Trp Asn
                485                 490                 495

Ser Val Asp Leu Arg Thr Pro Leu Ser Asp Thr Leu His Leu Pro Val
            500                 505                 510

Trp Val Asp Asn Asp Gly Asn Cys Ala Ala Met Ala Glu Arg Lys Phe
        515                 520                 525

Gly Gln Gly Lys Gly Gln Glu Asn Phe Val Thr Leu Ile Thr Gly Thr
    530                 535                 540

Gly Ile Gly Gly Gly Ile Ile His Gln His Glu Leu Ile His Gly Ser
545                 550                 555                 560

Ser Phe Cys Ala Ala Glu Leu Gly His Leu Val Val Ser Leu Asp Gly
                565                 570                 575

Pro Asp Cys Ser Cys Gly Ser His Gly Cys Ile Glu Ala Tyr Ala Ser
            580                 585                 590

Gly Met Ala Leu Gln Arg Glu Ala Lys Lys Leu His Asp Glu Asp Leu
```

-continued

```
                595                 600                 605
Leu Leu Val Glu Gly Met Ser Val Pro Lys Asp Glu Ala Val Gly Ala
    610                 615                 620

Leu His Leu Ile Gln Ala Ala Lys Leu Gly Asn Val Lys Ala Gln Ser
625                 630                 635                 640

Ile Leu Arg Thr Ala Gly Thr Ala Leu Gly Leu Gly Val Val Asn Ile
                645                 650                 655

Leu His Thr Met Asn Pro Ser Leu Val Ile Leu Ser Gly Val Leu Ala
            660                 665                 670

Ser His Tyr Ile His Ile Val Lys Asp Val Ile Arg Gln Gln Ala Leu
            675                 680                 685

Ser Ser Val Gln Asp Val Asp Val Val Ser Asp Leu Val Asp Pro
    690                 695                 700

Ala Leu Leu Gly Ala Ala Ser Met Val Leu Asp Tyr Thr Thr Arg Arg
705                 710                 715                 720

Ile His

<210> SEQ ID NO 59
<211> LENGTH: 722
<212> TYPE: PRT
<213> ORGANISM: Homo sapiens

<400> SEQUENCE: 59

Met Glu Lys Asn Gly Asn Asn Arg Lys Leu Arg Val Cys Val Ala Thr
1               5                   10                  15

Cys Asn Arg Ala Asp Tyr Ser Lys Leu Ala Pro Ile Met Phe Gly Ile
            20                  25                  30

Lys Thr Glu Pro Glu Phe Phe Glu Leu Asp Val Val Leu Gly Ser
        35                  40                  45

His Leu Ile Asp Asp Tyr Gly Asn Thr Tyr Arg Met Ile Glu Gln Asp
    50                  55                  60

Asp Phe Asp Ile Asn Thr Arg Leu His Thr Ile Val Arg Gly Glu Asp
65                  70                  75                  80

Glu Ala Ala Met Val Glu Ser Val Gly Leu Ala Leu Val Lys Leu Pro
                85                  90                  95

Asp Val Leu Asn Arg Leu Lys Pro Asp Ile Met Ile Val His Gly Asp
            100                 105                 110

Arg Phe Asp Ala Leu Ala Leu Ala Thr Ser Ala Ala Leu Met Asn Ile
        115                 120                 125

Arg Ile Leu His Ile Glu Gly Gly Glu Val Ser Gly Thr Ile Asp Asp
    130                 135                 140

Ser Ile Arg His Ala Ile Thr Lys Leu Ala His Tyr His Val Cys Cys
145                 150                 155                 160

Thr Arg Ser Ala Glu Gln His Leu Ile Ser Met Cys Glu Asp His
                165                 170                 175

Arg Ile Leu Leu Ala Gly Cys Pro Ser Tyr Asp Lys Leu Leu Ser Ala
            180                 185                 190

Lys Asn Lys Asp Tyr Met Ser Ile Ile Arg Met Trp Leu Gly Asp Asp
        195                 200                 205

Val Lys Ser Lys Asp Tyr Ile Val Ala Leu Gln His Pro Val Thr Thr
    210                 215                 220

Asp Ile Lys His Ser Ile Lys Met Phe Glu Leu Thr Leu Asp Ala Leu
225                 230                 235                 240

Ile Ser Phe Asn Lys Arg Thr Leu Val Leu Phe Pro Asn Ile Asp Ala
                245                 250                 255
```

-continued

```
Gly Ser Lys Glu Met Val Arg Val Met Arg Lys Lys Gly Ile Glu His
            260                 265                 270
His Pro Asn Phe Arg Ala Val Lys His Val Pro Phe Asp Gln Phe Ile
            275                 280                 285
Gln Leu Val Ala His Ala Gly Cys Met Ile Gly Asn Ser Ser Cys Gly
            290                 295                 300
Val Arg Glu Val Gly Ala Phe Gly Thr Pro Val Ile Asn Leu Gly Thr
305                 310                 315                 320
Arg Gln Ile Gly Arg Glu Thr Gly Glu Asn Val Leu His Val Arg Asp
                325                 330                 335
Ala Asp Thr Gln Asp Lys Ile Leu Gln Ala Leu His Leu Gln Phe Gly
            340                 345                 350
Lys Gln Tyr Pro Cys Ser Lys Ile Tyr Gly Asp Gly Asn Ala Val Pro
            355                 360                 365
Arg Ile Leu Lys Phe Leu Lys Ser Ile Asp Leu Gln Glu Pro Leu Gln
            370                 375                 380
Lys Lys Phe Cys Phe Pro Pro Val Lys Glu Asn Ile Ser Gln Asp Ile
385                 390                 395                 400
Asp His Ile Leu Glu Thr Leu Ser Ala Leu Ala Val Asp Leu Gly Gly
                405                 410                 415
Thr Asn Leu Arg Val Ala Ile Val Ser Met Lys Gly Glu Ile Val Lys
            420                 425                 430
Lys Tyr Thr Gln Phe Asn Pro Lys Thr Tyr Glu Glu Arg Ile Asn Leu
            435                 440                 445
Ile Leu Gln Met Cys Val Glu Ala Ala Glu Ala Val Lys Leu Asn
            450                 455                 460
Cys Arg Ile Leu Gly Val Gly Ile Ser Thr Gly Gly Arg Val Asn Pro
465                 470                 475                 480
Arg Glu Gly Ile Val Leu His Ser Thr Lys Leu Ile Gln Glu Trp Asn
                485                 490                 495
Ser Val Asp Leu Arg Thr Pro Leu Ser Asp Thr Leu His Leu Pro Val
            500                 505                 510
Trp Val Asp Asn Asp Gly Asn Cys Ala Ala Leu Ala Glu Arg Lys Phe
            515                 520                 525
Gly Gln Gly Lys Gly Leu Glu Asn Phe Val Thr Leu Ile Thr Gly Thr
            530                 535                 540
Gly Ile Gly Gly Gly Ile Ile His Gln His Glu Leu Ile His Gly Ser
545                 550                 555                 560
Ser Phe Cys Ala Ala Glu Leu Gly His Leu Val Val Ser Leu Asp Gly
                565                 570                 575
Pro Asp Cys Ser Cys Gly Ser His Gly Cys Ile Glu Ala Tyr Ala Ser
            580                 585                 590
Gly Met Ala Leu Gln Arg Glu Ala Lys Lys Leu His Asp Glu Asp Leu
            595                 600                 605
Leu Leu Val Glu Gly Met Ser Val Pro Lys Asp Glu Ala Val Gly Ala
            610                 615                 620
Leu His Leu Ile Gln Ala Ala Lys Leu Gly Asn Ala Lys Ala Gln Ser
625                 630                 635                 640
Ile Leu Arg Thr Ala Gly Thr Ala Leu Gly Leu Gly Val Val Asn Ile
                645                 650                 655
Leu His Thr Met Asn Pro Ser Leu Val Ile Leu Ser Gly Val Leu Ala
            660                 665                 670
Ser His Tyr Ile His Ile Val Lys Asp Val Ile Arg Gln Gln Ala Leu
            675                 680                 685
```

```
Ser Ser Val Gln Asp Val Asp Val Val Ser Asp Leu Val Asp Pro
    690                 695                 700

Ala Leu Leu Gly Ala Ala Ser Met Val Leu Asp Tyr Thr Thr Arg Arg
705                 710                 715                 720

Ile Tyr

<210> SEQ ID NO 60
<211> LENGTH: 427
<212> TYPE: PRT
<213> ORGANISM: Homo sapiens

<400> SEQUENCE: 60

Met Ser Lys Gly Leu Pro Ala Arg Gln Asp Met Glu Lys Glu Arg Glu
  1               5                  10                  15

Thr Leu Gln Ala Trp Lys Glu Arg Val Gly Gln Glu Leu Asp Arg Val
             20                  25                  30

Val Ala Phe Trp Met Glu His Ser His Asp Gln Glu His Gly Gly Phe
         35                  40                  45

Phe Thr Cys Leu Gly Arg Glu Gly Arg Val Tyr Asp Asp Leu Lys Tyr
     50                  55                  60

Val Trp Leu Gln Gly Arg Gln Val Trp Met Tyr Cys Arg Leu Tyr Arg
 65                  70                  75                  80

Thr Phe Glu Arg Phe Arg His Ala Gln Leu Leu Asp Ala Ala Lys Ala
                 85                  90                  95

Gly Gly Glu Phe Leu Leu Arg Tyr Ala Arg Val Ala Pro Pro Gly Lys
            100                 105                 110

Lys Cys Ala Phe Val Leu Thr Arg Asp Gly Arg Pro Val Lys Val Gln
        115                 120                 125

Arg Thr Ile Phe Ser Glu Cys Phe Tyr Thr Met Ala Met Asn Glu Leu
    130                 135                 140

Trp Arg Ala Thr Gly Glu Val Arg Tyr Gln Thr Glu Ala Val Glu Met
145                 150                 155                 160

Met Asp Gln Ile Val His Trp Val Gln Glu Asp Ala Ser Gly Leu Gly
                165                 170                 175

Arg Pro Gln Leu Gln Gly Ala Pro Ala Glu Pro Met Ala Val Pro
            180                 185                 190

Met Met Leu Leu Asn Leu Val Glu Gln Leu Gly Glu Ala Asp Glu Glu
        195                 200                 205

Leu Ala Gly Lys Tyr Ala Glu Leu Gly Asp Trp Cys Ala Arg Arg Ile
    210                 215                 220

Leu Gln His Val Gln Arg Asp Gly Gln Ala Val Leu Glu Asn Val Ser
225                 230                 235                 240

Glu Gly Gly Lys Glu Leu Pro Gly Cys Leu Gly Arg Gln Gln Asn Pro
                245                 250                 255

Gly His Thr Leu Glu Ala Gly Trp Phe Leu Leu Arg His Cys Ile Arg
            260                 265                 270

Lys Gly Asp Pro Glu Leu Arg Ala His Val Ile Asp Lys Phe Leu Leu
        275                 280                 285

Leu Pro Phe His Ser Gly Trp Asp Pro Asp His Gly Gly Leu Phe Tyr
    290                 295                 300

Phe Gln Asp Ala Asp Asn Phe Cys Pro Thr Gln Leu Glu Trp Ala Met
305                 310                 315                 320

Lys Leu Trp Trp Pro His Ser Glu Ala Met Ile Ala Phe Leu Met Gly
                325                 330                 335
```

```
Tyr Ser Asp Ser Gly Asp Pro Val Leu Leu Arg Leu Phe Tyr Gln Val
            340                 345                 350

Ala Glu Tyr Thr Phe Arg Gln Phe Arg Asp Pro Glu Tyr Gly Glu Trp
            355                 360                 365

Phe Gly Tyr Leu Ser Arg Glu Gly Lys Val Ala Leu Ser Ile Lys Gly
            370                 375                 380

Gly Pro Phe Lys Gly Cys Phe His Val Pro Arg Cys Leu Ala Met Cys
385                 390                 395                 400

Glu Glu Met Leu Gly Ala Leu Leu Ser Arg Pro Ala Pro Ala Pro Ser
                405                 410                 415

Pro Ala Pro Thr Pro Ala Cys Arg Gly Ala Glu
            420                 425

<210> SEQ ID NO 61
<211> LENGTH: 358
<212> TYPE: PRT
<213> ORGANISM: Homo sapiens

<400> SEQUENCE: 61

Pro Leu Glu Leu Glu Leu Cys Pro Gly Arg Trp Val Gly Gly Gln His
1               5                   10                  15

Pro Cys Phe Ile Ile Ala Glu Ile Gly Gln Asn His Gln Gly Asp Leu
            20                  25                  30

Asp Val Ala Lys Arg Met Ile Arg Met Ala Lys Glu Cys Gly Ala Asp
            35                  40                  45

Cys Ala Lys Phe Gln Lys Ser Glu Leu Glu Phe Lys Phe Asn Arg Lys
        50                  55                  60

Ala Leu Glu Arg Pro Tyr Thr Ser Lys His Ser Trp Gly Lys Thr Tyr
65                  70                  75                  80

Gly Glu His Lys Arg His Leu Glu Phe Ser His Asp Gln Tyr Arg Glu
                85                  90                  95

Leu Gln Arg Tyr Ala Glu Glu Val Gly Ile Phe Phe Thr Ala Ser Gly
            100                 105                 110

Met Asp Glu Met Ala Val Glu Phe Leu His Glu Leu Asn Val Pro Phe
        115                 120                 125

Phe Lys Val Gly Ser Gly Asp Thr Asn Asn Phe Pro Tyr Leu Glu Lys
    130                 135                 140

Thr Ala Lys Lys Gly Arg Pro Met Val Ile Ser Ser Gly Met Gln Ser
145                 150                 155                 160

Met Asp Thr Met Lys Gln Val Tyr Gln Ile Val Lys Pro Leu Asn Pro
                165                 170                 175

Asn Phe Cys Phe Leu Gln Cys Thr Ser Ala Tyr Pro Leu Gln Pro Glu
            180                 185                 190

Asp Val Asn Leu Arg Val Ile Ser Glu Tyr Gln Lys Leu Phe Pro Asp
        195                 200                 205

Ile Pro Ile Gly Tyr Ser Gly His Glu Thr Gly Ile Ala Ile Ser Val
    210                 215                 220

Ala Ala Val Ala Leu Gly Ala Lys Val Leu Glu Arg His Ile Thr Leu
225                 230                 235                 240

Asp Lys Thr Trp Lys Gly Ser Asp His Ser Ala Ser Leu Glu Pro Gly
                245                 250                 255

Glu Leu Ala Glu Leu Val Arg Ser Val Arg Leu Val Glu Arg Ala Leu
            260                 265                 270

Gly Ser Pro Thr Lys Gln Leu Leu Pro Cys Glu Met Ala Cys Asn Glu
        275                 280                 285
```

```
Lys Leu Gly Lys Ser Val Val Ala Lys Val Ile Pro Glu Gly Thr
        290                 295                 300
Ile Leu Thr Met Asp Met Leu Thr Val Lys Val Gly Glu Pro Lys Gly
305                 310                 315                 320
Tyr Pro Pro Glu Asp Ile Phe Asn Leu Val Gly Lys Lys Val Leu Val
                    325                 330                 335
Thr Val Glu Glu Asp Asp Thr Ile Met Glu Glu Leu Val Asp Asn His
                340                 345                 350
Gly Lys Lys Ile Lys Ser
            355
```

<210> SEQ ID NO 62
<211> LENGTH: 432
<212> TYPE: PRT
<213> ORGANISM: Mus musculus

<400> SEQUENCE: 62

```
Met Asp Ala Leu Glu Lys Gly Ala Val Thr Ser Gly Pro Ala Pro Arg
1               5                   10                  15
Gly Arg Pro Ser Arg Gly Arg Pro Pro Lys Leu Gln Arg Ser Arg Gly
                20                  25                  30
Ala Gly Arg Gly Leu Glu Lys Pro Pro His Leu Ala Ala Leu Val Leu
            35                  40                  45
Ala Arg Gly Gly Ser Lys Gly Ile Pro Leu Lys Asn Ile Lys Arg Leu
    50                  55                  60
Ala Gly Val Pro Leu Ile Gly Trp Val Leu Arg Ala Ala Leu Asp Ala
65                  70                  75                  80
Gly Val Phe Gln Ser Val Trp Val Ser Thr Asp His Asp Glu Ile Glu
                85                  90                  95
Asn Val Ala Lys Gln Phe Gly Ala Gln Val His Arg Arg Ser Ser Glu
                100                 105                 110
Thr Ser Lys Asp Ser Ser Thr Ser Leu Asp Ala Ile Val Glu Phe Leu
            115                 120                 125
Asn Tyr His Asn Glu Val Asp Ile Val Gly Asn Ile Gln Ala Thr Ser
    130                 135                 140
Pro Cys Leu His Pro Thr Asp Leu Gln Lys Val Ala Glu Met Ile Arg
145                 150                 155                 160
Glu Glu Gly Tyr Asp Ser Val Phe Ser Val Val Arg His Gln Phe
                165                 170                 175
Arg Trp Ser Glu Ile Gln Lys Gly Val Arg Glu Val Thr Glu Pro Leu
                180                 185                 190
Asn Leu Asn Pro Ala Lys Arg Pro Arg Arg Gln Asp Trp Asp Gly Glu
            195                 200                 205
Leu Tyr Glu Asn Gly Ser Phe Tyr Phe Ala Lys Arg His Leu Ile Glu
    210                 215                 220
Met Gly Tyr Leu Gln Gly Gly Lys Met Ala Tyr Tyr Glu Met Arg Ala
225                 230                 235                 240
Glu His Ser Val Asp Ile Asp Val Asp Ile Asp Trp Pro Ile Ala Glu
                245                 250                 255
Gln Arg Val Leu Arg Phe Gly Tyr Phe Gly Lys Glu Leu Lys Glu
                260                 265                 270
Ile Lys Leu Leu Val Cys Asn Ile Asp Gly Cys Leu Thr Asn Gly His
            275                 280                 285
Ile Tyr Val Ser Gly Asp Gln Lys Glu Ile Ile Ser Tyr Asp Val Lys
    290                 295                 300
```

```
Asp Ala Ile Gly Ile Ser Leu Leu Lys Lys Ser Gly Ile Glu Val Arg
305                 310                 315                 320

Leu Ile Ser Glu Arg Ala Cys Ser Lys Gln Thr Leu Ser Ala Leu Lys
                325                 330                 335

Leu Asp Cys Lys Thr Glu Val Ser Val Ser Asp Lys Leu Ala Thr Val
            340                 345                 350

Asp Glu Trp Arg Lys Glu Met Gly Leu Cys Trp Lys Glu Val Ala Tyr
        355                 360                 365

Leu Gly Asn Glu Val Ser Asp Glu Cys Leu Lys Arg Val Gly Leu
    370                 375                 380

Ser Ala Val Pro Ala Asp Ala Cys Ser Gly Ala Gln Lys Ala Val Gly
385                 390                 395                 400

Tyr Ile Cys Lys Cys Ser Gly Gly Arg Gly Ala Ile Arg Glu Phe Ala
                405                 410                 415

Glu His Ile Phe Leu Leu Ile Glu Lys Val Asn Asn Ser Cys Gln Lys
                420                 425                 430
```

<210> SEQ ID NO 63
<211> LENGTH: 434
<212> TYPE: PRT
<213> ORGANISM: Homo sapiens

<400> SEQUENCE: 63

```
Met Asp Ser Val Glu Lys Gly Ala Ala Thr Ser Val Ser Asn Pro Arg
1               5                   10                  15

Gly Arg Pro Ser Arg Gly Arg Pro Pro Lys Leu Gln Arg Asn Ser Arg
                20                  25                  30

Gly Gly Gln Gly Arg Gly Val Glu Lys Pro Pro His Leu Ala Ala Leu
            35                  40                  45

Ile Leu Ala Arg Gly Gly Ser Lys Gly Ile Pro Leu Lys Asn Ile Lys
        50                  55                  60

His Leu Ala Gly Val Pro Leu Ile Gly Trp Val Leu Arg Ala Ala Leu
65                  70                  75                  80

Asp Ser Gly Ala Phe Gln Ser Val Trp Val Ser Thr Asp His Asp Glu
                85                  90                  95

Ile Glu Asn Val Ala Lys Gln Phe Gly Ala Gln Val His Arg Arg Ser
                100                 105                 110

Ser Glu Val Ser Lys Asp Ser Ser Thr Ser Leu Asp Ala Ile Ile Glu
            115                 120                 125

Phe Leu Asn Tyr His Asn Glu Val Asp Ile Val Gly Asn Ile Gln Ala
        130                 135                 140

Thr Ser Pro Cys Leu His Pro Thr Asp Leu Gln Lys Val Ala Glu Met
145                 150                 155                 160

Ile Arg Glu Glu Gly Tyr Asp Ser Val Phe Ser Val Val Arg His
                165                 170                 175

Gln Phe Arg Trp Ser Glu Ile Gln Lys Gly Val Arg Glu Val Thr Glu
                180                 185                 190

Pro Leu Asn Leu Asn Pro Ala Lys Arg Pro Arg Arg Gln Asp Trp Asp
            195                 200                 205

Gly Glu Leu Tyr Glu Asn Gly Ser Phe Tyr Phe Ala Lys Arg His Leu
        210                 215                 220

Ile Glu Met Gly Tyr Leu Gln Gly Gly Lys Met Ala Tyr Tyr Glu Met
225                 230                 235                 240

Arg Ala Glu His Ser Val Asp Ile Asp Val Asp Ile Asp Trp Pro Ile
                245                 250                 255
```

Ala Glu Gln Arg Val Leu Arg Tyr Gly Tyr Phe Gly Lys Glu Lys Leu
            260                 265                 270

Lys Glu Ile Lys Leu Leu Val Cys Asn Ile Asp Gly Cys Leu Thr Asn
        275                 280                 285

Gly His Ile Tyr Val Ser Gly Asp Gln Lys Glu Ile Ile Ser Tyr Asp
        290                 295                 300

Val Lys Asp Ala Ile Gly Ile Ser Leu Leu Lys Lys Ser Gly Ile Glu
305                 310                 315                 320

Val Arg Leu Ile Ser Glu Arg Ala Cys Ser Lys Gln Thr Leu Ser Ser
                325                 330                 335

Leu Lys Leu Asp Cys Lys Met Glu Val Ser Val Ser Asp Lys Leu Ala
                340                 345                 350

Val Val Asp Glu Trp Arg Lys Glu Met Gly Leu Cys Trp Lys Glu Val
            355                 360                 365

Ala Tyr Leu Gly Asn Glu Val Ser Asp Glu Cys Leu Lys Arg Val
        370                 375                 380

Gly Leu Ser Gly Ala Pro Ala Asp Ala Cys Ser Thr Ala Gln Lys Ala
385                 390                 395                 400

Val Gly Tyr Ile Cys Lys Cys Asn Gly Gly Arg Gly Ala Ile Arg Glu
                405                 410                 415

Phe Ala Glu His Ile Cys Leu Leu Met Glu Lys Val Asn Asn Ser Cys
            420                 425                 430

Gln Lys

<210> SEQ ID NO 64
<211> LENGTH: 336
<212> TYPE: PRT
<213> ORGANISM: Mus musculus

<400> SEQUENCE: 64

Met Ala Pro Ala Arg Glu Asn Val Ser Leu Phe Phe Lys Leu Tyr Cys
1               5                   10                  15

Leu Ala Val Met Thr Leu Val Ala Ala Tyr Thr Val Ala Leu Arg
            20                  25                  30

Tyr Thr Arg Thr Thr Ala Glu Glu Leu Tyr Phe Ser Thr Thr Ala Val
        35                  40                  45

Cys Ile Thr Glu Val Ile Lys Leu Leu Ile Ser Val Gly Leu Leu Ala
    50                  55                  60

Lys Glu Thr Gly Ser Leu Gly Arg Phe Lys Ala Ser Leu Ser Glu Asn
65                  70                  75                  80

Val Leu Gly Ser Pro Lys Glu Leu Ala Lys Leu Ser Val Pro Ser Leu
                85                  90                  95

Val Tyr Ala Val Gln Asn Asn Met Ala Phe Leu Ala Leu Ser Asn Leu
                100                 105                 110

Asp Ala Ala Val Tyr Gln Val Thr Tyr Gln Leu Lys Ile Pro Cys Thr
            115                 120                 125

Ala Leu Cys Thr Val Leu Met Leu Asn Arg Thr Leu Ser Lys Leu Gln
        130                 135                 140

Trp Ile Ser Val Phe Met Leu Cys Gly Val Thr Leu Val Gln Trp
145                 150                 155                 160

Lys Pro Ala Gln Ala Ser Lys Val Val Ala Gln Asn Pro Leu Leu
                165                 170                 175

Gly Phe Gly Ala Ile Ala Ile Ala Val Leu Cys Ser Gly Phe Ala Gly
            180                 185                 190

```
Val Tyr Phe Glu Lys Val Leu Lys Ser Ser Asp Thr Ser Leu Trp Val
        195                 200                 205

Arg Asn Ile Gln Met Tyr Leu Ser Gly Ile Val Thr Leu Ala Gly
    210                 215                 220

Thr Tyr Leu Ser Asp Gly Ala Glu Ile Gln Glu Lys Gly Phe Phe Tyr
225                 230                 235                 240

Gly Tyr Thr Tyr Tyr Val Trp Phe Val Ile Phe Leu Ala Ser Val Gly
                245                 250                 255

Gly Leu Tyr Thr Ser Val Val Lys Tyr Thr Asp Asn Ile Met Lys
            260                 265                 270

Gly Phe Ser Ala Ala Ala Ile Val Leu Ser Thr Ile Ala Ser Val
    275                 280                 285

Leu Leu Phe Gly Leu Gln Ile Thr Leu Ser Phe Ala Leu Gly Ala Leu
290                 295                 300

Leu Val Cys Val Ser Ile Tyr Leu Tyr Gly Leu Pro Arg Gln Asp Thr
305                 310                 315                 320

Thr Ser Ile Gln Gln Glu Ala Thr Ser Lys Glu Arg Ile Ile Gly Val
                325                 330                 335

<210> SEQ ID NO 65
<211> LENGTH: 337
<212> TYPE: PRT
<213> ORGANISM: Homo sapiens

<400> SEQUENCE: 65

Met Ala Ala Pro Arg Asp Asn Val Thr Leu Leu Phe Lys Leu Tyr Cys
1               5                   10                  15

Leu Ala Val Met Thr Leu Met Ala Ala Val Tyr Thr Ile Ala Leu Arg
            20                  25                  30

Tyr Thr Arg Thr Ser Asp Lys Glu Leu Tyr Phe Ser Thr Thr Ala Val
        35                  40                  45

Cys Ile Thr Glu Val Ile Lys Leu Leu Leu Ser Val Gly Ile Leu Ala
    50                  55                  60

Lys Glu Thr Gly Ser Leu Gly Arg Phe Lys Ala Ser Leu Arg Glu Asn
65                  70                  75                  80

Val Leu Gly Ser Pro Lys Glu Leu Leu Lys Leu Ser Val Pro Ser Leu
                85                  90                  95

Val Tyr Ala Val Gln Asn Asn Met Ala Phe Leu Ala Leu Ser Asn Leu
                100                 105                 110

Asp Ala Ala Val Tyr Gln Val Thr Tyr Gln Leu Lys Ile Pro Cys Thr
            115                 120                 125

Ala Leu Cys Thr Val Leu Met Leu Asn Arg Thr Leu Ser Lys Leu Gln
    130                 135                 140

Trp Val Ser Val Phe Met Leu Cys Ala Gly Val Thr Leu Val Gln Trp
145                 150                 155                 160

Lys Pro Ala Gln Ala Thr Lys Val Val Glu Gln Asn Pro Leu Leu
                165                 170                 175

Gly Phe Gly Ala Ile Ala Ile Ala Val Leu Cys Ser Gly Phe Ala Gly
                180                 185                 190

Val Tyr Phe Glu Lys Val Leu Lys Ser Ser Asp Thr Ser Leu Trp Val
                195                 200                 205

Arg Asn Ile Gln Met Tyr Leu Ser Gly Ile Val Thr Leu Ala Gly
    210                 215                 220

Val Tyr Leu Ser Asp Gly Ala Glu Ile Lys Glu Lys Gly Phe Phe Tyr
225                 230                 235                 240
```

-continued

Gly Tyr Thr Tyr Tyr Val Trp Phe Val Ile Phe Leu Ala Ser Val Gly
                245                 250                 255

Gly Leu Tyr Thr Ser Val Val Lys Tyr Thr Asp Asn Ile Met Lys
            260                 265                 270

Gly Phe Ser Ala Ala Ala Ile Val Leu Ser Thr Ile Ala Ser Val
        275                 280                 285

Met Leu Phe Gly Leu Gln Ile Thr Leu Thr Phe Ala Leu Gly Thr Leu
290                 295                 300

Leu Val Cys Val Ser Ile Tyr Leu Tyr Gly Leu Pro Arg Gln Asp Thr
305                 310                 315                 320

Thr Ser Ile Gln Gln Gly Glu Thr Ala Ser Lys Glu Arg Val Ile Gly
                325                 330                 335

Val

<210> SEQ ID NO 66
<211> LENGTH: 398
<212> TYPE: PRT
<213> ORGANISM: Homo sapiens

<400> SEQUENCE: 66

Met Arg Leu Arg Glu Pro Leu Leu Ser Gly Ser Ala Ala Met Pro Gly
1               5                   10                  15

Ala Ser Leu Gln Arg Ala Cys Arg Leu Leu Val Ala Val Cys Ala Leu
                20                  25                  30

His Leu Gly Val Thr Leu Val Tyr Tyr Leu Ala Gly Arg Asp Leu Ser
            35                  40                  45

Arg Leu Pro Gln Leu Val Gly Val Ser Thr Pro Leu Gln Gly Gly Ser
50                  55                  60

Asn Ser Ala Ala Ala Ile Gly Gln Ser Ser Gly Glu Leu Arg Thr Gly
65                  70                  75                  80

Gly Ala Arg Pro Pro Pro Pro Leu Gly Ala Ser Ser Gln Pro Arg Pro
                85                  90                  95

Gly Gly Asp Ser Ser Pro Val Val Asp Ser Gly Pro Gly Pro Ala Ser
            100                 105                 110

Asn Leu Thr Ser Val Pro Val Pro His Thr Thr Ala Leu Ser Leu Pro
        115                 120                 125

Ala Cys Pro Glu Glu Ser Pro Leu Leu Val Gly Pro Met Leu Ile Glu
130                 135                 140

Phe Asn Met Pro Val Asp Leu Glu Leu Val Ala Lys Gln Asn Pro Asn
145                 150                 155                 160

Val Lys Met Gly Gly Arg Tyr Ala Pro Arg Asp Cys Val Ser Pro His
                165                 170                 175

Lys Val Ala Ile Ile Ile Pro Phe Arg Asn Arg Gln Glu His Leu Lys
            180                 185                 190

Tyr Trp Leu Tyr Tyr Leu His Pro Val Leu Gln Arg Gln Gln Leu Asp
        195                 200                 205

Tyr Gly Ile Tyr Val Ile Asn Gln Ala Gly Asp Thr Ile Phe Asn Arg
210                 215                 220

Ala Lys Leu Leu Asn Val Gly Phe Gln Glu Ala Leu Lys Asp Tyr Asp
225                 230                 235                 240

Tyr Thr Cys Phe Val Phe Ser Asp Val Asp Leu Ile Pro Met Asn Asp
                245                 250                 255

His Asn Ala Tyr Arg Cys Phe Ser Gln Pro Arg His Ile Ser Val Ala
            260                 265                 270

-continued

Met Asp Lys Phe Gly Phe Ser Leu Pro Tyr Val Gln Tyr Phe Gly Gly
            275                 280                 285

Val Ser Ala Leu Ser Lys Gln Gln Phe Leu Thr Ile Asn Gly Phe Pro
    290                 295                 300

Asn Asn Tyr Trp Gly Trp Gly Gly Glu Asp Asp Ile Phe Asn Arg
305                 310                 315                 320

Leu Val Phe Arg Gly Met Ser Ile Ser Arg Pro Asn Ala Val Val Gly
                325                 330                 335

Arg Cys Arg Met Ile Arg His Ser Arg Asp Lys Lys Asn Glu Pro Asn
                340                 345                 350

Pro Gln Arg Phe Asp Arg Ile Ala His Thr Lys Glu Thr Met Leu Ser
                355                 360                 365

Asp Gly Leu Asn Ser Leu Thr Tyr Gln Val Leu Asp Val Gln Arg Tyr
            370                 375                 380

Pro Leu Tyr Thr Gln Ile Thr Val Asp Ile Gly Thr Pro Ser
385                 390                 395

<210> SEQ ID NO 67
<211> LENGTH: 346
<212> TYPE: PRT
<213> ORGANISM: Mus musculus

<400> SEQUENCE: 67

Met Arg Phe Arg Glu Gln Phe Leu Gly Gly Ser Ala Ala Met Pro Gly
1               5                   10                  15

Ala Thr Leu Gln Arg Ala Cys Arg Leu Leu Val Ala Val Cys Ala Leu
            20                  25                  30

His Leu Gly Val Thr Leu Val Tyr Tyr Leu Ser Gly Arg Asp Leu Ser
        35                  40                  45

Arg Leu Pro Gln Leu Val Gly Val Ser Ser Thr Leu Gln Gly Gly Thr
    50                  55                  60

Asn Gly Ala Ala Ala Ser Lys Gln Pro Gly Glu Gln Arg Pro Arg
65                  70                  75                  80

Gly Ala Arg Pro Pro Pro Leu Gly Val Ser Pro Lys Pro Arg Pro
                85                  90                  95

Gly Leu Asp Ser Ser Pro Gly Ala Ala Ser Gly Pro Gly Leu Lys Ser
            100                 105                 110

Asn Leu Ser Ser Leu Pro Val Pro Thr Thr Gly Leu Leu Ser Leu
        115                 120                 125

Pro Ala Cys Pro Glu Glu Ser Pro Leu Leu Val Gly Pro Met Leu Ile
    130                 135                 140

Asp Phe Asn Ile Ala Val Asp Leu Glu Leu Leu Ala Lys Lys Asn Pro
145                 150                 155                 160

Glu Ile Lys Thr Gly Gly Arg Tyr Ser Pro Lys Asp Cys Val Ser Pro
                165                 170                 175

His Lys Val Ala Ile Ile Ile Pro Phe Arg Asn Arg Gln Glu His Leu
            180                 185                 190

Lys Tyr Trp Leu Tyr Tyr Leu His Pro Ile Leu Gln Arg Gln Gln Leu
        195                 200                 205

Asp Tyr Gly Ile Tyr Val Ile Asn Gln Ala Gly Asp Thr Met Phe Asn
    210                 215                 220

Arg Ala Lys Leu Leu Asn Ile Gly Phe Gln Glu Ala Leu Lys Asp Tyr
225                 230                 235                 240

Asp Tyr Asn Cys Phe Val Phe Ser Asp Val Asp Leu Ile Pro Met Asp
                245                 250                 255

```
                            -continued
Asp Arg Asn Ala Tyr Arg Cys Phe Ser Gln Pro Arg His Ile Ser Val
            260                 265             270

Ala Met Asp Lys Phe Gly Phe Ser Leu Pro Tyr Val Gln Tyr Phe Gly
        275             280             285

Gly Val Ser Ala Leu Ser Lys Gln Gln Phe Leu Ala Ile Asn Gly Phe
    290             295             300

Pro Asn Asn Tyr Trp Gly Trp Gly Gly Glu Asp Asp Asp Ile Phe Asn
305             310             315                         320

Arg Ser Lys Pro Lys Ala Ser Ala Glu Glu Thr Gly Gly Ser Leu Gly
            325             330             335

Lys Ala Leu Ser Pro Ala Ser Thr Arg Ala
            340             345
```

PRODUCTION OF GLYCOSYLATED POLYPEPTIDES IN MICRO ALGAE

FIELD OF THE INVENTION

The present invention is directed to methods for producing glycosylated proteins (glycoproteins) in microalgae, said glycosylated polypeptides having patterns of glycosylation suitable for therapeutic purposes.

BACKGROUND OF THE INVENTION

After DNA is transcribed and translated into a protein, further post-translational processing involves the attachment of sugar residues, a process known as glycosylation. Different organisms produce different glycosylation enzymes (glycosyltransferases and glycosidases), and have different substrates (nucleotide sugars) available, so that the glycosylation patterns as well as composition of the individual oligosaccharides, even of the same protein, will be different depending on the host system in which the particular protein is being expressed. Bacteria typically do not glycosylate proteins, and if so only in a very unspecific manner. Lower eukaryotes such as filamentous fungi and yeast add primarily mannose and mannosylphosphate sugars. The resulting glycan is known as a "poly-mannose" type glycan or a mannan.

By contrast, in higher eukaryotes such as humans, plant cells and insect cells, the nascent oligosaccharide side chain may be trimmed to remove several mannose residues and elongated with additional sugar residues that typically are not found in the N-glycans of lower eukaryotes such as filamentous fungi and yeast. This synthesis begins with a set of sequential reactions in the course of which sugar residues are added and removed while the protein moves along the secretory pathway in the host organism. However, enzymes which reside in the Golgi apparatus of the host organism or cell differ in their specificities and thus determine the resulting glycosylation patterns of secreted proteins.

Thus, the resulting glycosylation pattern of proteins expressed in eukaryotic host cells such as yeast, plants or insects, differs substantially from the glycosylation pattern of proteins expressed in humans and other mammals.

The early steps of the mammalian protein glycosylation can be divided into at least four different phases:
(i) lipid-linked $Glc_3Man_9GlcNAc_2$ oligosaccharides are assembled by a sequential set of reactions at the membrane of the endoplasmic reticulum (ER) and
(ii) transfer of this oligosaccharide from the lipid anchor dolichol pyrophosphate onto de novo synthesized protein. The site of the specific transfer is defined by an asparagine (Asn) residue in the sequence Asn-Xaa-Ser/Thr where Xaa can be any amino acid except proline and aspartic acid.
(iii) Further processing by glucosidases and mannosidases occurs in the ER before the nascent glycoprotein is transferred to the cis-Golgi apparatus, where additional mannose residues are removed by Golgi specific α1,2-mannosidases.
(iv) Processing continues as the protein proceeds through the Golgi apparatus. In the median-Golgi, a number of modifying enzymes, including N-acetylglucosaminyltransferases (GnTI, GnTII, GnTIII, GnTIV and GnTV), mannosidase II and fucosyltransferases, add and remove specific sugar residues. Finally, in the trans-Golgi, galactosyltranferases (GalT) and sialyltransferases (ST) produce a glycoprotein structure that is released from the Golgi. It is this structure, characterized by bi-, tri- and tetra-antennary structures, containing galactose, fucose, N-acetylglucosamine and a high degree of terminal sialic acid that gives glycoproteins their mammalian characteristics.

In nearly all eukaryotes, glycoproteins are derived from a common lipid-linked oligosaccharide precursor $Glc_3Man_9GlcNAc_2$-dolichol-pyrophosphate. Within the endoplasmic reticulum, synthesis and processing of dolichol pyrophosphate bound oligosaccharides are identical between all known eukaryotes.

However, further processing of the core oligosaccharide by fungal, plant or insect cells once it has been transferred to a peptide leaving the ER and entering the Golgi, differs significantly from humans as it moves along the secretory pathway and involves in the Golgi apparatus the addition of several organism-specific sugars.

A significant fraction of proteins isolated from humans or other animals are glycosylated. Among proteins used therapeutically, about 70% are glycosylated. If a therapeutic protein is produced in an organism host such as yeast or fungus, however, and is glycosylated utilizing the endogenous pathway, its therapeutic efficiency is typically greatly reduced. Such glycoproteins are typically immunogenic in humans and show a reduced half-life in vivo after administration. Specific receptors in humans and animals can recognize terminal mannose residues and promote the rapid clearance of the protein from the bloodstream. Additional adverse effects may include changes in protein folding, solubility, susceptibility to proteases, trafficking, transport, compartmentalization, secretion, biological activity, recognition by other proteins or factors, antigenicity, or allergenicity. Accordingly, it has been necessary to produce therapeutic glycoproteins in animal host systems, so that the pattern of glycosylation is identical or at least similar to that, in humans or in the intended recipient species. In most cases a mammalian host system, such as mammalian cell culture, is used.

In order to produce therapeutic proteins that have appropriate glycoforms and have satisfactory therapeutic effects, animal or plant-based expression systems have been used. The available systems include:
Chinese Hamster Ovary cells (CHO), mouse fibroblast cells and mouse myeloma cells;
transgenic animals such as goats, sheep, mice and others;
yeast (such as *S. pombe, S. cerevisiae, P. pastoris*), bacteria (such as *E. coli*), fungi (such as *A. nidulans, T ressei*);— plants (such as *A. thaliana, N. tabacum, M. sativa* etc.);
insect cells (such as *S. frugiperda* Sf9, Sf21, *Trichoplusia ni*, etc. in combination with recombinant baculoviinses such as *A. californica* multiple nuclear polyhedrosis virus which infects lepidopteran cells).

Recombinant human proteins expressed in the above-mentioned host systems may still include non-human glycoforms. In particular, fraction of the N-glycans may lack terminal sialic acid, typically found in human glycoproteins. Substantial efforts have been directed to develop processes to obtain glycoproteins that are as close as possible in structure to the human forms, or have other therapeutic advantages such as having specific glycoforms that may be especially useful, for example in the targeting of therapeutic proteins. For example, the addition of one or more sialic acid residues to a glycan side chain may increase the lifetime of a therapeutic glycoprotein in vivo after administration. Accordingly, the mammalian host cells may be genetically engineered to increase the extent of terminal sialic acid in glycoproteins expressed in the cells. Alternatively sialic acid may be conjugated to the protein of interest in vitro prior to administration using a sialyltransferase and an appropriate substrate. In addition, changes in growth medium composition or the expression of enzymes involved in human glycosylation have been employed to produce glycoproteins more closely resembling to the human forms. Alternatively cultured human cells may be used.

However, all of the existing systems have significant drawbacks. Only certain therapeutic proteins are suitable for expression in animal or plant systems (e.g. those lacking in any cytotoxic effect or other effect adverse to growth).

Animal and plant cell culture systems may be very slow, frequently requiring up to a week of growth under carefully controlled conditions to produce any useful quantity of the protein of interest. Protein yields nonetheless compare unfavorably with those from microbial fermentation processes. In addition, animal cell culture systems typically require complex and expensive nutrients and cofactors, such as bovine fetal serum. Furthermore growth may be limited by programmed cell death (apoptosis).

Moreover, animal cells (particularly mammalian cells) are highly susceptible to viral infection or contamination. In some cases, virus or other infectious agent may just compromise the growth of the culture, while in other cases; this agent may be a human pathogen rendering the therapeutic protein product unfit for its intended use. Furthermore many cell culture processes require the use of complex, temperature-sensitive, animal-derived growth media components, which may carry pathogens such as bovine spongiform encephalopathy (BSE) prions. Such pathogens are difficult to detect and/or difficult to remove or sterilize without compromising the growth medium. In any case, use of animal cells to produce therapeutic proteins necessitates costly quality controls to assure product safety.

Transgenic animals may also be used for manufacturing high-volume of therapeutic proteins such as human serum albumin, tissue plasminogen activator, monoclonal antibodies, hemoglobin, collagen, fibrinogen and others. While transgenic goats and other transgenic animals (mice, sheep, cows, etc.) can be genetically engineered to produce therapeutic proteins at high concentrations in the milk, the process is costly since every batch has to undergo rigorous quality control. Animals may host a variety of animal or human pathogens, including bacteria, viruses, fungi, and prions. In the case of scrapies and bovine spongiform encephalopathy, testing can take about a year to rule out infection. The production of therapeutic compounds is thus preferably carried out in a well-controlled sterile environment, e.g. under Good Manufacturing Practice (GMP) conditions. However, it is not generally feasible to maintain animals in such environments. Moreover, whereas cells grown in a fermenter are derived from one well characterized Master Cell Bank (MCB), transgenic animal technology relies on different animals and thus is inherently non-uniform. Furthermore external factors such as different food uptake, disease and lack of homogeneity within a herd, may effect glycosylation patterns of the final product. It is known in humans, for example, that different dietary habits result in differing glycosylation patterns.

Transgenic plants have been developed as a potential source to obtain proteins of therapeutic value. However, high level expression of proteins in plants suffers from gene silencing, a mechanism by which the genes for highly expressed proteins are down-regulated in subsequent plant generations. In addition, plants add $\beta(1,2)$-linked xylose and/or $\alpha(1,3)$-linked fucose to protein N-glycans, resulting in glycoproteins that differ in structure from animals and are immunogenic in mammals. Furthermore, it is generally not practical to grow plants in a sterile or GMP environment, and the recovery of proteins from plant tissues is more costly than the recovery from fermented microorganisms.

Transgenic yeast or fungi systems also present the drawback of expressing mannosyltransferase genes which adds a mannose to the glycan structure and leads to hypermannosylated proteins.

In conclusion, all different systems described here above present important drawbacks in terms of immunogenicity of the glycosylated proteins produced.

An object of the invention is therefore to provide an alternative and effective system for producing recombinant glycoproteins having a glycosylation pattern suitable for therapeutic purpose.

The Applicant found surprisingly that microalgae such as *Phaeodactylum tricornutum* (*P. tricornutum*) are capable of producing polypeptides harbouring $Man_5GlcNAc_2$ to $Man_9GlcNA_2$ via their endogenous N-glycosylation machinery. Analysis of N-glycans from other representative microalgae also revealed the presence of high-mannose-type oligosaccharides on their proteins. Thus, microalgae present the advantage to allow the production of proteins with a certain glycosylation pattern without needing the suppression of genes responsible for the addition of immunogenic epitopes such as in plants or yeasts. This discovery was unexpected since microalgae were thought to produce proteins having a plant glycosylation pattern and, eventually, a yeast or fungi glycosylation pattern. This idea is well illustrated by the patent application PCT WO 2006/013572 which discloses the production of a glycosylated Hepatitis B S antigen (HBsAg) in red microalgae and suggests to "humanize" the glycosylation pattern of recombinants products synthesized in red microalgae (page 16, lines 4 to 8) by:

inactivating in said microalgae α-mannosidase I and N-acetylglucosaminyltransferase (page 16, line 29-33), which enzymes are implicated in yeast and in fungi in the addition of a mannose to the glycan structure leading to hypermannosylated proteins); and inactivating $\alpha(1,3)$-fucosyltransferase and $\beta(1,2)$-xylosyltransferase (page 17, lines 16-22 and lines 1-5), which enzymes are implicated in plants in the addition of $\beta(1,2)$-linked xylose and $\alpha(1,3)$-linked fucose to protein N-glycans.

Microalgae present also the advantage of being cultivated in confined photobioreactors, therefore overcoming the problem of gene dissemination into the environment and the problem of virus transmission to animals. In addition, microalgae culture system is very fast, provides an excellent yield in biomass and only requires sea water or fresh water, nutritive elements, carbon and light.

SUMMARY OF THE INVENTION

The invention related to transformed microalgae comprising a nucleotide sequence operably linked to a promoter that drives expression in said microalgae, wherein said nucleotide sequence encodes a glycosylated polypeptide that is expressed in the transformed microalgae.

In a preferred embodiment, said microalgae allows the production of said glycosylated polypeptide with a glycosylation pattern suitable for therapeutic purpose in animals without needing the suppression of genes responsible for the addition of immunogenic epitopes such as in plants, which add $\beta(1,2)$-linked xylose and/or $\alpha(1,3)$-linked fucose to protein N-glycans resulting in glycoproteins that differ in structure from animals and are immunogenic in mammals, or yeasts which express mannosyltransferase genes adding a mannose to the glycan structure and leading to hypermannosylated proteins. Preferably, said microalgae does not share any beta (1,2)-xylosyl transferase and/or alpha (1,3) fucosyl transferase activity before being transformed.

Preferably, said microalgae does not share any mannosyltransferase activity leading to hypermannosylated proteins resulting from the addition of mannose to the glycan structure as observed in yeast and in fungi.

In particular, said glycosylated polypeptide expressed in the transformed microalgae comprises a glycosylation pattern suitable for therapeutic purposes.

In a preferred embodiment, said glycosylated polypeptide expressed in the transformed microalgae comprises at least one $Man_5GlcNAc_2$ structure.

In an embodiment of the invention, said microalgae are selected among green algae, red algae, chromalveolates, and euglenids; preferably, said microalgae are selected among Chlorophytes, Euglenids, Haptophytes, Prasinophytes and Diatoms.

In another embodiment of the invention, the glycosylated polypeptide is selected from the group comprising a polypeptide having a primary amino acid sequence of a human glycosylated polypeptide, a primary amino acid sequence of a non-human glycosylated polypeptide, a primary amino acid sequence of an antibody or an active fragment thereof, and/or a primary amino acid sequence of a non-mammalian glycosylated polypeptide.

In a preferred embodiment of the invention, the glycosylated polypeptide is an animal, mammalian or a human polypeptide.

In another embodiment of the invention, said transformed microalgae further comprise a nucleotide sequence operably linked to a promoter that drives expression in said microalgae, wherein said nucleotide sequence encodes an N-acetylglucosaminyltransferase I enzyme that is expressed in the transformed microalgae.

In another embodiment of the invention, said transformed microalgae further comprise a nucleotide sequence operably linked to a promoter that drives expression in said microalgae, wherein said nucleotide sequence encodes a mannosidase II that is expressed in the transformed microalgae.

In another embodiment of the invention, said transformed microalgae further comprise a nucleotide sequence operably linked to a promoter that drives expression in said microalgae, wherein said nucleotide sequence encodes a N-acetylglucosaminyltransferase II enzyme that is expressed in the transformed microalgae.

In another embodiment of the invention, said transformed microalgae further comprise a nucleotide sequence operably linked to a promoter that drives expression in said microalgae, wherein said nucleotide sequence encodes at least one enzyme selected among N-acetylglucosaminyltransferase II, III, IV, V and VI that is expressed in the transformed microalgae.

In another embodiment of the invention, said transformed microalgae further comprise a nucleotide sequence operably linked to a promoter that drives expression in said microalgae, wherein said nucleotide sequence encodes at least one glycosyltransferase enzyme selected among galactosyltransferase, fucosyltransferase and sialyltransferases, that is expressed in the transformed microalgae.

In another embodiment of the invention, said nucleotide sequence, operably linked to a promoter that drives expression of N-acetylglucosaminyltransferases, mannosidase II or glycosyltransferases in said microalgae, comprises said enzyme catalytic domain having optimal activity in said ER and Golgi at a pH between 5.1 and 8, fused to a cellular targeting signal not normally associated with the catalytic domain.

Another object of the invention is transformed microalgae comprising a nucleotide sequence operably linked to a promoter that drives expression in said microalgae, wherein said nucleotide sequence encodes a N-acetylglucosaminyltransferase I enzyme that is expressed in the transformed microalgae.

In an embodiment of the invention, said microalgae further comprise a nucleotide sequence operably linked to a promoter that drives expression in said microalgae, wherein said nucleotide sequence encodes a mannosidase II that is expressed in the transformed microalgae.

In another embodiment of the invention, said microalgae further comprise a nucleotide sequence operably linked to a promoter that drives expression in said microalgae, wherein said nucleotide sequence encodes a N-acetylglucosaminyltransferase II enzyme that is expressed in the transformed microalgae.

In another embodiment of the invention, said microalgae further comprise a nucleotide sequence operably linked to a promoter that drives expression in said microalgae, wherein said nucleotide sequence encodes at least one enzyme selected among N-acetylglucosaminyltransferase II, III, IV, V and VI that is expressed in the transformed microalgae.

In another embodiment of the invention, said microalgae further comprise a nucleotide sequence operably linked to a promoter that drives expression in said microalgae, wherein said nucleotide sequence encodes at least one glycosyltransferase enzyme selected among galactosyltransferase, fucosyltransferase and sialyltransferases that is expressed in the transformed microalgae.

In another embodiment of the invention, said nucleotide sequences operably linked to promoters that drive expression of N-acetylglucosaminyltransferases, mannosidase II or glycosyltransferases in said microalgae, comprise said enzyme catalytic domain having optimal activity in said ER and Golgi at a pH between 5.1 and 8, fused to a cellular targeting signal not normally associated with the catalytic domain.

In another embodiment of the invention, said microalgae are selected among green algae, red algae, chromalveolates, and euglenids.

Another object of the invention is a method for producing at least one glycosylated polypeptide, comprising transforming microalgae or transformed microalgae as described here above with a nucleotide sequence operably linked to a promoter that drives expression in said microalgae, wherein said nucleotide sequence encodes a glycosylated polypeptide that is expressed in the transformed microalgae.

In another embodiment, said method comprises the step of isolating the recombinant glycosylated polypeptide subsequent to passage of said recombinant glycosylated polypeptide through the ER and Golgi apparatus of the transformed microalgae.

Another object of the invention is a method for producing transformed microalgae as described here above, comprising transforming said microalgae with a nucleotide sequence operably linked to a promoter that drives expression in said microalgae, wherein said nucleotide sequence encodes a N-acetylglucosaminyltransferase I enzyme that is expressed in the transformed microalgae.

In another embodiment, said method further comprises transforming said microalgae with a nucleotide sequence operably linked to a promoter that drives expression in said microalgae, wherein said nucleotide sequence encodes a mannosidase II enzyme that is expressed in the transformed microalgae.

In another embodiment, said method further comprises transforming said microalgae with a nucleotide sequence operably linked to a promoter that drives expression in said microalgae, wherein said nucleotide sequence encodes a N-acetylglucosaminyltransferase II enzyme that is expressed in the transformed microalgae.

In another embodiment, said method further comprises transforming said microalgae with a nucleotide sequence operably linked to a promoter that drives expression in said microalgae, wherein said nucleotide sequence encodes at least one enzyme selected among N-acetylglucosaminyltransferase II, III, IV, V and VI that is expressed in the transformed microalgae.

In another embodiment, said method further comprises transforming said microalgae with a nucleotide sequence operably linked to a promoter that drives expression in said microalgae, wherein said nucleotide sequence encodes at least one glycosyltransferase enzyme selected among galactosyltransferase, fucosyltransferase and sialyltransferases that is expressed in the transformed microalgae.

Another object of the invention is the glycosylated polypeptide produced by the method of the invention.

Another object of the invention is a pharmaceutical composition comprising the glycosylated polypeptide produced by the method of the invention.

Another object of the invention is a veterinary composition comprising the glycosylated polypeptide produced by the method of the invention.

Another object of the invention is a method for producing at least one glycosylated polypeptide, comprising: (i) transforming microalgae or transformed microalgae as defined previously with a nucleotide sequence operably linked to a promoter that drives expression in said microalgae, wherein said nucleotide sequence encodes a glycosylated polypeptide that is expressed in the transformed microalgae and (ii) purifying said at least one glycosylated polypeptide, said glycosylated polypeptide having at least one $Man_9GlcNAc_2$ to $Man_5GlcNAc_2$ structure.

Still another object of the invention is a use of a transformed microalgae as defined previously for producing a glycosylated polypeptide having at least one $Man_9GlcNAc_2$ to $Man_5GlcNAc_2$ structure.

DETAILED DESCRIPTION OF THE INVENTION

I. Definitions

Figure 1:
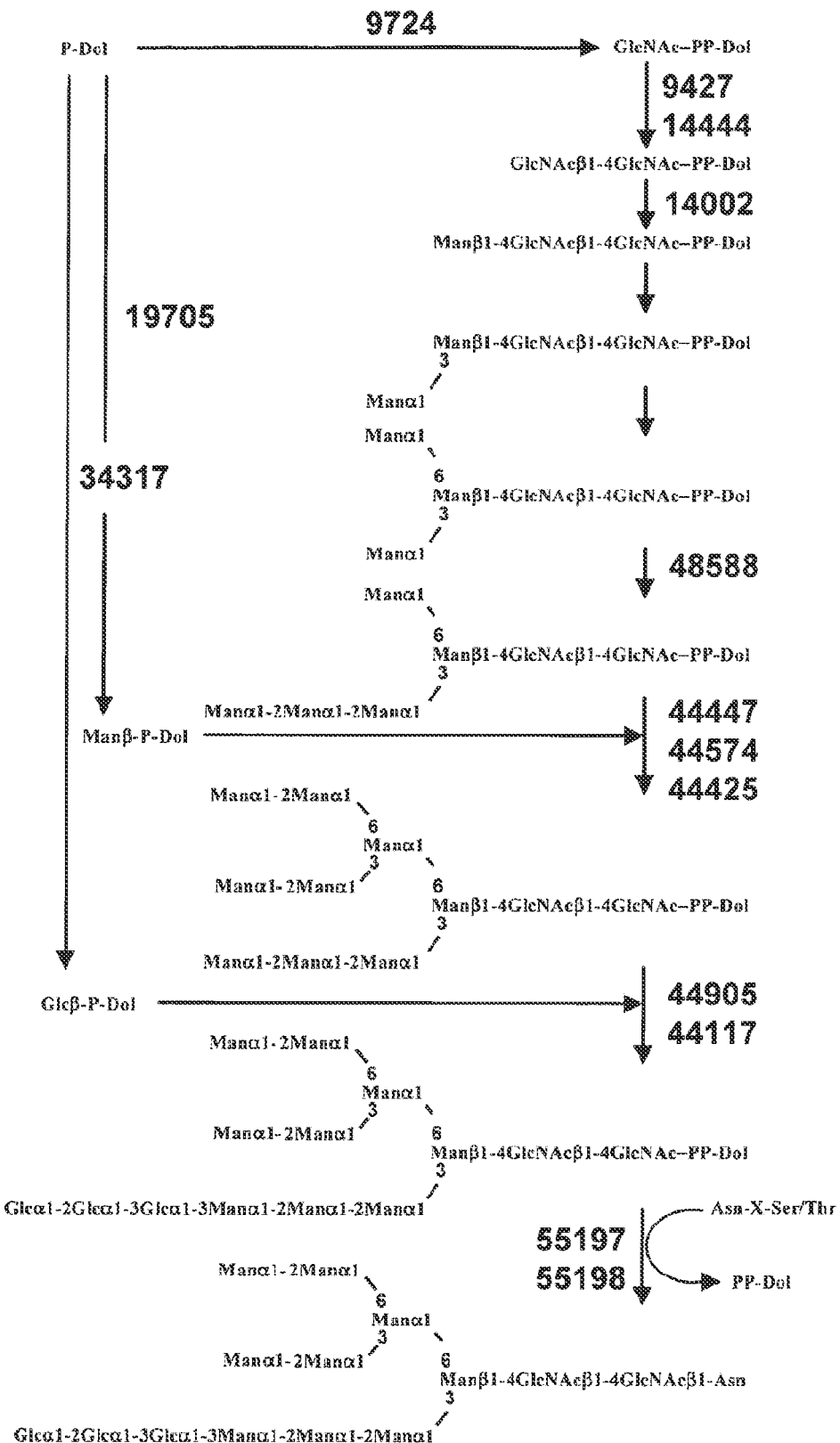
FIG. 1. N-glycosylation pathway in *Phaeodactylum tricornutum* based on bio-informatic analysis of the genome. Putative sequences identified in the *Phaeodactylum tricornutum* genome of the N-glycosylation pathway have been numbered in bold and script in this scheme. High-mannose-type N-glycans in bold were identified by structural analysis of oligosaccharides N-linked to proteins isolated from *P. tricornutum* P.t.1.8.6 fusiform strain grown in standard conditions.
Figure 1:
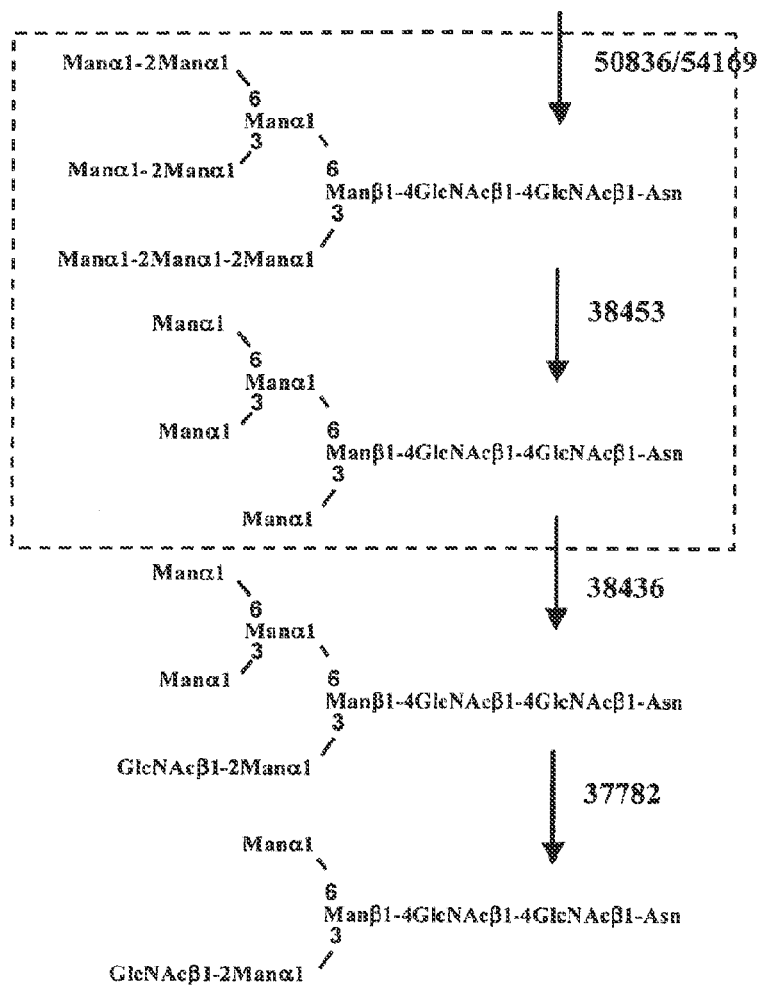

As used herein, a "glycosylated polypeptide" refers to a polypeptide with N-glycosylation.

As used herein, the term "N-glycan" refers to a N-linked oligosaccharide, e.g., one that is attached by an asparagine-N-acetylglucosamine linkage to an asparagine residue of a polypeptide. N-glycans have a common pentasaccharide core of $Man_3GlcNAc_2$ ("Man" refers to mannose; "Glc" refers to glucose; and "NAc" refers to N acetyl; GlcNAc refers to N-acetylglucosamine). The term "trimannose core" used with respect to the N-glycan also refers to the structure $Man_3GlcNAc_2$ ("Man3"). The term "pentamannose core" or "Mannose-5 core" or used with respect to the N-glycan refers to the structure $Man_5GlcNAc_2$. N-glycans differ with respect to the number of branches (antennae) comprising peripheral sugars (e.g., GlcNAc, fucose, and sialic acid) that are attached to the $Man_3$ core structure. N-glycans are classified according to their branched constituents (e.g., high mannose, complex or hybrid).

As used herein, a "high mannose" type N-glycan has five to nine mannose residues. A "poly-mannose" type N-glycan has more than nine mannose residues. A "complex" type N-glycan typically has at least one GlcNAc attached to the α1,3 mannose arm and at least one GlcNAc attached to the α1,6 mannose arm of the trimannose core. Complex N-glycans may also have galactose ("Gal") residues that are optionally modified with sialic acid or derivatives ("NeuAc", where "Neu" refers to neuraminic acid and "Ac" refers to acetyl). A complex N-glycan typically has at least one branch that terminates in an oligosaccharide such as, for example: NeuAc-; NeuAcα2-6GalNAcα1-; NeuAcα2-3Gal 1-3GalNAcα1-3; NeuAcα2-3/6Gal1-4GlcNAc1-; GlcN Acα1-4Gal1-(mucins only); Fucα1-2Gal1-(blood group H). Sulfate esters can occur on galactose, GalNAc, and GlcNAc residues, and phosphate esters can occur on mannose residues. NeuAc can be O-acetylated or replaced by NeuGc (N-glycolylneuraminic acid). Complex N glycans may also have intrachain substitutions comprising "bisecting" GlcNAc and core fucose ("Fuc"). A "hybrid" N-glycan has at least one GlcNAc on the terminal of the α1,3 mannose arm of the trimannose core and zero or more mannoses on the α1,6 mannose arm of the trimannose core.

As used herein, a "glycosylation pattern suitable for therapeutic purposes" refers to polypeptides having at least one $Man_9GlcNAc_2$ to $Man_5GlcNAc_2$ structure ($Man_9GlcNAc_2$, Man$_8$GlcNAc$_2$, Man$_7$GlcNAc$_2$, Man$_6$GlcNAc$_2$, Man$_5$GlcNAc$_2$) and polypeptides having complex N-glycan structures as described here above.

The term "predominant" or "predominantly" used with respect to the production of N-glycans refers to a structure which represents the major ion detected by matrix assisted laser desorption ionization time of flight mass spectrometry (MALDI-TOF MS) analysis. Abbreviations used herein are of common usage in the art, see, e.g., abbreviations of sugars, above. Other common abbreviations include "PNGase", which refers to peptide N-glycosidase, "GlcNAc T" or "GnT" which refers to N-acetylglucosaminyltransferase enzymes; "NeuAc" refers to N-acetylneuraminic acid.

As used herein, a "humanized glycoprotein or protein" or a "human-like glycoprotein" refers alternatively to a protein having attached thereto N-glycans having fewer than four mannose residues, and synthetic glycoprotein intermediates (which are also useful and can be manipulated further in vitro or in vivo) having at least five mannose residues. Preferably, glycoproteins produced according to the invention contain at least 30 mole %, preferably at least 40 mole % and more preferably 50, 60, 70, 80, 90, or even 100 mole % of the Man$_5$GlcNAc$_2$ intermediate, at least transiently. This may be achieved, e.g., by engineering a host cell of the invention to express a "better", i.e., a more efficient glycosylation pathway. For example, a mannosidase is selected such that it will have optimal activity under the conditions present at the site in the host cell where proteins are glycosylated and is introduced into the host cell preferably by targeting the enzyme to a host cell organelle where activity is desired.

The term "enzyme", when used herein in connection with altering host cell glycosylation, refers to a molecule having at least one enzymatic activity, and includes full-length enzymes, catalytically active fragments, chimerics, complexes, and the like. A "catalytically active fragment" of an enzyme refers to a polypeptide having a detectable level of functional (enzymatic) activity. Enzyme activity is "substantially intracellular" when less than 10% of the enzyme activity is measurable outside the cell compared to that measurable from lysed cells.

As used herein, the term "secretion pathway" refers to the assembly line of various glycosylation enzymes to which a lipid-linked oligosaccharide precursor and a N-glycan substrate are sequentially exposed, following the molecular flow of a nascent polypeptide chain from the cytoplasm to the endoplasmic reticulum (ER), to compartments of the Golgi apparatus and to its final destination. Enzymes are said to be localized along this pathway. An enzyme X that acts on a lipid-linked glycan or on a N-glycan before enzyme Y is said to be or to act "upstream" to enzyme Y; similarly, enzyme Y is or acts "downstream" from enzyme X.

The term "targeting peptide" as used herein refers to amino acid sequences which mediates the localization (or retention) of an associated sequence to sub-cellular locations, e.g., organelles.

The term "polynucleotide" or "nucleic acid molecule" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation. The term includes single and double stranded forms of DNA. A nucleic acid molecule of this invention may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e. g., methyl phosphonates, phosphotriesters, phosphoramidates, carbamates, etc.), charged linkages (e.g.,phosphorothioates, phosphorodithioates, etc.), pendent moieties (e.g., polypeptides), intercalators (e.g. acridine, psoralen, etc.), chelators, alkylators, and modified linkages (e.g. alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The term "transformed microalgae" refers to a microalgae wherein a nucleotide sequence operably linked to a promoter has been introduced by conventional methods of transformation (e.g., microparticie bombardment, electroporation, glass beads, polyethylene glycol (PEG), silicon carbide whiskers, or uses of viruses or agrobacterium) so as to express said nucleic acid molecule in the nucleus of said microalgae.

An "isolated" or "substantially pure" nucleic acid or polynucleotide (e. g., an RNA, DNA or a mixed polymer) is one which is substantially separated from other cellular components that naturally accompany the native polynucleotide in its natural host cell, e.g., ribosomes, polymerases, and genomic sequences with which it is naturally associated. The term embraces a nucleic acid or polynucleotide that (1) has been removed from its naturally occurring environment, (2) is not associated with all or a portion of a polynucleotide in which the "isolated polynucleotide" is found in nature, (3) is operatively linked to a polynucleotide which it is not linked to in nature, or (4) does not occur in nature. The term "isolated" or "substantially pure" also can be used in reference to recombinant or cloned DNA isolates, chemically synthesized polynucleotide analogs, or polynucleotide analogs that are biologically synthesized by heterologous systems.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence.

The term "percent sequence identity" or "identical" in the context of nucleic acid sequences refers to the residues in the two sequences which are the same when aligned for maximum correspondence. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences.

The term "substantial homology" or "substantial similarity" when referring to a nucleic acid or fragment thereof, indicates that, when optimally aligned with appropriate nucleotide insertions or deletions with another nucleic acid (or its complementary strand), there is nucleotide sequence identity in at least about 50%, more preferably 60% of the nucleotide bases, usually at least about 70%, more usually at least about 80%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

Alternatively, substantial homology or similarity exists when a nucleic acid or fragment thereof hybridizes to another nucleic acid, to a strand of another nucleic acid, or to the complementary strand thereof, under stringent hybridization conditions. "Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization. In general, "stringent hybridization" is performed at about 25° C. below the thermal melting point (Tm) for the specific DNA hybrid under a particular set of conditions. "Stringent washing" is performed at temperatures about 5° C. lower than the Tm for the specific DNA hybrid under a particular set of conditions. The Tm is the temperature at which 50% of the target sequence hybridizes to a perfectly matched probe. For example, "high stringency conditions" can be defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled artisan that hybridization at 65° C. will occur at different rates depending on a number of factors including the length and percent identity of the sequences which are hybridizing.

The term "mutated" when applied to nucleic acid sequences means that nucleotides in a nucleic acid sequence may be inserted, deleted or changed compared to a reference nucleic acid sequence. A single alteration may be made at a locus (a point mutation) or multiple nucleotides may be inserted, deleted or changed at a single locus. In addition, one or more alterations may be made at any number of loci within a nucleic acid sequence. A nucleic acid sequence may be mutated by any method known in the art including but not limited to mutagenesis techniques such as "error-prone PCR" (a process for performing PCR under conditions where the copying fidelity of the DNA polymerase is low, such that a high rate of point mutations is obtained along the entire length of the PCR product.)

The term "vector" as used herein is intended to refer to a nucleic acid molecule capable of transporting another nucleic acid to which it has been linked. One type of vector is a "plasmid", which refers to a circular double stranded DNA loop into which additional DNA segments may be ligated. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Some vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply, "expression vectors").

"Operatively linked" expression control sequences refers to a linkage in which the expression control sequence is contiguous with the gene of interest to control the gene of interest, as well as expression control sequences that act in trans or at a distance to control the gene of interest.

The term "expression control sequence" as used herein refers to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "recombinant host cell" (or simply "host cell"), as used herein, is intended to refer to a cell into which a nucleic acid such as a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

The term "peptide" as used herein refers to a short polypeptide, e.g. one that is typically less than about 50 amino acids long and more typically less than about 30 amino acids long. The term as used herein encompasses analogs and mimetics that mimic structural and thus biological function.

The term "polypeptide" as used herein encompasses both naturally-occurring and non-naturally-occurring proteins, and fragments, mutants, derivatives and analogs thereof. A polypeptide may be monomeric or polymeric. Further, a polypeptide may comprise a number of different domains each of which has one or more distinct activities.

The term "isolated protein" or "isolated polypeptide" is a protein or polypeptide that by virtue of its origin or source of derivation (1) is not associated with naturally associated components that accompany it in its native state, (2) when it exists in a purity not found in nature, where purity can be adjudged with respect to the presence of other cellular material (e. g., is free of other proteins from the same species) (3) is expressed by a cell from a different species, or (4) does not occur in nature (e. g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well-known in the art. As thus defined, "isolated" does not necessarily require that the protein, polypeptide, peptide or oligopeptide so described has been physically removed from its native environment.

The term "polypeptide fragment" as used herein refers to a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

A "modified derivative" refers to polypeptides or fragments thereof that are substantially homologous in primary structural sequence but which include, e.g., in vivo or in vitro chemical and biochemical modifications or which incorporate amino acids that are not found in the native polypeptide. Such modifications include, for example, acetylation, carboxylation, phosphorylation, glycosylation, ubiquitination, labeling, e.g. with radionucleotides, and various enzymatic modifications, as will be readily appreciated by those well skilled in the art. A variety of methods for labeling polypeptides and of substituents or labels useful for such purposes are well-known in the art, and include radioactive isotopes such as 125I, 32P, 35S, and 3H, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods for labeling polypeptides are well-known in the art.

A "polypeptide mutant" or "mutein" refers to a polypeptide whose sequence contains an insertion, duplication, deletion, rearrangement or substitution of one or more amino acids compared to the amino acid sequence of a native or wild-type protein. A mutein may have one or more amino acid point substitutions, in which a single amino acid at a position has been changed to another amino acid, one or more insertions and/or deletions, in which one or more amino acids are inserted or deleted, respectively, in the sequence of the naturally-occurring protein, and/or truncations of the amino acid sequence at either or both the amino or carboxy termini. A mutein may have the same but preferably has a different biological activity compared to the naturally-occurring protein. A mutein has at least 70% overall sequence homology to its wild-type counterpart. Even more preferred are muteins having 80%, 85% or 90% overall sequence homology to the wild-type protein. In an even more preferred embodiment, a mutein exhibits 95% sequence identity, even more preferably 97%, even more preferably 98% and even more preferably 99% overall sequence identity. Sequence homology may be measured by any common sequence analysis algorithm, such as Gap or Bestfit. Preferred amino acid substitutions are those which: (1) reduce susceptibility to proteolysis, (2) reduce susceptibility to oxidation, (3) alter binding affinity for forming protein complexes, (4) alter binding affinity or enzymatic activity, and (5) confer or modify other physicochemical or functional properties of such analogs. As used herein, the twenty conventional amino acids and their abbreviations follow conventional usage.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences). In a preferred embodiment, a homologous protein is one that exhibits 60% sequence homology to the wild type protein, more preferred is 70% sequence homology. Even more preferred are homologous proteins that exhibit 80%, 85% or 90% sequence homology to the wild type protein. In a yet more preferred embodiment, homologous protein exhibits 95%, 97%, 98% or 99% sequence identity. As used herein, homology between two regions of amino acid sequence (especially with respect to predicted structural similarities) is interpreted as implying similarity in function.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art. The following six groups each contain amino acids that are conservative substitutions for one another : 1) Serine (S), Threonine (T); 2) Aspartic Acid (D), Glutamic Acid (E); 3) Asparagine (N), Glutamine (Q); 4) Arginin (R), Lysine (K) ; 5) Isoleucine (I), Leucine (L), Methionine (M), Alanine (A). Valine (V), and 6) Phenylalanine (F), Tyrosine (Y), Tryptophan (W). Sequence homology for polypeptides, which is also referred to as percent sequence identity, is typically measured using sequence analysis software.

The term "fusion protein" refers to a polypeptide comprising a polypeptide or fragment coupled to heterologous amino acid sequences. Fusion proteins are useful because they can be constructed to contain two or more desired functional elements from two or more different proteins. A fusion protein comprises at least 10 contiguous amino acids from a polypeptide of interest, more preferably at least 20 or 30 amino acids, even more preferably at least 40, 50 or 60 amino acids, yet more preferably at least 75, 100 or 125 amino acids. Fusion proteins can be produced recombinantly by constructing a nucleic acid sequence which encodes the polypeptide or a fragment thereof in-frame with a nucleic acid sequence encoding a different protein or peptide and then expressing the fusion protein. Alternatively, a fusion protein can be produced chemically by crosslinking the polypeptide or a fragment thereof to another protein.

The term "region" as used herein refers to a physically contiguous portion of the primary structure of a biomolecule. In the case of proteins, a region is defined by a contiguous portion of the amino acid sequence of that protein.

The term "domain" as used herein refers to a structure of a biomolecule that contributes to a known or suspected function of the biomolecule. Domains may be co-extensive with regions or portions thereof; domains may also include distinct, non-contiguous regions of a biomolecule. Examples of protein domains include, but are not limited to, an Ig domain, an extracellular domain, a transmembrane domain, a catalytic domain and a cytoplasmic domain.

As used herein, the term "molecule" means any compound, including, but not limited to, a small molecule, peptide, protein, sugar, nucleotide, nucleic acid, lipid, etc. . . . and such a compound can be natural or synthetic.

II. The Invention

The invention aims to provide a new system for producing N-glycosylated polypeptides. Glycosylation is dependant on the endogenous machinery present in the host cell chosen for producing glycosylated polypeptides.

The Applicant surprisingly found that microalgae are capable of producing glycosylated polypeptides having a glycosylation pattern suitable for therapeutic purpose in animals in high yield via their endogenous N-glycosylation machinery.

Thus, one aspect of the invention is the production of polypeptides harbouring $Man_5GlcNAc_2$ to $Man_9GlcNAc_2$ in microalgae and another aspect of the invention is the production of complex N-glycans in modified microalgae.

An object of the invention is transformed microalgae comprising a nucleotide sequence operably linked to a promoter that drives expression in said microalgae, wherein said nucleotide sequence encodes a glycosylated polypeptide that is expressed in the transformed microalgae.

Microalgae, as used herein, are aquatic unicellular photosynthetic organisms, comprising:

green algae: Chlorophytes such as *Chlorella marina* (e.g., CCMP2333), *Chlorella sorokiniana* (e.g., UTEX 1663), *Chlorella* sp. (CCMP 2251), *Chlorella pyrenoidosa*, *Chlorella protothecoides*, nanochloropsis such as *Nannochloropsis salina* (e.g., CCAP849/2), and *Nannochloropsis goditana* (e.g., CCAP849/5), Trebouxiophytes, Ulvophytes, Prasinophytes such as *Tetraselmis suecica* (e.g., CCMP904), *Tetraselmis marina* (e.g., CCMP898), *Prasinococcus capsulatus* (e.g., CCMP1192) *Nephroselmis rotunda* (e.g., UTEXLB996) *Ostreococcus tauri*, and Mesostigma;

red algae: Rhodophytina such as *Porphyridium cruentum* (e.g., CCAP1320/3 and CCMP 675) or *Rhodella violacea* (e.g., SAG-115.79), Cyanidiophytes and Glaucophytes;

chromalveolates: Dinofiagellates such as *Heterocapsa triquetra* (e.g., CCMP448), Oxyhrris, Perkinsus, Diatoms such as *Thalassiosira pseudonana* (e.g., CCMP1335), *Phaeodactylum tricornutum* (e.g., CCAP1052/1A, P.t. 1.8.6, and et CCMP632), *Cylindrotheca fusiformis* (e.g., CCMP344), *Skeletonema costatum* (CCMP1332), *Chaeotoceros calcitrans* (e.g., CCMP1315), *Nitzschia punctata* (e.g., CCMP561), *Amphora coffeaeformis* (e.g., CCMP127), *Odontella aurita* (e.g., CCMP 145), and naviculas, Raphidiophytes, Chrysophytes, such as *Pavlova lutheri* (e.g., CCMP1325), Phaeophytes, Bolidophytes, Actinophryids, Thraustrochytrids, Haptophytes such as *Isochrysis galbana* (e.g., CCAP927/14), Eustigmatophytes, and Cryptomonads;

Euglenids such as *Eutreptiella gymnastica* (e.g., CCMP1594).

Preferably, said microalgae is not part of *Ostreococcus* sp., most preferably, said microalgae is not *Ostreococcus tauri* or *Ostreococcus oceanica*.

Preferably, said microalgae is not part of Chlamydomonadales.

The microalgae does not share any beta (1,2)-xylosyl transferase and or alpha (1,3) fucosyl transferase activity before being transformed. In fact, and surprisingly, the inventors have established that microalgae compared to plants, do not add β(1,2)-linked xylose and/or α(1,3)-linked fucose to protein N-glycans which are immunogenic in mammals.

Consequently, it is not necessary compared to plants to inactivate beta (1,2)-xylosyl transferase and/or alpha fucosyl transferase for producing in microalgae therapeutic glycoproteins not comprising β(1,2)-linked xylose and/or α(1,3)-linked fucose.

The skilled person can simply identify the microalgae not sharing any beta (1,2)-xylosyl transferase and/or alpha(1,3) fucosyl transferase activity before being transformed by well known methods, such as methods disclosed hereafter in the examples.

For example, the skilled person can simply identify the microalgae not sharing any beta (1,2)-xylosyl transferase and/or alpha(1,3) fucosyl transferase activity using the antibodies anti-alpha (1,3) fucose (ref: AS07268) and anti-beta (1,2) xylose (ref: AS07267) from AGRISERA.

Advantageously, said microalgae allows the production of said glycosylated polypeptide with a glycosylation pattern suitable for therapeutic purpose in animals without needing the suppression of genes responsibles for the addition of immunogenic epitopes such as in plants, which add β(1,2)-linked xylose and/or α(1,3)-linked fucose to protein N-glycans resulting in glycoproteins that differ in structure from animals and are immunogenic in mammals, or yeasts which express mannosyltransferase genes adding a mannose to the glycan structure and leading to hypermannosylated proteins In fact, the glycosylated polypeptide expressed in the transformed microalgae does not comprise β(1,2)-linked fucose and/or α(1,3)-linked fucose and said microalgae does not share any beta (1,2)-xylosyl transferase and/or alpha fucosyl transferase activity before being transformed.

Also, said microalgae does not share any mannosyltransferase activity leading to hypermannosylated proteins resulting from the addition of mannose to the glycan structure as observed in yeast and in fungi.

In a preferred embodiment of the invention, the microalgae are selected among Diatoms, Euglenids, Haptophytes, Prasinophytes and Chlorophytes.

In a preferred embodiment of the invention, the microalgae are selected among Chlorophytes and Prasinophytes.

In a preferred embodiment of the invention, the microalgae are selected among Diatoms and Haptophytes.

In a preferred embodiment of the invention, the microalgae are selected among Euglenids.

The glycosylated proteins produced in the transformed microalgae may be used therapeutically in animals, especially in mammals and more particularly in humans.

In one embodiment of the invention, the glycosylated polypeptide is selected from the group comprising a polypeptide having a primary amino acid sequence of a human glycosylated polypeptide, a primary amino acid sequence of a non-human mammalian glycosylated polypeptide, a primary amino acid sequence of an antibody or an active fragment thereof, and/or a primary amino acid sequence of a non-mammalian glycosylated polypeptide.

In a preferred embodiment of the invention, the glycosylated polypeptide is an animal polypeptide.

In a preferred embodiment of the invention, the glycosylated polypeptide is a mammalian polypeptide.

In a more preferred embodiment of the invention, the glycosylated polypeptide is a human polypeptide.

Examples of suitable glycosylated proteins include without limitation: erythropoietin, cytokines such as interferons, antibodies, coagulation factors, hormones, beta-glucocerebrosidase, pentraxin-3, anti-TNFs . . .

Examples of promoter that drives expression of a recombinant protein in microalgae include, but are not restricted to, nuclear promoters such as those disclosed in Table 1; chloroplastic promoters such as promoters of rbc1 gene (ribulose biphosphate carboxylase/oxygenase main sub-unit) and atpA gene (λ-ATP synthase sub-unit) from *Chlamydomonas reinhardtii*, or 5'UTR of rrn gene, atpB gene, psbA gene, psbD gene; and plant or animal promoters.

TABLE 1

| Microalgae | promoter | references |
|---|---|---|
| *Chlamydomonas* sp. | rbcS2 | (Sizova et al. 2001) |
| | | (Fuhrmann et al. 1999) |
| | | (Kovar et al. 2002) |
| | | (StevensetPurton 1997) |
| | | (Cerutti 1997) |
| | | (Auchincloss et al. 1999) |
| | cabII-1 | (BlankenshipetKindle 1992) |
| | β2 tubulin | (Davies 1992) |
| | CaMV 35S | (Tang et al. 1995) |
| | Nitrate reductase Nit1 | (Ohresser 1997) |
| | PsaD Photosystem I Complex | (FischeretRochaix 2001) |
| | HSP70 | (Schroda et al. 2002) |
| | Nopalin synthase | (Hall et al. 1993) |
| *Phaeodactylum tricornutum* | FCPA, FCPB | (Apt et al. 1996) |
| | | (Falciatore et al. 1999) |
| | | (Zaslavskaia et al. 2000) |
| | Anhydrase carbonique | (Harada et al. 2005) |
| *Cylindrotheca fusiformis* | Nitrate reductase | (PoulsenetKroger 2005) |
| | Fruα 3 | (Fischer et al. 1999) |
| *Dunaliella salina* | Actin | (Jiang et al. 2005) |
| *Chlorrella ellipsoidea* | CaMV 35S | (Kim et al. 2002) |
| *Amphidinium* sp., *Symbiodinium microadriaticum* | p1\'2\' | (ten LohuisetMiller 1998) |
| *Cyclotella cryptica* | ACC1 | (Dunahay et al. 1995) |
| *Thalassiosira pseudonana* | fcp gene LHCF9 | (Poulsen et al. 2006) |

In a preferred embodiment of the invention, the glycosylated polypeptide expressed in the transformed microalgae comprises a glycosylation pattern suitable for therapeutic purposes, especially an animal glycosylation pattern, preferably a mammalian glycosylation pattern, and more preferably a human-like glycosylation pattern.

In a more preferred embodiment, the glycosylated polypeptide expressed in the transformed microalgae comprises at least one $Man_5GlcNAc_2$ structure. In an embodiment of the invention, the glycosylated polypeptide having at least one $Man_5GlcNAc_2$ structure is further subjected to at least one further glycosylation reaction in vitro, subsequent to its isolation from the transformed microalgae.

This invention also aims to provide transformed microalgae capable of producing complex N-glycans.

Another object of the invention thus relates to transformed microalgae as described, here above, further expressing an N-acetylglucosaminyltransferase I (GnT I) capable of adding an N-acetylglucosamine (GlcNAc) residue to $Man_5GlcNAc_2$ to produce a $GlcNAcMan_5GlcNAc_2$. N-acetylglucosaminyltransferases I (GnT I) are well known from one of skilled in the art, and are also known as mannoside acetylglucosaminyltransferase 1 (MGAT1). As an example of GnTI, one can cite the GnTI from *Mus musculus* (SEQ ID NO: 18, Accession number NP_034924) or from *Homo sapiens* (SEQ ID NO: 19, Accession number NP_002397). Preferably, said N-acetylglucosaminyltransferase I (GnT I) corresponds to SEQ ID NO: 19 (Accession number NP_002397).

Another object of the invention also relates to transformed microalgae as described here above; further expressing an N-acetylglucosaminyltransferase (GnT I, GnT II, GnT III, GnT IV, GnT V, GnT VI), a mannosidase II and a fucosyltransferase, galactosyltransferase (GalT) or sialyltransferases (ST), to produce complex N-glycans.

GnT I, GnT II, GnT III, GnT IV, GnT V, GnT VI, mannosidase II, fucosyltransferase, galactosyltransferase (GalT) and sialyltransferases (ST) are well known from one of skilled in the art.

Examples of GnT II, also known as mannosyl (alpha-1,6-)-glycoprotein beta-1,2-N-acetylglucosaminyltransferase (MGAT2), include GnT II from *Mus musculus* (SEQ ID NO: 20, Accession number NP_666147) or from *Homo sapiens* (SEQ ID NO: 21, Accession number NP_002399). Preferably, said N-acetylglucosaminyltransferase II (GnT II) corresponds to SEQ ID NO: 21 (Accession number NP_002399)

Examples of GnT III, also known as mannosyl (beta-1,4-)-glycoprotein beta-1,4-N-acetylglucosaminyltransferase (MGAT3), include GnT III from *Mus musculus* (SEQ ID NO: 22, Accession number NP_034925) or from *Homo sapiens* (SEQ ID NO: 23, Accession number NP_002400). Preferably, said N-acetylglucosaminyltransferase III (GnT III) corresponds to SEQ ID NO: 22 (Accession number NP_002400).

Examples of GnT IV, also known as mannosyl (alpha-1,3-)-glycoprotein beta-1,4-N-acetylglucosaminyltransferase (MGAT4), include GnT IV isozyme A from *Mus musculus* (SEQ ID NO: 24, Accession number NP_776295), isozyme B from *Mus musculus* (SEQ ID NO: 25, Accession number NP_666038), isozyme C from *Mus musculus* (SEQ ID NO: 26, Accession number NP_080519), GnT IV isozyme A from *Homo sapiens* (SEQ ID NO: 27, Accession number NP_036346), GnT IV isozyme B from *Homo sapiens* (isoform 1, SEQ ID NO: 28, Accession number NP_055090 or isoform 2, SEQ ID NO: 29, Accession number NP_463459) or GnT IV isozyme C from *Homo sapiens* (SEQ ID NO: 30, Accession number NP_037376).

Examples of GnT V, include GnT V from *Mus musculus* (SEQ ID NO: 31, Accession number NP_660110), GnT V isozyme B from *Mus musculus* (SEQ ID NO: 32, Accession number NP_766536), GnT V from *Homo sapiens* (SEQ ID NO: 33, Accession number NP_002401), GnT V isozyme B from *Homo sapiens* (isoform 1, SEQ ID NO: 34, Accession number NP_653278 or isoform 2, SEQ ID NO: 35, Accession number NP_945193).

Example of GnT VI include GnT VI from *Gallus gallus* (SEQ ID NO: 36, Accession number NP_990012).

Examples of mannosidase II (MAN II), also known as mannosidase 2, alpha 1 (MAN2A1), includes MAN II from *Mus musculus* (SEQ ID NO: 37, Accession number NP_032575) or from *Homo sapiens* (SEQ ID NO: 38, Accession number NP_002363). Preferably, said mannosidase II (MAN corresponds to SEQ ID NO: 38 (Accession number NP_002363).

Fucosyltransferases are well known from the skilled person and include, as an example alpha (1,6) fucosyltransferase (fucosyltransferase 8 (FUT8)), like FUT8 from *Mus musculus* (SEQ ID NO: 39, Accession number NP_058589) or FUT8 from *Homo sapiens* (SEQ ID NO: 40, Accession number Q9BYC5). Preferably, said fucosyl transferase corresponds to SEQ ID NO: 40 (Accession number Q9BYC5).

Galactosyltransferase are well known from the skilled person and include, as an example, one beta(1,4)galactosyltransferase (B4GALT1), like B4GALT1 from *Homo sapiens* (SEQ ID NO:66, Accession number NP_001488), or B4GALT1 from *Mus musculus* (SEQ ID NO:67, Accession number CAM14782). Preferably, said galactosyltransferase corresponds to SEQ ID NO:66 (Accession number NP_001488).

Sialyltransferase are well known from the skilled person and include, as an example Alpha 2, 6 Sialyltransferase (ST6 beta-galactosamide alpha-2,6-sialyltranferase 1 (ST6GAL 1) or beta galactoside alpha 2,6 sialyltransferase 2 (ST6GAL2)), like ST6GAL2 from *Mus musculus* (SEQ ID NO: 41, Accession number NP_766417) or ST6GAL1 from *Homo sapiens* (isoform a, SEQ ID NO: 42, Accession number NP_775323 or isoform b, SEQ ID NO: 43, Accession number NP_775324), or Alpha 2, 3 Sialyltransferase (ST3 beta-galactoside alpha-2,3-sialyltransferase 6 (ST3GAL6), ST3 beta-galactoside alpha-2,3-sialyltransferase 1 (ST3GAL1), ST3 beta-galactoside alpha-2,3-sialyltransferase 2 (ST3GAL2), ST3 beta-galactoside alpha-2,3-sialyltransferase 3 (ST3GAL3), like ST3GAL1 from *Mus musculus* (SEQ ID NO: 44, Accession number NP_033203) or from *Homo sapiens* (SEQ ID NO: 45, Accession number NP_003024), ST3GAL2 from *Homo sapiens* (SEQ ID NO: 46 Accession number NP_008858), ST3GAL3 from *Homo sapiens* (isoform a, SEQ ID NO: 47, Accession number NP_777623, isoform b, SEQ ID NO: 48, Accession number NP_777624, isoform c, SEQ ID NO: 49, Accession number NP_777625, isoform f, SEQ ID NO: 50, Accession number NP_777628, isoform j, SEQ ID NO: 51, Accession number NP_006270, isoform d, SEQ ID NO: 52, Accession number NP_777626, isoform e, SEQ ID NO: 53, Accession number NP_777627, isoform i, SEQ ID NO: 54, Accession number NP_777631, isoform g, SEQ ID NO: 55, Accession number NP_777629, isoform h, SEQ ID NO: 56, Accession number NP_777630), or ST3GAL6 from *Homo sapiens* (SEQ ID NO: 57, Accession number NP_006091).

Another object of the invention relates to transformed microalgae as described here above, further expressing GnT I enzyme, an α-1,3/α-1,6-mannosidase activity, such as Mannosidase II, and GnT III enzyme capable of transferring β1,4-GlcNAc onto substrates that are capable of accepting the bisecting GlcNAc, to produce a bisected GlcNAc$_2$Man$_3$GlcNAc$_2$.

Another object of the invention relates to transformed microalgae as described here above, further expressing GnT I enzyme, an α-1,3/α-1,6-mannosidase activity, such as Mannosidase II, and GnT II enzyme capable of transferring β1,2-GlcNAc onto substrates, to produce GlcNAc$_2$Man$_3$GlcNAc$_2$.

Another object of the invention relates to transformed microalgae as described here above, further expressing GnT I enzyme, an α-1,3/α-1,6-mannosidase activity, such as Mannosidase II, and GnT III enyme capable of transferring β1,4-GlcNAc onto substrates that are capable of accepting the bisecting GlcNAc, to produce a bisected GlcNAc$_2$Man$_3$GlcNAc$_2$.

Another object of the invention relates to transformed microalgae as described here above, further expressing GnT I enzyme, an α-1,3/α-1,6-mannosidase activity, such as Mannosidase II, GnT II and GnT III enzymes, to produce a bisected GlcNAc$_3$Man$_3$GlcNAc$_2$.

Another object of the invention relates to transformed microalgae as described here above, further expressing GnT I enzyme, an α-1,3/α-1,6-mannosidase activity, such as Mannosidase II, and one or more glycosylation enzymes among GnT IV, GnT V and GnT VI, to produce tri-antennary or tetra-antennary N-linked glycans.

Another object of the invention relates to transformed microalgae as described here above, further expressing GnT I enzyme, an α-1,3/α-1,6-mannosidase activity, such as Mannosidase II, GnT II enyme and one or more glycosyltransferases selected among fucosyltransferase, galactosyltransferase or sialyltransferases.

With DNA sequence information, one skilled in the art can clone DNA molecules encoding GnT activities. Using standard techniques well-known in the art, nucleic acid molecules encoding GnT I, II, III, IV, V, or VI, Mannosidase II, or a glycosyltransferase such as fucosyltransferase, galactosyltransferase or sialyltransferase (or encoding catalytically active fragments thereof) may be inserted into appropriate expression vectors under the transcriptional control of promoters and other expression control sequences capable of driving transcription in selected microalgae, such that one or more of these enzymes may be actively expressed in the microalgae.

Preferably, the enzymes are of human origin, although other animal, mammalian, plant or microalgae enzymes are also useful.

In one embodiment of the invention, genes are truncated to give fragments encoding the catalytic domains of the enzymes. By removing endogenous targeting sequences, the enzymes may then be redirected and expressed in other cellular localisation. The choice of such catalytic domains may be guided by the knowledge of the particular environment in which the catalytic domain is subsequently to be active. For example, if a particular glycosylation enzyme is to be active in the late Golgi, and all known enzymes of the host organism in the late Golgi have a certain pH optimum, then a catalytic domain is chosen which exhibits adequate activity at that pH. DNA encoding catalytically active fragments of the enzymes are then ligated to DNA encoding signal peptides to localize the enzymes within the ER, Golgi, or trans-Golgi network. These signal sequences may be selected from the host organism as well as from other related or unrelated organisms. Membrane-bound proteins of the ER or Golgi typically may include, for example, N-terminal sequences encoding a cytosolic tail (ct), a transmembrane domain (tmd), and a stem region (sr). The ct, tmd, and sr sequences are sufficient individually or in combination to anchor proteins to the inner (lumenal) membrane of the organelle. Another source of signal sequences include retrieval signal peptides, e.g. the tetrapeptides HDEL, KDEL, DDEL or either equivalent retrieval signal, which are typically found at the C-terminus of proteins that induced a retrograde transport into the ER or Golgi.

In an embodiment of the invention, said nucleotide sequence operably linked to a promoter that drives expression of GnT I, II, III, IV, V, or VI, Mannosidase II, or a glycosyltransferase such as fucosyltransferase, galactosyltransferase or sialyltransferase in the said microalgae, comprises said enzyme catalytic domain having optimal activity in said ER and Golgi at a pH between 5.1 and 8, fused to a cellular targeting signal not normally associated with the catalytic domain.

For a glycosyltransferase to function satisfactorily in the Golgi apparatus, it is necessary for the enzyme to be provided with sufficient concentrations of an appropriate nucleotide sugar, which is the high-energy donor of the sugar moiety added to a nascent glycoprotein. In humans, the full range of nucleotide sugar precursors are generally synthesized in the cytosol and transported into the Golgi apparatus, where they are attached to the core oligosaccharide by glycosyltransferases. The Applicant observed in microalgae a sufficient concentration of GlcNAc, mannose, fucose and galactose but not of sialic acid.

Therefore, for a sialyltransferase to function satisfactorily in the Golgi apparatus, it is necessary to express in the microalgae one or more enzymes needed for sialic acid synthesis, its activation and its transport within the Golgi apparatus among UDP GlcNAc 2-epimerase, GlcNAc 2-epimerase, GlcNAc-6P 2-epimerase, NeuAc synthase. NeuAc-9P synthase, CMP-NeuAc synthase and CMP-sialic acid transporter (see for example works done in plants: Misaki R et al. Biochem Biophys Res Commun. 2006 Jan. 27; 339(4):1184-9; Paccalet T et al. Plant Biotechnol J. 2007 January; 5(1): 16-25).

UDP GlcNAc 2-epimerase, which is also known as glucosamine (UDP-N-acetyl)-2-epimerase/N-acetylmannosamine kinase (GNE), is well known from the skilled person and include, as an example GNE from *Mus musculus* (SEQ ID NO: 58, Accession number NP_056643) or GNE from *Homo sapiens* (SEQ ID NO: 59, Accession number NP_005467). Preferably, said GNE corresponds to SEQ ID NO: 59 (Accession number NP_005467).

GlcNAc 2-epimerase is well known from the skilled person and includes, as an example, the renin binding protein (RENBP) from *Homo sapiens* (SEQ ID NO: 60, Accession number NPJ)02901).

NeuAc-9P synthase, also called N-acetylneuraminic acid synthase (NANS), is well known from the skilled person and include, as an example, NANS from *Homo sapiens* (SEQ ID NO: 61, Accession number NP_061819).

CMP-NeuAc synthase, which is also known as cytidine monophospho-N-acetylneuraminic acid synthetase (CMAS), is well known from the skilled person and include, as an example CMAS from *Mus musculus* (SEQ ID NO: 62, Accession number NP_034038) or from *Homo sapiens* (SEQ ID NO: 63, Accession number NP_061156). Preferably, said CMAS corresponds to SEQ ID NO: 63 (Accession number NP_061156).

CMP-sialic acid transporters are also well known from the skilled person and include, as an example, solute carrier family 35 (CMP-sialic acid transporter), member A1 (SLC35A1) from *Mus musculus* (SEQ ID NO: 64, Accession number NP_036025) or from *Homo sapiens* (SEQ ID NO: 65, Accession number NP_006407). Preferably, said CMP-sialic acid transporter corresponds to SLC35A1 from *Homo sapiens* (SEQ ID NO: 65, Accession number NP_006407).

The added transporter protein conveys a nucleotide sugar from the cytosol into the Golgi apparatus, where the nucleotide sugar may be reacted by the glycosyltransferase, e.g. to elongate an N-glycan. The reaction liberates a nucleoside diphosphate or monophosphate, e.g. UDP, GDP, or CMP. As accumulation of a nucleoside diphosphate inhibits the further activity of a glycosyltransferase, it is frequently also desirable to provide an expressed copy of a gene encoding a nucleotide diphosphatase. The diphosphatase (specific for UDP or GDP as appropriate) hydrolyzes the diphosphonucleoside to yield a nucleoside monophosphate and inorganic phosphate. The nucleoside monophosphate does not inhibit the glycosyltransferase and in any case is exported from the Golgi by an endogenous cellular system.

One object of the invention is transformed microalgae, expressing an N-acetylglucosaminyltransferase I (GnT I) capable of adding an N-acetylglucosamine (GlcNAc) residue to $Man_5GlcNAc_2$ to produce a $GlcNAcMan_5GlcNAc_2$. Another object of the invention is transformed microalgae, expressing an N-acetylglucosaminyltransferase (GnT I, GnT II, GnT III, GnT IV, GnT V, GnT VT), a mannosidase II and a fucosyltransferase, galactosyltransferase (GalT) or sialyltransferases (ST), to produce complex N-glycans.

Thus, one object of the invention is transformed mivroalgae, expressing GnT I enzyme and an $\alpha$-1,3/$\alpha$-1,6-mannosidase activity, such as Mannosidase II capable of trimming $GlcNAcMan_5GlcNAc_2$ to produce $GlcNAcMan_3GlcNAc_2$.

Another object of the invention is transformed microalgae, expressing GnT I enzyme, an $\alpha$-1,3/$\alpha$-1,6-mannosidase activity, such as Mannosidase II, and GnT II enzyme capable of transferring $\beta$1,2-GlcNAc onto substrates, to produce $GlcNAc_2Man_3GlcNAc_2$.

Another object of the invention is transformed microalgae, expressing GnT I enzyme, an $\alpha$-1,3/$\alpha$-1,6-mannosidase activity, such as Mannosidase II, and GnT III enzyme capable of transferring $\beta$1,4-GlcNAc onto substrates that are capable of accepting the bisecting GlcNAc to produce a bisected $GlcNAc_2Man_3GlcNAc_2$.

Another object of the invention is transformed microalgae, expressing GnT I enzyme, an $\alpha$-1,3/$\alpha$-1,6-mannosidase activity, such as Mannosidase II, GnT II and GnT III enzymes, to produce a bisected $GlcNAc_3Man_3GlcNAc_2$.

Another object of the invention is transformed microalgae, further expressing GnT I enzyme, an $\alpha$-1,3/$\alpha$-1,6-mannosidase activity, such as Mannosidase II, and one or more glycosylation enzymes among GnT IV, GnT V and GnT VI, to produce tri-antennary or tetra-antennary glycoprotein.

Another object of the invention is transformed microalgae, expressing GnT I enzyme, an $\alpha$-1,3/$\alpha$-1,6-mannosidase activity, such as Mannosidase II, GnT II enzyme and one or more glycosyltransferases selected among fucosyltransferase, galactosyltransferase or sialyltransferases.

Another object of the invention is transformed microalgae, expressing GnT I enzyme, an $\alpha$-1,3/$\alpha$-1,6-mannosidase activity, such as Mannosidase II, GnT II enzyme and one or more glycosyltransferases selected among fucosyltransferase, galactosyltransferase or sialyltransferases, provided that it further expresses one or more enzymes needed for sialic acid synthesis, its activation and its transport within the Golgi apparatus among UDP-GlcNAc 2-epimerase, GlcNAc 2-epimerase, GlcNAc-6P 2-epimerase, NeuAc synthase, NeuAc-9P synthase, CMP-NeuAc synthase and CMP-sialic acid transporter, when the glycosyltransferase selected is a sialyltransferase.

In an embodiment of the invention, said nucleotide sequence operably linked to a promoter that drives expression of GnT I, II, III, IV, V, or VI, Mannosidase II, or a glycosyltransferase such as fucosyltransferase, galactosyltransferase or sialyltransferase in the said microalgae cells, comprises said enzyme catalytic domain having optimal activity in said ER and Golgi at a pH between 5.1 and 8, fused to a cellular targeting signal not normally associated with the catalytic domain.

In another embodiment of the invention, said microalgae cell is selected among green algae, red algae, chromalveolates, and euglenids.

One object of the invention is a method for producing at least one glycosylated polypeptide comprising the steps of:
  (i) culturing a transformed microalgae as disclosed previously so as to obtain the expression of said at least one glycosylated polypeptide; and
  (ii) purifying said at least one glycosylated polypeptide.

Advantageously, the method of the invention further comprises the step of transforming a microalgae previous the step (i) so as to obtain a microalgae as defined previously.

Advantageously, the at least one glycosylated polypeptide presents a glycosylation pattern suitable for therapeutic purpose in animals and is produced by said transformed microalgae without needing in said transformed microalgae the suppression of genes responsible for the addition of immunogenic epitopes such as in plants, which add β(1,2)-linked xylose and/or α(1,3)-linked fucose to protein N-glycans resulting in glycoproteins that differ in structure from animals and are immunogenic in mammals, or yeasts which express mannosyltransferase genes adding a mannose to the glycan structure and leading to hypermannosylated proteins.

Thus, said at least one glycosylated polypeptide does not comprise β(1,2)-linked fucose and/or α(1,3)-linked fucose and said microalgae does not share any beta (1,2)-xylosyl transferase and/or alpha fucosyl transferase activity before being transformed.

Moreover, said microalgae does not share any mannosyltransferase activity leading to hypermannosylated proteins resulting from the addition of mannose to the glycan structure as observed in yeast and in fungi.

In a preferred embodiment, said transformed microalgae express at least one enzyme selected among GnT I, II, III, IV, V, or VI, Mannosidase II, or a glycosyltransferase such as fucosyltransferase, galactosyltransferase or sialyltransferase, with a nucleotide sequence operably linked to a promoter that drives expression in said microalgae, wherein said nucleotide sequence encodes a glycosylated polypeptide that is expressed in the transformed microalgae.

In a preferred embodiment, said glycosylated polypeptide produced by said method comprises a glycosylation pattern suitable for therapeutic purposes, especially an animal glycosylation pattern, preferably a mammalian glycosylation pattern, and more preferably a human-like glycosylation pattern.

For purifying a glycosylated polypeptide having a glycosylation pattern suitable for therapeurtic purposes, the method of the invention comprises a step of determining the glycosylation pattern of said at least one glycosylated polypeptide.

This glycosylation pattern can be determined by method well known from the skilled person.

As an example, preliminary informations about N-glycosylation of the recombinant glycoprotein can be obtained by affino- and immunoblotting analysis using specific probes such as lectins (CON A; ECA; SNA; MAA . . . ) and specific N-glycans antibodies (anti-β1,2-xylose; anti-α-1,3-fucose; anti-Neu5Gc, anti-Lewis . . . ). This is made according to FITCHETTE et al., (Plant proteomics and glycosylation, Methods Mol. Biol., vol.355, p: 317-342, 2007) and could be completed by deglycosylation assays.

To investigate the detailed N-glycan profile of recombinant protein, N-linked oligosaccharides is then released from the protein in a non specific manner using enzymatic digestion or chemical treatment (FITCHETTE et al, above mentioned, 2007; SEVENO et al., Plant N-glycan profiling of minute amounts of material, Anal. Biochem., vol. 379 (1), p: 66-72, 2008). The resulting mixture of reducing oligosaccharides can be profiled by HPLC and/or mass spectrometry approaches (ESI-MS-MS and MALDI-TOF essentially, BARDOR et al., Analytical strategies to investigate plant N-glycan profiles in the context of plant-made pharmaceuticals, Curr Opin Struct Biol., vol.16(5), p: 576-583, 2006, SEVENO et al, above mentioned, 2008). These strategies, coupled to exoglycosidase digestion, enable N-glycan identification and quantification (Seveno et al, 2008).

Another alternative to study N-glycosylation profile of recombinant protein is to work directly on its glycopeptides after protease digestion of the protein, purification and mass spectrometry analysis of the glycopeptides as discloed in BARDOR et al. (Monoclonal C5-1 antibody produced in transgenic alfalfa plants exhibits a N-glycosylation that is homogenous and suitable for glyco-engineering into human-compatible structures, Plant Biotechnol J., vol.1(6), p: 451-462, 2003).

Still for purifying a glycosylated polypeptide having a glycosylation pattern suitable for therapeutic purposes, the method of the invention comprises the step of selecting the at least one glycosylated polypeptide sharing a glycosylation pattern suitable for therapeutic purposes, such as a glycosylation pattern does not comprising β(1,2)-linked fucose and/or α(1,3)-linked fucose. More preferably, said at least one glycosylated polypeptide comprises at least one $Man_5GlcNAc_2$ structure.

In another preferred embodiment, said microalgae used in said method which is as described previously, is selected among green algae, red algae, chromalveolates, and euglenids, preferably among Diatoms, Euglenids, Haptophytes, Prasinophytes and Chlorophytes.

In a preferred embodiment of the invention, the glycosylated polypeptide produced by said method is selected from the group comprising a polypeptide having a primary amino acid sequence of a human glycosylated polypeptide, a primary amino acid sequence of a non-human mammalian glycosylated polypeptide, a primary amino acid sequence of an antibody or an active fragment thereof, and/or a primary amino acid sequence of a non-mammalian glycosylated polypeptide.

In a more preferred embodiment, examples of said glycosylated polypeptide expressed in the transformed microalgae include, but are not limited to, erythropoietin, cytokines such as interferons, antibodies, coagulation factors, hormones, beta-glucocerebrosidase, pentraxin-3, anti-TNFs . . .

In another embodiment of the invention, said method comprises the step of isolating the recombinant glycosylated polypeptide subsequent to passage of said recombinant glycosylated polypeptide through the ER and Golgi apparatus of the transformed microalgae.

One object of the invention is a method for producing transformed microalgae, comprising transforming said microalgae with a nucleotide sequence operably linked to a promoter that drives expression in said microalgae, wherein said nucleotide sequence encodes an N-acetylglucosaminyl-transferase I enzyme that is expressed in the transformed microalgae.

In an embodiment of the invention, the method further comprises transforming said microalgae with nucleotide sequences operably linked to promoters that drive expression in said microalgae, wherein said nucleotide sequences encode an N-acetylglucosaminyltransferase I enzyme and a mannosidase II enzyme that is expressed in the transformed microalgae.

In another embodiment of the invention, the method further comprises transforming said microalgae with nucleotide sequences operably linked to promoters that drive expression in said microalgae, wherein said nucleotide sequences encode an N-acetylglucosaminyltransferase I enzyme, a mannosidase II enzyme and an N-acetylglucosaminyltransferase II enzyme that is expressed in the transformed microalgae.

In another embodiment of the invention, the method further comprises transforming said microalgae with nucleotide sequences operably linked to promoters that drive expression in said microalgae, wherein said nucleotide sequences encode an N-acetylglucosaminyltransferase I enzyme, a mannosidase II and at least one enzyme selected among N-acetylglucosaminyltransferase II, IV, V and VI, that is expressed in the transformed microalgae.

In another embodiment of the invention, the method further comprises transforming said microalgae with nucleotide sequences operably linked to promoters that drive expression in said microalgae, wherein said nucleotide sequences encode an N-acetylglucosaminyltransferase I enzyme, a mannosidase II enzyme, at least one enzyme selected among N-acetylglucosaminyltransferase II, IV, V and VI that is expressed in the microalgae, and at least one glycosyltransferase enzyme selected among galactosyltransferase, fucosyltransferase and sialyltransferases, that is expressed in the transformed microalgae.

When sialyltransferases are expressed in the transformed microalgae, said microalgae are also transformed with nucleotide sequences encoding one or more enzymes needed for sialic acid synthesis, its activation and its transport within the Golgi apparatus among UDP GlcNAc 2-epimerase, GlcNAc 2-epimerase. GlcNAc-6P 2-epimerase, NeuAc synthase, NeuAc-9P synthase, CMP-NeuAc synthase and CMP-sialic acid transporter.

In a preferred embodiment of the invention, said nucleotide sequence operably linked to a promoter that drives expression of N-acetylglucosaminyltransferases, mannosidase II or glycosyltransferases in said microalgae, comprises said enzyme catalytic domain having optimal activity in said ER and Golgi at a pH between 5.1 and 8, fused to a cellular targeting signal not normally associated with the catalytic domain.

In one embodiment of the invention, prior to transformation of microalgae, said nucleotide sequences may be subjected to one or more rounds of gene shuffling, error prone PCR, or in vitro mutagenesis.

Transformation of microalgae can be carried out by conventional methods such as microparticles bombardment, electroporation, glass beads, polyethylene glycol (PEG), silicon carbide whiskers, or use of viruses or agrobacterium.

In an embodiment of the invention, nucleotide sequences may be introduced into microalgae via a plasmid, virus sequences, double or simple strand DNA, circular or linear DNA.

In another embodiment of the invention, it is generally desirable to include into each nucleotide sequences or vectors at least one selectable marker to allow selection of microalgae that have been stably transformed. Examples of such markers are antibiotic resistant genes such as sh ble gene enabling resistance to zeocin, nat or sat-1 genes enabling resistance to nourseothricin, bar gene enabling resistance to glufosinate.

After transformation of microalgae, transformants displaying proteins exhibiting the desired glycosylation phenotype are selected. Selection can be carried out by one or more conventional methods comprising: mass spectroscopy such as MALDI-TOF-MS, ESI-MS chromatography, characterization of cells using a fluorescence activated cell sorter, spectrophotometer, fluorimeter, or scintillation counter; exposing cells to a lectin or antibody having a specific affinity for a desired oligosaccharide moiety; exposing cells to a cytotoxic or radioactive molecule selected from the group consisting of sugars, antibodies and lectins.

An object of the invention is the use of a transformed microalgae as disclosed previously for producing at least one glycosylated polypeptide.

Said microlagae and at least one glycosylated polypeptide are as described previously.

Advantageously, said microalgae allows the production of said glycosylated polypeptide with a glycosylation pattern suitable for therapeutic purpose in animals without needing the suppression, in said microalgae, of genes responsible for the addition of immunogenic epitopes such as in plants, which add β(1,2)-linked xylose and/or α(1,3)-linked fucose to protein N-glycans resulting in glycoproteins that differ in structure from animals and are immunogenic in mammals, or yeasts which express mannosyltransferase genes adding a mannose to the glycan structure and leading to hypermannosylated proteins.

In fact, said at least one glycosylated polypeptide does not comprise β(1,2)-linked fucose and/or α(1,3)-linked fucose and said microalgae does not share any beta (1,2)-xylosyl transferase and/or alpha (1,3) fucosyl transferase activity before being transformed.

Therefore, said microalgae does not share any mannosyltransferase activity leading to hypermannosylated proteins resulting from the addition of mannose to the glycan structure as observed in yeast and in fungi.

Still advantageously, said at least one glycosylated polypeptide comprises at least one $Man_5GlcNAc_2$ structure.

An object of the invention is the glycosylated polypeptides produced by the method as described here above.

Another object of the invention is a pharmaceutical composition comprising at least one glycosylated polypeptide produced by the method as described here above.

Another object of the invention is a veterinary composition comprising the glycosylated polypeptide produced by the method of the invention.

EXAMPLES

In the following description, all experiments for which no detailed protocol is given are performed according to standard protocol.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials and Methods
In Silico Genome Analysis

Identification of genes in the *Phaeodactylum tricornutum* genome was carried out by BLAST analysis with *Homo sapiens, Mus musculus, Arabidopsis thaliana, Drosophila melanogaster, Saccharomyces cerevisiae, Physcomitrella patens, Medicago trancatula, Zea mays* and *Medicago sativa* specific genes. The searches for signal peptides and cell localisation/targeting of mature putative proteins were done using CBS Prediction Servers (Center for Biological Sequence Analysis, Technical University of Denmark) SignalP and TargetP. Presence of predicted transmembrane domain as well as search for specific pfam domains were done respectively by CBS server TMHMM and Simple Modular Architecture Research Tool.

Standard Culture Conditions of *Phaeodactylum tricornutum* and *Tetraselmis suecica*

Strains used in this work were *Phaeodactylum tricornutum* CCAP 1052/1A, *Phaeodactylum tricornutum* clone P.t.1.8.6 and Prasinophyte *Tetraselmis suecica* CCMP 904.

Microalgae were grown at 20° C. under continuous illumination (280-350 µmol photons $m^2s^{-1}$), in natural coastal seawater (origin St. Malo, France) sterilized by 0.22 µm filtration. This seawater is enriched with nutritive Conway media (Walne, 1966) with addition for the diatoms of silica (40 g/L of sodium metasilicate; 1 ml/L). For large volume (from 2 liters to 300 liters) cultures were aerated with a 2% $CO_2$/air mixture to maintain the pH in a range of 7.5-8.1.

For genetic transformation, microalgae were spread on gelose containing 1% of agar. After concentration by centrifugation, the microalgae were spread on petri dishes sealed and incubated at 20° C. under constant illumination. Concentration of cultures was estimated on Mallassez counting cells after fixation of the microalgae with a Lugol's solution.

Standard Culture Conditions of *Chlorella*

Strain used in this work was *Chlorella sorokiniana*.

Microalgae were grown at 28° C. under continuous illumination (280-350 µmol photons $m^2s^{-1}$), in Kuhl medium (Kuhl and Lorenzen 1964). For large volume (from 2 liters to 300 liters) cultures were aerated with a 2% $CO_2$/air mixture to maintain the pH in a range of 7.5-8.1.

For genetic transformation, microalgae were spread on gelose containing 1.0% of agar. After concentration by centrifugation, the microalgae were spread on petri dishes sealed and incubated at 28° C. under constant illumination. Concentration of cultures was estimated on Mallassez counting cells after fixation of the microalgae with a Lugol's solution.

Extraction of Proteins from *Phaeodactylum tricornutum* for N-glycosylation Analysis The concentrated culture ($20 \times 10^6$ cells/L) was first centrifuged at 5,000 g for 20 min at 4° C. The pellet was then lyophilised. Two g of lyophilised microalgae were ground in a mortar in the presence of sand using a 750 mM Tris-HCl pH 8 buffer containing 15% (w/v) of sucrose, 2% (v/v) of β-mercaptoethanol and 1 mM phenylmethylsulfonylfluoride (PMSF) and then centrifuged for 30 minutes at 11,500 g, at 4° C. Proteins from the supernatant were then precipitated with 90% ammonium sulfate during 2 hours at room temperature (RT) under stirring and centrifuged for 30 minutes at 11,500 g. The pellet was solubilized in water and then, dialysed against water, overnight at 4° C. Finally, the total protein extract was ultra-centrifuged at 30,000 g for 1 hour at 4° C. and resuspended in the smallest volume of water, prior to protein quantification and further analysis.

Protein Quantification

Protein quantification was performed on the total protein extracts from *Phaeodactylum tricornutum* using the BCA protein assay kit from Pierce according to the manufacturer's instructions.

Immuno- and Affinoblotting Analysis

Fifty µg of total proteins extracted from microalgae were separated by SDS-PAGE using a 12% polyacrylamide gel. The separated proteins were transferred onto nitrocellulose membrane and stained with Ponceau Red in order to control transfer efficiency. The nitrocellulose membrane was blocked overnight at RT with Tris-buffered saline (TBS) containing 0.1% Tween 20 (TBS-T) for affinodetection and overnight in gelatine 3% dissolved in TBS for immunodetection. Immunodetection was then performed using home-made specific core-β1,2-xylose and core-α1,3-fucose antibodies (1:3000 in TBS containing 1% of gelatin, 2 h, RT After washing with TBS-T (6 times, 5 minutes), binding of antibodies was detected using a secondary horseradish peroxidase-conjugated goat anti-rabbit IgG antibody diluted at 1:3,000 in TBS containing 1% gelatin for 1.5 h at RT (Bio-Rad). Final development of the blots was performed by using 4-chloro 1-naphtol as previously described (Fitchette et al., 2007). Affinodetection using concanavalin A was performed by incubation with the lectin at 25 µg/mL, 2 h, RT in TBS-T, complemented with 1 mM $CaCl_2$ and 1 mM $MgCl_2$. After washing with TBS-T complemented with $CaCl_2$ and $MgCl_2$ (6 times, 5 minutes), binding of this lectin was detected using a horseradish peroxidase diluted at 50 µg/mL, 1 h at RT in TBS-T complemented with 1 mM $CaCl_2$ and 1 mM $MgCl_2$. After washing with the same TBS-T and then, TBS, final development of the blots was performed by using 4-chloro-1-naphtol as previously described (Fitchette et al., 2007). Affinodetection with biotinylated phytohemagglutinin E and L (PHA-E and L), biotinylated *Erythrina Crista Galli* Agglutinin (ECA) and biotinylated peanut agglutinin (PNA) were done by incubation of these lectins at 20 µg/mL in respectively TBS-T for PHA-E and L and TBS-T complemented with 0.1 mM of $CaCl_2$ and 0.5 mM $MnCl_2$. After washing with adequate TBS-T, binding of these lectins was detected using streptavidin coupled with horseradish peroxidase diluted at 1/3,000, 45 minutes at RT in adequate TBS-T. Final development of the blots was performed as for concanavalin A affinodetection. Oxidation of the glycan moiety of glycoproteins was carried out on blot using sodium periodate according to Fitchette-Lainé et al., 1998.

Deglycosylation by PNGase F or Endo H

Deglycosylation assay was done on a total protein extract using peptide N-glycosidase F isolated from *Flavobacterium meningosepticum* (PNGase F) or using Endoglycosidase H (Endo H).

1 mg of total proteins was first dissolved into 2 ml of 0.1 M Tris-HCl buffer, pH 7.5 containing 0.1% SDS. The sample was heated 5 minutes at 100° C. for protein denaturation. After cooling down, 2 mL of a 0.1 M Tris-HCl buffer, pH 7.5, containing 0.5% Nonidet P-40 were added to the sample as well as 10 units of PNGase F. The digestion was incubated during 24 h at 37° C. After the digestion, proteins were precipitated by 4 volumes of ethanol 24 h at −20° C., prior to separation by SDS-PAGE, blotting and affinodetection by concanavalin A.

In Vitro Galactosylation

The in vitro galactosylation was carried out by treating 50 µg of a total protein extract with 50 mU of β(1,4)galactosyltransferase from bovine milk (Fluka) in 1 mL of 100 mM sodium cacodylate buffer pH 6.4 in presence of 5 µmol of UDP-galactose and 5 µmol of $MnCl_2$ at 37° C. for 24 h (Bardor et al., 2003). The sample was freeze-dried. Then, proteins and glycoproteins were separated by SDS-PAGE and the gel was electro-blotted onto nitrocellulose. Proteins were affinodetected using biotinylated ECA lectin, as described above.

Monosaccharide Composition

Total protein extracts were submitted to a 16 h methanolysis at 80° C. with 500 µL of 1 M methanolic-HCl. After evaporation and additional washing steps with methanol, the samples were re-acetylated by addition in 200 µL of methanol of 20 µL of anhydrous acetic acid and 20 µL of pyridine. The resulting N-acetyl methyl glycosides (methyl ester) were dried and then converted into their trimethylsilyl derivatives and separated by gas chromatography (GC). The gas chromatograph was equipped with a flame ionization detector, a WCOT fused silica capillary column (length 25 m, i.d. 0.25 mm) with CP-Sil 5 CP as stationary phase and helium as gas vector. The oven temperature program was: 2 min at 120° C., 10° C./min to 160° C., and 1.5° C./min to 220° C. and then 20° C./min to 280° C. The quantification of sugar was done by integration of peaks and determination of the corresponding molar values using response factors established with standard monosaccharides. Gas chromatography coupled to electron impact mass spectrometry (GC-EI MS) was carried out using a Hewlett-Packard 6890 series gas chromatography coupled with an Autospec mass spectrometer of EBE geometry (Micromass, Manchester, UK) equipped with a Opus 3.1 data system. Chromatographic separations were obtained using a CP-Sil 5 CB (25 m, 0.25 mm id, 0.25 µm film thickness, Chrompack) silica capillary column coated with polydimethylsiloxane. Helium was the carrier gas and the flow-rate was 0.8 mLmin$^{-1}$. The oven temperature was programmed as follows: initially set at 120° C. for 2 min, raised at a rate of 10° C. min$^{-1}$ to 160° C., then raised at a rate of 1.5° C. min$^{-1}$ to 220° C. and finally raised to 280° C. at a rate of 15° C. min$^{-1}$. The temperatures of the injector, the interface and the lines were 250° C. Injections of 0.5 µL were performed with a split ratio of 5. Electron impact mass spectra were recorded using electron energy of 70 eV, an acceleration voltage of 8 kV and a resolving power of 1,000. The trap current was 200 µA and the magnet scan rate was 1 s/decade over a m/z range 800-4000. The temperature of the ion source was 250° C.

Sialic Acid Analysis

The bound sialic acids from the total protein extracts were released using 2M acetic acid hydrolysis, 3 h at 80° C. (Varki and Diaz, 1984). The released sialic acids were passed through a Microcon® YM-10 (Fisher Scientific) prior to DMB derivatization. The DMB derivatization was done according to Hara et al., 1989. DMB-sialic acid derivatives from the different fractions were then, analysed by high performance liquid chromatography using a C18 column (C18 monomeric S/N E000930-10-2) and the elution conditions as previously reported (Klein et al., 1997). The eluant was monitored by fluorescence. The resulting derivatives were collected, dried down and analyzed by MALDI-TOF MS as described above.

Isolation of N-Linked Glycans

Total proteins were digested by successive treatments with pepsin and PNGase A as previously described in Fitchette et al., 2007. Briefly, 4 mg of proteins were digested with 6 mg of pepsin in 2 mL of 10 mM HCl, pH 2.2, at 37° C. for 48 h. After neutralization with 1 M ammonium hydroxide, the solution was heated for 5 min at 100° C. and lyophilized. Glycopeptides were then deglycosylated overnight at 37° C. with PNGase A (10 mU, Boehringer Mannheim) in a 100 mM sodium acetate buffer, pH 5.0. N-Glycans were purified by successive elution through an AG 50W-X2 column (Bio-RAD) and a C18 cartridge (Varian).

Preparation and Exoglycosidase Digestion of 2-AB Oligosaccharides

Purified N-glycans were labelled by 2-aminobenzamide (2-AB) using the optimized protocol described in Bigge et al., 1995. Briefly, N-glycans were dissolved in 10 µl of 2-AB 0.35 M in dimethylsulfoxide-glacial acetic acid (7:3 v/v) containing sodium cyanoborohydride 1 M. After incubation at 60° C. for 2 hours, the mixture was applied to strip of chromatographic paper (Whatmann 3MM, length, 10 cm; width, 3 cm). Ascending paper chromatography was performed using n-butanol/ethanol/water (4/1/1 v/v/v) at RT for 45 minutes in a glass vessel. After migration, the paper was dried using a hair dryer. Then, labelled N-glycans were detected using a UV light and eluted using water and then lyophilised. For exoglycosidase digestion, 200 milliunits of Jack bean α-mannosidase (Sigma-Aldrich) were desalted by ultrafiltration and incubated overnight at 37° C. with approximately 50 pmoles of 2-AB labelled N-glycan mixture. Then, the digest was directly analysed by matrix assisted laser desorption ionisation-time of flight (MALDI-TOF) mass spectrometry using the conditions described below.

MALDI-TOF Mass Spectrometry Analysis of 2-AB Labelled N-Glycans

MALDI-TOF mass spectra of 2-AB labelled N-glycans were acquired on a Voyager DE-Pro MALDI-TOF instrument (Applied Biosystems, USA) equipped with a 337-nm nitrogen laser. Mass spectra were performed in the reflector delayed extraction mode using 2,5-dihydroxybenzoic acid (Sigma-Aldrich) as matrix. The matrix, freshly dissolved at 5 mg/mL in a 70:30 acetonitrile/0.1% TFA, was mixed with the water solubilized oligosaccharides in a ratio 1:1 (v/v). These spectra were recorded in a positive mode, using an acceleration voltage of 20,000 V with a delay time of 100 ns. They were smoothed once and externally calibrated using commercially available mixtures of peptides and proteins (Applied Biosystems). In this study, the spectra have been externally calibrated using des-Arg$^1$-bradykinin (904.4681 Da), angiotensin I (1296.6853), Glu$^1$-fibrinopeptide B (1570.6774 Da), ACTH$_{18-39}$ (2465.1989 Da) and bovine insulin (5730.6087 Da). Laser shots were accumulated for each spectrum in order to obtain an acceptable signal to noise ratio.

Expression Constructs for EPOm

The cloning vector pPHA-T1 built by Zavlaskaïa et al (2000) includes sequences of *P. tricornuturm* promoters fcpA and fcpB (fucoxanthin-chlorophyll a/c-binding proteins A and B) and the terminator of fcpA. It contains a selection cassette with the gene she ble and a MCS flanking the fcpA promoter. Marine erythropoietin (EPO) is encoded by a 600 bp gene (nucleotide sequence SEQ ID NO: 1). The plasmid pCMV-EPO, provided by B. Pitard, Inserm UMR533 Nantes France, contains the sequence of the EPO gene downstream a cytomegalovirus promoter. The EPO gene was amplified by polymerase chain reaction (PCR) using pCMV-EPO as template and primers FElepo, RFDepo or RH3His6epo, allowing addition of EcoRI and HindIII restriction sites. After digestion by EcoRI and HindIII, the insert was introduced into pPHA-T1 vector.

| | | |
|---|---|---|
| FE1epo | CATgAATTCATggggTgCCCgAAC gTC | SEQ ID N° 2 |
| RH3epo | CATAAgCTTTCACCTgTCCCCTCTC CTg | SEQ ID N° 3 |
| RH3His6epo | CATAAgCTTTCAgTggTggTggTgg TggTgCCTgTCCCCTCTCCTgCAgA | SEQ ID N° 4 |

Expression Constructs for Human PTX3

The cloning vector pPHA-T1 built by Zavlaskaïa and al (2000) includes sequences of *P. tricornutum* promoters fcpA and fcpB (fucoxanthin-chlorophyll a'e-bmding proteins A and B) and the terminator of fcpA. It contains a selection cassette with the gene she ble and a MCS flanking the fcpA promoter. Human Pentraxin 3 (PTX3) is encoded by a 1146 bp gene (nucleotide sequence SEQ ID NO: 5 CCDS3180.1). The plasmid pPTX3 (cDNA) was bought to the RPDZ german company. The PTX3 gene was amplified by polymerase chain reaction (PCR) using pPTX3 as template and the following primers allowing addition of EcoRV and HindIII restriction sites. After digestion by EcoRV and HindIII, the insert was introduced into pPHA-T1 vector.

```
FE5PTX3   CATgATATCATGCATCTCCTTGCGATTCT SEQ ID N° 6
RH3PTX3   CCTAAgCTTTTATgAAACATACTgAgCTCCSEQ ID N° 7
```

Constructs for *P. tricornutum* Transormation: Modifying the N-Glycan Synthesis Pathways:

3 vectors were designed to introduce the human genes of N-glycosylation pathways into *P. tricornutum*.

The squeletton of these vectors is pPHA-T1.

The first vector is pG1. This vector comprises:
the cat gene (chloramphenicol acetyltransferase witch confer chloramphenicol resistance) under the control of the cytomegalovirus promotor (pCMV) and the fcpA terminator: [pCMV-cat-tfcpA]
a Multiple Cloning Site surrounded by the Cauliflower Mosaic virus (p35S) promoter and the fcpA terminator: [p35S-MCS-tfcpA].

The vector pG2 comprises:
the nat gene (Nourseothricin resistance) under control of the cytomegalovirus promotor (pCMV) and the fcpA terminator: [pCMV-nat-tfcpA]
a Multiple Cloning Site surrounded by the Cauliflower Mosaic virus (p35S) promoter and the fcpA terminator: [p35S-MCS-tfcpA].

The third vector, pG3, comprises a Multiple Cloning Site surrounded by the Cauliflower Mosaic virus (p35S) promoter and the fcpA terminator: [p35S-MCS-tfcpA].

The following human genes of glycosylations pathways were inserted in MCS of the vectors pG1, pG2 or pG3:
Human GNTI (SEQ ID NO: 19, Human gene ID: 4245) was inserted into pG1. This vector was then named pG1GNTI.
Human Mannosidase II (SEQ ID NO:38, Human gene ID: 4124) was inserted into PG3. This vector was then called pG3ManII.
Human GNTII (SEQ ID NO: 21, Human gene ID: 4247) was inserted into pG2. This vector was then called pG2GNTII.
Human Alpha 1,6 Fucosyl transferase (SEQ ID NO:40, Human gene ID: 2530) was inserted into pG3. This vector was then called pG3FucTransf.

Constructs for Expression of sh ble in *Tetraselmis suecica* and *Chlorella sorokiniana*

The vector p35SshbleTnos was constructed at the PBA laboratory (IFREMER) using a pUC19 plasmid. It includes the promotor of the cauliflower mosaic virus (p35S), sh ble gene wich confer zeocin resistance and the terminator of the nopalin synthase (Tnos). The vector pUbi1barTnos was constructed at the PBA laboratory (IFREMER) using a pUC19 plasmid. It includes the promotor ubiquitin 1 from maize (Ubi1), bar gene wich confer glufosinate resistance and the terminator of the nopalin synthase (Tnos).

Genetic Transformation

The transformation was carried out by particles bombardment using the BIORAD PDS-1000/He apparatus according to Thomas et al. (2001).

Cultures of microalgae (*P. tricornutum* ccap1052/1A, *Tetraselmis suecica* ccmp904 or *Chlorella sorokiniana*) in exponential growth phase were concentrated by centrifugation (10 minutes, 2150 g, 20° C.), diluted in sterile water (seawater for *P. tricornutum* and *T. suecica*, distilled water for *C. sorokiniana*), and spread on geloses at $10^8$ cells per dish. The microcarriers were gold particles (diameter 0.6 µm). Microcarriers were prepared according to the protocol of the supplier (BIO-RAD). Parameters used for shooting were the following:
use of the long nozzle,
use of the stopping ring with the largest hole,
15 cm between the stopping ring and the target (micralgae cells),
precipitation of the DNA with 1.25 M $CaCl_2$ and 20 mM spermidine,
a ratio of 1.25 µg DNA for 0.75 mg gold particles per shot,
rupture disk of 900 psi with a distance of escape of 0.2 cm for the microalgae *Phaeodactylum tricornutum*, rupture disk of psi with a distance of escape of 0.4 cm for *Tetraselmis suecica*, rupture disk 650 psi and a distance of escape of 0.1 cm for *Chlorella sorokiniana*.
a vacuum of 30 H g, and
four shots per petri dish.

Microalgae were incubated 48 hours before the addition of the antibiotic zeocin (100 µg/ml for *Phaeodactylum tricornutum* or 500 µg/ml for *Tetraselmis suecica* or 200 µg/ml for *Chlorella sorokiniana*) or addition of glufosinate (1 mg/ml) for *Chlorella sorokiniana* and were then maintained at 20° C. (or 28° C. for *Chlorella sorokiniana*) under constant illumination.

Microalgae DNA Extraction $5 \times 10^8$ microalgae cells were pelleted by centrifugation (2150 g, 15 minutes, 4° C.). Microalgae cells were incubated overnight at 4° C. with 4 mL of TE NaCl IX buffer (Tris-HCl 0.1 M, EDTA 0.05 M, NaCl 0.1 M, pH 8), 1% SDS, 1% Sarkosyl and 0.4 $mg.mL^{-1}$ of proteinase K were then added to the sample, followed by a 90 minutes incubation at 40° C. A first phenol-chloroform isoamyl alcohol extraction was carried out to extract an aqueous phase comprising the nucleic acids.

RNA present in the sample was eliminated by an hour incubation at 60° C. in the presence of RNase (1 $µg.mL^{-1}$). A second phenol-chloroform extraction was carried out, followed by a precipitation with ethanol.

Finally, the pellet was dried and solubilised into 200 µl of ultrapure steril water. Quantification of DNA was carried out by spectrophotometry (260 nm) and analysed by electrophoresis.

RNA Extraction $10^7$ cells were pelleted from a culture at exponential phase of growth by centrifugation at 2150 g during 10 min at 4° C., pellet were frozen with liquid nitrogen and RNA extractions were performed with the kit Gen ELute™ Mammalian Total RNA Miniprep Kit (Sigma).

Detection of Recombinant RNA by Reverse Transcription and PCR

RT-PCRs were carried out with Enhanced Avian RT First Strand Synthesis Kit (Sigma) according to the manufacturer's instructions, using polydT primers and the following specific primers.

```
FrtEPO    TCTTAgAggCCAAggAggCAgAAA   SEQ ID N° 8
RrtEPO    ACCCggAAgAgCTTgCAgAAAgTA   SEQ ID N° 9
FrtPTX3   CTAGAGGAGCTGCGGCAGA        SEQ ID N° 10
RrtPTX3   CACCCACCACAAACACTATGGAT    SEQ ID N° 11
```

Preparation of Crude Extract of Microalgae for EPO or PTX3 Detection $10^7$ cells were pelleted from a culture at exponential phase of growth by centrifugation at 2150 g during 10 min at 4° C. After washing with buffer TBS IX, cells were frozen in liquid nitrogen, then resuspended with 1 mL of TBS buffer. The cellular suspension was then sonicated during 30 minutes at 4° C. and centrifuged at 4500 g during 5 minutes at 4° C. Supernatant were finally collected and correspond to crude extracts of microalgae.

In some cases, proteins from crude extracts were precipitated by 90% ammonium sulphate $(NH_4)_2SO_4$ while incubating at 4° C. under agitation during 2 h 30 min. After a centrifugation at 9000 g at 4° C. during 30 min, the solution was suspended in milliQ water and homogenized before being dialysed overnight at 4° C. against water.

Protein concentration of the samples was measured using the "BCA™ Protein Assay Kit" (Pierce) following manufacturer's instructions. The electrophoretic separation of proteins was carried out on a 15% polyacrylamide gel. After SDS-PAGE, immunodetection was carried out with a murine anti-murine EPO antibody, anti-human PTX3 antibody or anti His-tag antibody (R&D systems).

ELISA Assays

Analysis of the protein samples by ELISA (Enzyme-linked ImmunoSorbent Assay) were carried out on crude cellular extracts.

Assays were carried out with the ELISA Quantikine Mouse/Rat EPO Immunoassay Kit (R&D Systems) or with Human Pentraxin 3/TSG-14 Quantikine ELISA Kit (R&D Systems), according to manufacturer's instructions.

His-Tagged Recombinant Protein Purification 1 ml of resin (Ni-NTA beads, Hi-Trap chelating HP Amersham Biosciences) is mixed in an aqueous solution containing 0.1M imidazole during 2 hours at room temperature and under agitation. Lyophilized protein samples are mixed in a small volume of buffer (Tris pH 7.6, 30 mM, glycerol 20%, 50 mM NaCl, 1 mM PMSF, 1 mM β-mercaptoethanol) containing 0.1 M imidazole. Resin and samples are then mixed and incubated 2 h at 4° C. under agitation. After 10 min of centrifugation (4000 g at 4° C.), the supernatant is thrown away and 20 ml of washing buffer (20 mM $Na_2HPO_4$, 20% glycerol, 0.5 M NaCl, 1 mM PMSF, 1 mM β-mercaptoethanol, containing 0.250 M imidazole) is added. After gentle mix and centrifugation (10 min at 4000 g 4° C.), the pellet is resuspended in 3 ml of elution buffer (20 mM $Na_2HPO_4$, 20% glycerol, 0.5 M NaCl, 1 mM PMSF, 1 mM β-mercaptoethanol) containing 1 M imidazole. The sample is then incubated under agitation during 2 hours at 4° C. After 10 min of centrifugation (4000 g at 4° C.), supernatant is collected and imidazole is then eliminated from the samples using 3 kDa centricon columns (Millipore) according to manufacturer's instructions.

EPO Bioassay

Bioassay of the recombinant EPO produced in *Phaeodactylum tricornutum* was carried out using the human erythroleukemia cell line TF-1 purchased from ATCC. When cultured with EPO, TF-1 cells differentiate by producing hemoglobin.

Cells were cultured (37° C., 5% $CO_2$) in RPMI 1640 supplemented with 10% fetal bovine serum, 2 mM L-glutamine, 100 units/mL penicillin, 100 µg/mL streptomycin and 5 ng/mL granulocyte-macrophage colony-stimulating factor (GM-CSF). 24 h prior to the EPO bioassay, GM-CSF was removed from cell culture media. Cells were then incubated for 3 days with 0.1-10 ng/mL recombinant mouse EPO (positive control) or 0.1-10 ng/mL of *Phaeodactylum tricornutum* recombinant murine EPO (based on ELISA quantification). Cells were also incubated with a similar volume of non-transformant *Phaeodactylum tricornutum* extract as a negative control (*Phaeodactylum tricornutum* transformed by the plasmid pPHA-T1).

On day 3, differenciated cells producing hemoglobin were stained using benzidine method described in Matsubara et al. (*J. Biol. Chem.*, vol. 284(6), p:3480-3487, 2009). Cells with blue-brown-staining cytoplasm were counted as hemoglobinized cells. Cell viability was also assessed using trypan blue. 200 cells were counted in each analysis and experiments were repeated three times.

Results were expressed as a percentage of differenciated and viable cells (+/− SEM).

Results

In Silico Analysis of the *Phaeodactylum tricornutum* Genome

The N-glycan biosynthetic pathway can be divided into three steps in eukaryotes: 1—the synthesis of the dolichol pyrophosphate-linked oligosaccharide donor $Glc_3Man_9GlcNAc_2$-PP-Dol and its transfer by the oligosaccharyltransferase (OST) onto asparagine residues of nascent polypeptides entering the lumen of the rough endoplasmic reticulum, 2—the deglucosylation/reglucosylation of the precursor N-glycan in the endoplasmic reticulum (ER) allowing the interaction with chaperones responsible for proper folding and oligomerization and finally 3—the maturation in the Golgi apparatus into high-mannose-type N-linked oligosaccharides and then complex-type N-glycans. Based on sequence homologies with genes encoding these differents steps in eukaryotic organisms, we identified in the genome of *Phaeodactylum tricornutum* a set of putative sequences for the steps of the N-glycan biosynthesis and maturation into high-mannose-type N-glycans (see FIG. 1 and table 2). Most of these identified genes have EST support (FIG. 1, Table 2).

TABLE 2

References and characteristics of putative proteins involved in the N-glycan biosynthesis in *P. tricornutum*

| N°[1] | Protein[2] | Protein lenght | EST P.t.1.8.6[3] | P.t.3[4] | Signal peptide | TMD[5] | Pfam |
|---|---|---|---|---|---|---|---|
| Synthesis of the dolichol phosphate precursor | | | | | | | |
| 9724 | GlcNAcT | 372 | Yes | No | Yes | 7 | PF00953 |
| 9427 | β(1,4)-GlcNAcT | 123 | No | No | Yes | 0 | PF04101 |
| 14444 | β(1,4)-GlcNAcT | 181 | No | No | No | 2 | PF00249 |
| 14002 | β(1,4)-ManT | 398 | Yes | Yes | Yes | 2 | PF00534 |
| 48588 | α(1,3)-ManT | 518 | Yes | No | Yes | 1 | PF00534 |
| 44447 | α(1,3)-ManT | 440 | Yes | Yes | Yes | 9 | PF05208 |
| 44425 | α(1,2)-ManT | 581 | Yes | No | Yes | 6 | PF03901 |
| 44574 | α(1,2)-ManT | 557 | Yes | No | No | 10 | PF03901 |
| 44905 | α(1,3)-GlcT | 437 | No | Yes | No | 7 | PF03155 |

TABLE 2-continued

References and characteristics of putative proteins involved in the
N-glycan biosynthesis in *P. tricornutum*

| N°[1] | Protein[2] | Protein lenght | EST P.t.1.8.6[3] | P.t.3[4] | Signal peptide | TMD[5] | Pfam |
|---|---|---|---|---|---|---|---|
| 44117 | α(1,3)-GlcT | 533 | No | Yes | Yes | 10 | PF03155 |
| 19705 | P-Dol ManT | 237 | Yes | No | Yes | 0 | PF00535 |
| 34317 | P-Dol GlcT | 321 | No | No | No | 0 | PF00535 |
| | | Transfert of the precursor | | | | | |
| 55197 | STT3 | 911 | Yes | Yes | No | 9 | PF02516 |
| 55198 | STT3 | 894 | Yes | Yes | Yes | 10 | PF02516 |
| | | Quality control in the ER | | | | | |
| 50836 | α-GlcII α-subunit | 712 | Yes | Yes | No | 0 | PF01055 |
| 54169 | α-GlcII β-subunit | 802 | Yes | No | Yes | 0 | PF07915 |
| 50260 | calreticulin | 410 | Yes | Yes | Yes | 0 | PF00262 |
| 38004 | UGGT | 1653 | Yes | Yes | No | 0 | PF06427 |
| | | Golgi maturation | | | | | |
| 52346 | α-Man I | 509 | No | No | No | 0 | PF01532 |

[1]Sequence number in the *Phaeodactylum tricornutum* genome
[2]Putative biological function of the protein encoded by the gene
[3]ESTs from *Phaeodactylum tricornutum* P.t.1.8.6 strain grown in standard conditions
[4]ESTs from *Phaeodactylum tricornutum* P.t.3 strain grown in standard conditions
[5]Transmembrane domains Biosynthesis and Transfer of the Dolichol Pyrophosphate-Linked Oligosaccharide All enzymes involved in the biosynthesis of dolichol pyrophosphate-linked oligosaccharide on the cytosolic face and in the lumen of the ER were identified in the genome of *Phaeociactylum tricornutum*. Theses sequences and topologies of predicted proteins share strong homologies with the corresponding asparagine-linked glycosylation (alg) homologs described in other eukaryotes. Putative transferases able to catalyse the formation of dolichol-activated mannose and glucose are also predicted. Those two activated sugars are required for the elongation steps arising in the ER lumen. In addition to sequences involved in the biosynthesis of the dolichol pyrophosphate-linked oligosaccharide, two putative genes homologous to the STT3 catalytic subunit of the oligosaccharyltransferase (OST) multisubtmit complex were identified in the *P. tricornutum* genome (Table 2). These multi spanned sequences, having respectively 34% and 37% identity with *Arabidopsis thaliana* and *Homo sapiens* STT3 subunits, contain the conserved WWDYG domain required for the transfer of the precursor onto asn residues.

Quality Control of the Protein in the ER

Only putative sequences encoding the α and β subunits of α-glucosidase II were found in the *P. tricornutum* genome. The α and β subunits harbour the characteristic DMNE sequence and a C-type lectin domain involved in mannose binding. A putative UDP-glucose:glycoprotein glucosyltransferase (UGGT) and a calreticulin, two molecules ensuring the quality control of proteins in the ER, are also predicted. Calreticulin is a soluble protein which is a major $Ca^{2+}$ binding protein of the ER lumen which is involved in the retention of incorrectly or incompletely folded proteins. *P. tricornutum* calreticulin is similar in size to the known calreticulins (about 400 amino acids) and exhibit more than 50% identities to respective proteins from *Nicotiana plumbaginifolia* (56%), *Chlamydomonas reinhardtii* (56%), *Ricinus communis* (54%) and *Arahidopsis thaliana* (53%) Structurally, the *P. tricornutum* calreticulin contains the three specific domains required for its biological function: an N-terminal domain of about 180 amino acids, a central domain of about 70 residues which contains three repeats of an acidic 17 amino acid motifs responsible for the $Ca^{2+}$ binding with a low-capacity and a high affinity and a C-terminal domain rich in acidic and lysine residues which can bind $Ca^{2+}$ with a high-capacity but a low affinity. *P. tricorniitum* calreticulin also harbours a predicted signal peptide and a C-terminal YDEF tetrapeptide that could ensure its retention in the ER.

Maturation of N-Linked Glycans in the Golgi Apparatus

One sequence encoding a putative Golgi α(1,2)-mannosidase I was identified in the genome (Table 2). This glycosidase is able to convert $Man_9GlcNAc_2$ into $Man_5GlcNAc_2$.

Sugar Composition and Western-Blot Analysis of *P. tricornutum* Proteins

Sugar composition of *P. tricornutum* proteins isolated from the fusiform Pt 1.8.6 strain was determined to investigate the presence of monosaccharides specific for N-glycans. Proteins were hydrolysed and the resulting monosaccharides were converted into 1-O-methyl persilyl derivatives and analysed by gas chromatography coupled to electron impact mass spectrometry (GC-EI MS). As presented in Table 3, mannose and N-acetylglucosamine, two monomers constitutive of N-linked glycans, were identified in *P. tricornutum* protein extract. Other monosaccharides, such as rhamnose, xylose, fucose, glucose and galactose, were identified. However, it cannot be concluded whether these monomers arise from protein linked glycans or from contaminating polysaccharides. In contrast, neither N-acelylneuraminic acid nor its precursor N-acetylmannosamine were detected. To ensure the absence of a sialylation pathway in *P. tricornutum* proteins, *P. tricornutum* proteins were submitted to a mild acid hydrolysis. The hydrolysate was coupled to 1,2 diamino-4,5-methylene dioxybenzene (DMB) and the resulting derivatives were analysed by liquid chromatography as previously reported. Peaks detected by fluorescence were collected and analyzed by matrix-assisted laser desorption ionization-time of flight mass spectrometry (MALDI-TOF MS). No sialic acids were identified confirming the absence in this diatom of detectable a sialylation pathway (not shown).

TABLE 3

Sugar composition of *P. tricornutum* proteins

| Monosaccharide | mole %[1] |
|---|---|
| Arabinose | 0.2 +/− 0.2 |
| Rhamnose | 29.3 +/− 1.6 |
| Fucose | 5.3 +/− 1.0 |
| Xylose | 18.6 +/− 2.0 |
| Mannose | 16.7 +/− 8.4 |
| Galactose | 20.6 +/− 2.5 |
| GalNAc | 5.1 +/− 2.9 |
| GlcNAc | 6.2 +/− 3.1 |
| ManNAc | n.d.[2] |
| Neu5Ac | n.d.[2] |

[1]Relative ratio between monomers
[2]Not detected

Figure 2:
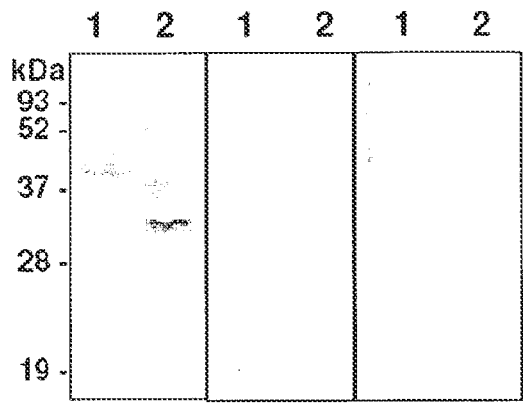
FIG. 2. *Phaeodactylum tricornutum* glycoproteins harbour N-linked oligosaccharides recognized by concanavalin A
(a) Affinodetection using concanavalin A and immunodetection using antibodies raised against the core β1,2-xylose and core α1,3-fucose epitopes of proteins isolated from green oignon (Lane 1) and from *P. tricornutum* P.t.1.8.6 fusiform strain (Lane 2).
(b) Affinodetection by concanavalin A of a protein extract isolated from *P. tricornutum* Pt 1.8.6 fusiform strain, treated or not by endoglycosidase H (Endo H) and peptide N-glycosidase F (PNGase F).
Figure 2:
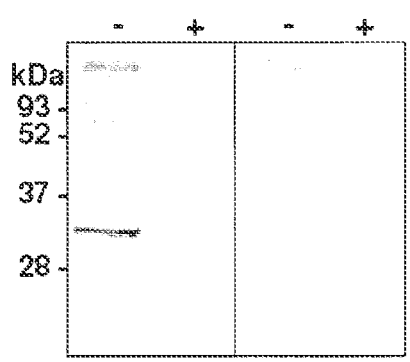

Structural analysis of glycans N-linked to *P. tricornutum* proteins was then investigated by western-blot analysis on a total protein extract using probes specific for glycan epitopes. As illustrated in FIG. 2a, *P. tricornuturm* proteins are affinodetected by concanavalin A, a lectin specific for high-mannose sequences. This affinodetection is suppressed upon treatment with Endo H or PNGase F, two enzymes able to cleave N-glycans, thus confirming that this lectin recognized glycan sequences N-linked to *P. tricornutum* proteins (FIG. 2b). In contrast, affinodetection with ECA and PHA, two lectins specific for complex N-linked glycan epitopes, were negative (not shown). Immunodetections using antibodies raised against plant glycoepitopes were then carried out. Antibodies specific for core-α(1,3)-fucose or core β(1,2) -xylose epitopes linked to the $Man_3GlcNAc_2$ common core did not detect any protein from *P. tricornutum* (FIG. 2a). Complex-type N-glycans result from the addition of a terminal GlcNAc onto $MaHsGlcNAc_2$ by action of GnT I and then maturation of this oligosaccharide. In order to investigate the presence in *P. tricornutum* proteins of complex glycans, we treated a protein extract with a galactosyltransferase, an enzyme able to transfer a galactose residue onto terminal GlcNAc units, and then analyzed the resulting protein preparation with ECA, a lectin that binds to Galβ1-4 GlcNAc sequences. No signal was detected after this treatment, thus indicating that *P. tricornutum* proteins does not exhibit terminal GlcNAc in a detectable manner.

Structural Identification of *P. tricornutum* N-Linked Glycans

Figure 3:
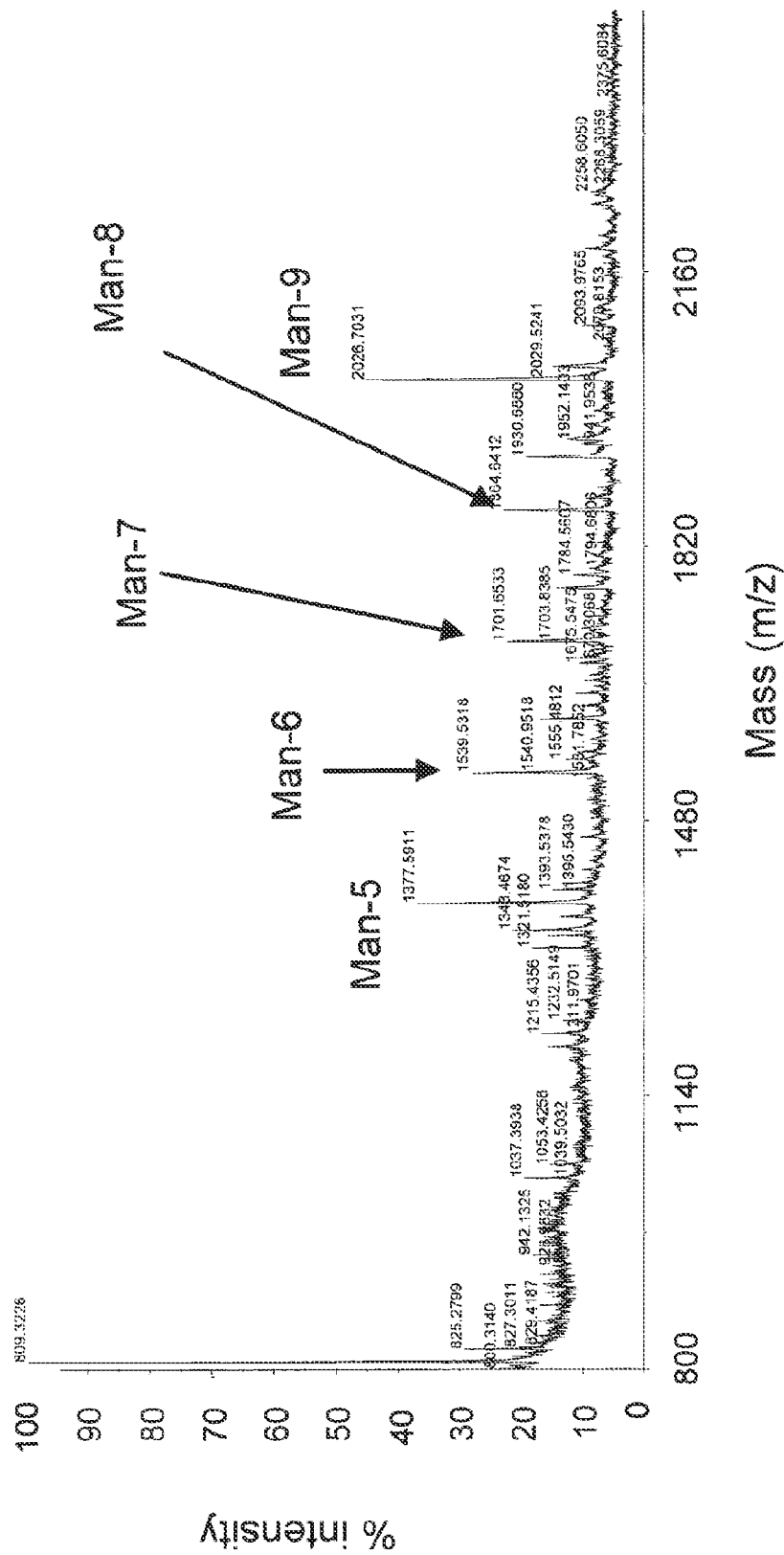
FIG. 3. N-linked glycans from *Phaeodactylum tricornutum* are high mannose type structures. MALDI-TOF MS of N-linked glycans released from glycoproteins isolated from *P. tricornutum* Pt 1.8.6 strain grown in standard conditions and labelled with 2-aminobenzamide.

N-glycans were released from *P. tricornutum* proteins isolated from the Pt 1.8.6 strain by PNGase A treatment as previously reported for proteins isolated from plants. PNGase A was preferred to PNGase F since this deglycosylating enzyme is able to release a large variety of N-linked oligosaccharides, including glycans harboring a fucose α(1,3)-linked to the proximal glucosamine residue. The resulting N-glycans were then coupled to 2-aminobenzamide (2-AB) to facilitate their detection and the analysis by mass spectrometry. MALDI-TOF MS of the resulting pool of labeled N-glycans is shown in FIG. 3. Major ions corresponded to $(M+Na)^+$ ions of 2-AB derivatives of $Hexose_{5-9}GlcNAc_2$. The pool of glycans was then submitted to an exoglycosidase digestion. Consistent with the presence of α-linked mannose residues, the oligosaccharides mixture was converted to $Hexose_2GlcNAc_2$ to $Hexose_4GlcNAc_2$ upon treatment with Jack bean α-mannosidase (not shown). As a consequence, ions detected in MALDI-TOF MS were assigned to high-mannose N-glycans ranging from $Man_9GlcNAc_2$ to $Man_5GlcNAc_2$ previously reported in other eukaryotes. Taken together, biochemical analysis of N-linked glycans from *P. tricornutum* demonstrated that proteins from this organism harbour high-mannose-type N-glycans ranging from $Man_9GlcNAc_2$ to $Man_5GlcNAc_2$. This analysis did not reveal the presence of plant N-glycan epitopes, i.e. core-α(1,3)-fucose or core β(1,2)-xylose epitopes linked to the common core. These epitopes are known to be highly immunogenic in human and requires the development of the knock-out strategy of the corresponding genes before any use of plant-derived proteins in human therapy.

Figure 4:
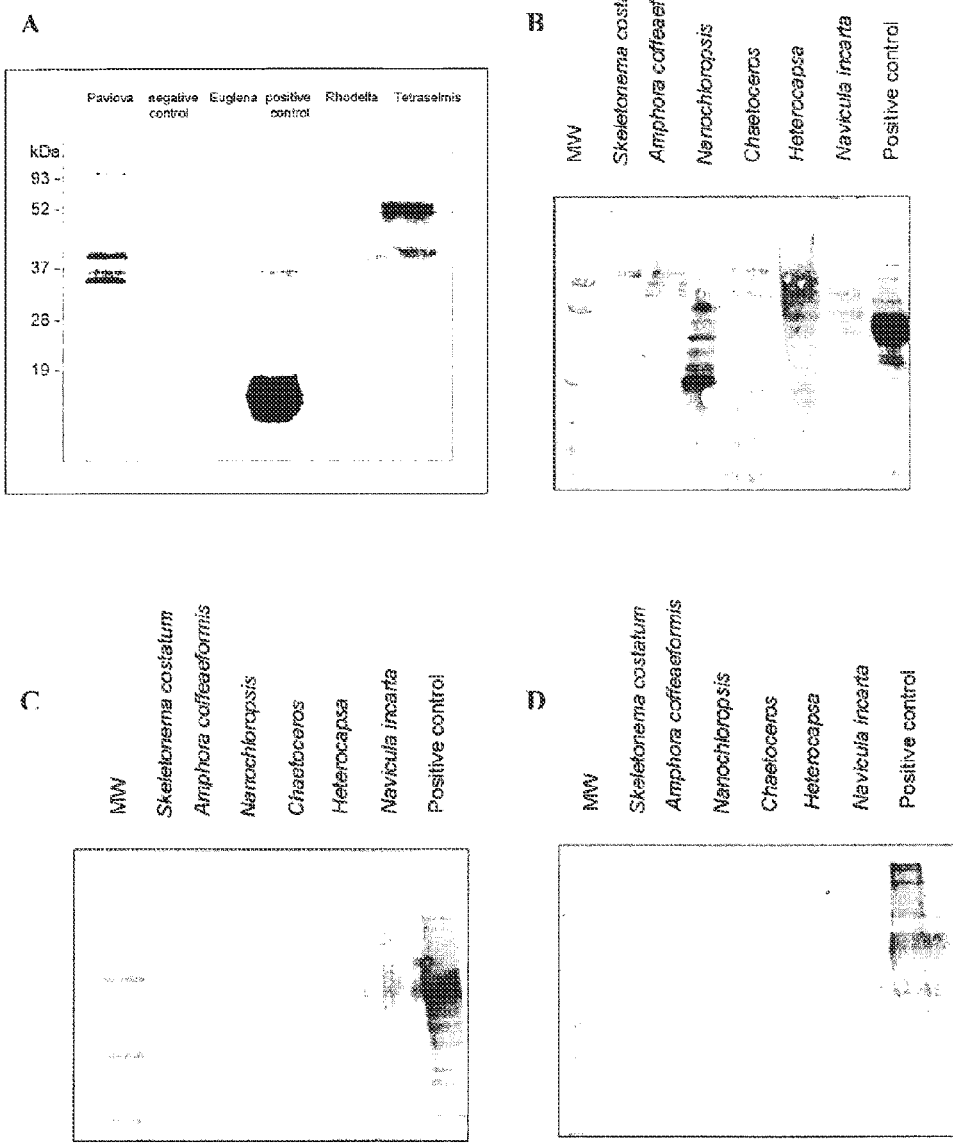
FIG. 4. N-linked glycans from representative microalgae are high mannose type structures.
A. Affinodetection of high mannose N-glycans by concanavalin A of proteins from *Euglena, Tetraselmis, Pavlova, Rhodella*.
B. Affinodetection of high mannose N-glycans by concanavalin A of proteins from *Skeuletonema, Heterocapsa, Amphora, Chaetoceros, Naviculas, Nanochloropsis*.
C. Affinodetection by anti α-1,3 Fucose antibody of proteins from *Skeuletonema, Heterocapsa, Amphora, Chaetoceros, Naviculas, Nanochloropsis*
D. Affinodetection by anti β-1,2 Xylose antibody of proteins from *Skeuletonema, Heterocapsa, Amphora, Chaetoceros, Naviculas, Nanochloropsis*

N-Glycosylation Analysis of Proteins from Representative Microalgae of Main Phylum The N-glycosylation of proteins isolated from microalgae representative of main phylum was analysed by western-blot using glycan-specific probes (FIG. 4). Proteins from *Tetraselmis, Rhodella, Euglena* and *Pavlova* (FIG. 4A), from *Skeuletonema, Heterocapsa, Amphora, Chaetoceros, Naviculas, Nanochloropsis* (FIG. 4B, C, D) and from *Chlorella, Nanochloropsis salina, Chlorella sorokiniana, Isochrysis galbana, Chaetoceros calcitrans, Nitzschia punctata, Thalassiosira pseudonana, Heterocapsa triquetra, Porphyridium cruentum* (data not shown) were demonstrated to be affinodetected by concanavalin A but not by other probes such as antibodies raised against α(1,3)-fucose and β(1,2)-xylose epitopes, specific for plant complex N-glycans. The affinodetection disappeared after Endo H treatment thus confirming that the concanacalin A positive signals arose from N-linked glycans. As a consequence, as observed in *P. tricornutum*, we concluded that the representative microalgae tested:

- green algae: *Tetraselmis* (Prasinophytes), *Nanochloropsis* (e.g., *Nanochloropsis salina*) and *Chlorella* (Chlorophytes; e.g., *Chlorella sorokiniana*),
- red algae: *Rhodella* and *Porphyridium cruentum* (Rhodophytina),
- chromalveolates: *Pavlova* (Chrysophytes), *Skeuletonema, Amphora, Chaetoceros* (e.g., *Chaetoceros calcitrans*), *Nitzschia punctata, Thalassiosira pseudonana, Naviculas* (Diatoms), *Isochrysis galbana* (Haptophytes), *Heterocapsa triquetra* (Dinoflagellates)
- euglenids: *Euglena*, in this study harbour high-mannose type N-glycans on their proteins and do not harbour α(1,3)-fucose and β(1,2)-xylose epitopes.

Expression of Recombinant Murine EPO in *P. tricornutum*

Figure 5:
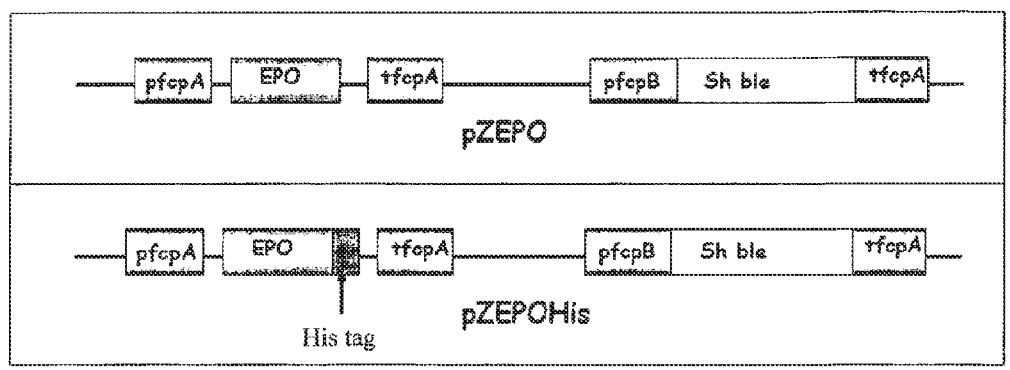
FIG. 5. pZEPO and pZEPOHis constructs.

*P. tricornutum* strain CCAP 1052/1A was transformed by particle bombardment with the plasmids pZEPO or pZEPO-His (FIG. 5). Among transformants resistant to zeocine, 80 clones (for each construct) were tested for the presence of the gene of interest, EPO. The presence of the EPO gene was checked by PCR with the following primers: a couple of primers specific of the transgene, and a couple of primers FpZ and RpZ hybridizing upstream and downstream of the transgene within the vector pPHA-T1.

```
Fepo    ATggggTgCCCgAACgTC          SEQ ID N° 12

Repo    TCACCTgTCCCCTCTCCTg         SEQ ID N° 13

FpZ     TCAgTTCTgCACAAATTTgTCTgCCg  SEQ ID N° 14

RpZ     CACgTCCCTggTTgAgTTCgATAgCA  SEQ ID N° 15
```

Figure 6:
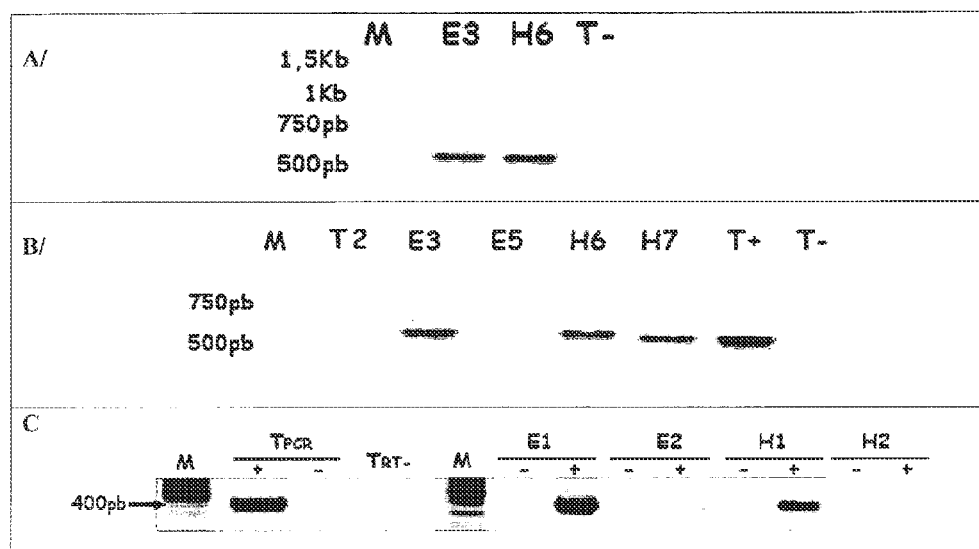
FIG. 6. recombinant EPO DNA and transcripts analysis by PCR (A) and RT-PCR (B).
Figure 7:
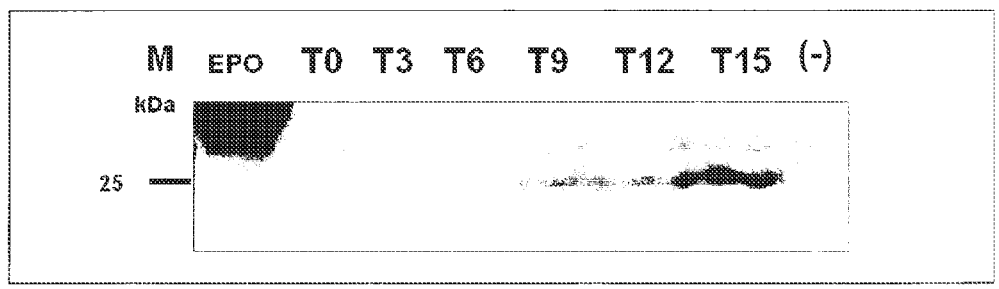
FIG. 7. recombinant EPO protein analysis by western-blot.
Figure 8:
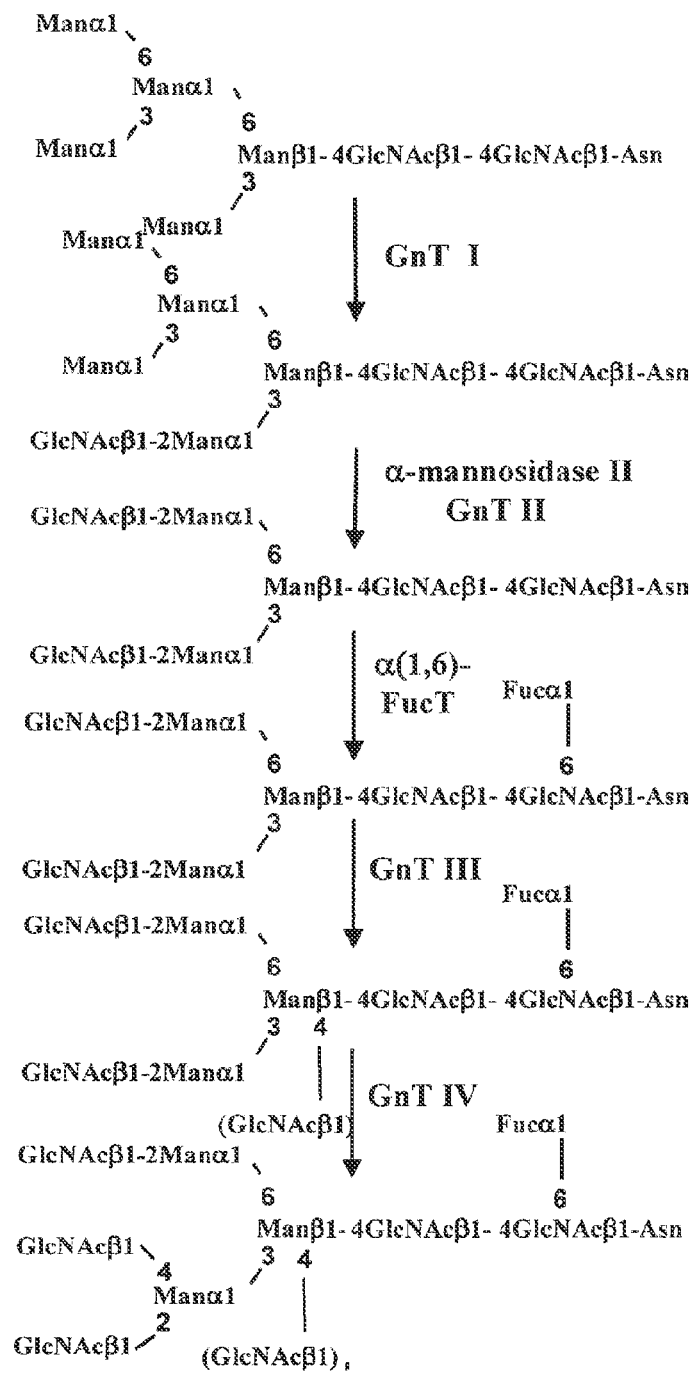
FIG. 8. humanised N-glycosylation pathway
Figure 8:
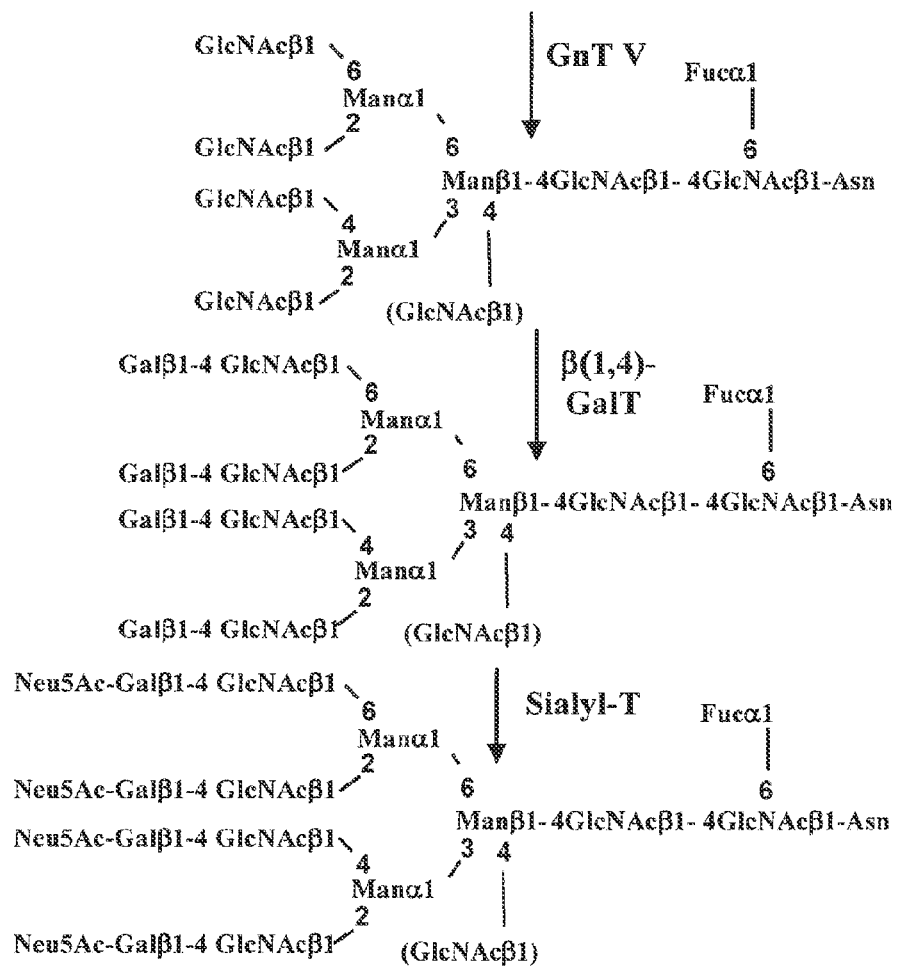

Clones of *P. tricormitum* transformed by pZEPO were named E1 to E80 and those resulting from transformations by pZEPOHis were called H1 to H80. In FIG. 6A, amplifications were carried out with the primers FpZ and RpZ hybridizing respectively on the 5' end of the fcpA promoter and the 3' of terminating the fcpA, allowing the amplification of transgene inserted in the MCS of pPHA-T1. Samples E3 and H6 present an amplification of approximately 600 bp corresponding to the size of the EPO transgene. FIG. 6 B shows products of PCR carried out with specific primers of EPO. The positive control of PCR (realized on the vector pZEPO) presents a band of amplification at approximately 600 bp. Samples E3, E5, H6, H7 present an amplification of approximately 600 bp corresponding to the size of the EPO. Among all zeocine-resistant clones of *P. tricormitum*, approximately 90% integrated EPO transgene in their genome.

Transgene expression at RNA level was also analysed. FIG. 6 C shows that samples E1, E2, H1 and H2 present an amplification of approximately 385 pb corresponding to EPO transcripts.

Among all zeocine-resistant clones of *P. tricormitum*, approximately 76% expressed EPO transcripts.

The presence of EPO protein was then analysed.

The presence of recombinant murine EPO was tested on crude extracts by ELISA assays.

Recombinant murine EPO was detected in 60% of the tested clones.

To enhance the quantity of EPO protein in the cells, an induction of fcpA promoter was carried out. The microalgae were incubated 36 hours in the dark and then placed in the light (T0). Samples were harvested at T3, T6, T9, T12 and T15 hours and loaded onto SDS-PAGE. Analysis by immunodetection with an anti-EPO antibody showed that the EPO recombinant protein is produced in microalgae cells (FIG. 7).

As non glycosylated EPO protein molecular weight is about 18 kDa, recombinant EPO detected by western-blot exhibits an electrophoretic migration (about 25 kDa) consistent with the presence of glycan structures (FIG. 7). The recombinant EPO produced in CHO cells (column EPO on FIG. 7) exhibits an electrophoretic migration of about 30.1 kDa due to the presence of complex glycans.

Since we demonstrated that *Phaeodactylum* cells introduced Man5 to Man9 on its proteins, we postulate that such glycan structures are attached to recombinant EPO and responsible for the decrease electrophoretic mobility observed on SDS-PAGE.

To verify this hypothesis, we digest the recombinant EPO by the PNGase F that specifically cleave the N-glycans lacking alpha-(1,3)-linked core fucose. We load on SDS-PAGE samples and recombinant murine EPO produced in CHO, before and after PNGase F digestion. After immunodetection with anti-EPO antibodies, we are able to compare the electrophoretic profiles. All digested samples are around 18-19 kDa, consistent with the effective digestion of N-glycosylations giving an about non-glycosylated-18 kDa protein. This experimentation shows that some N-glycosylation is present on the recombinant murine EPO produced by *Phaeodactylum tricornutum* and confirms that said EPO does not contain alpha-(1,3)-linked core fucose.

To further caracterise the N-glycan structures, we are analysing N-glycosylation profiles of this recombinant murine EPO produced by *Phaeodactylum tricornutum* by Mass Spectrometry. Activity assays on the recombinant EPO are being carried out.

EPO Bioassay

Preliminary results from the ongoing experiment revealed the production of hemoglobin when TF-1 cells were incubated with murine EPO from *Phaeodactyltun tricornutum* carrying the plasmid pZEPO compared to cells incubated with extract from *P. Tricornutum* carrying the pPHA-T1 plasmid. Cell viability remained similar throughout the experiment. These results revealed that the recombinant murine EPO produced from *Phaeodactylum tricornutum* retained its biological activity measured as the ability to induce TF-1 cells differentiation.

EPO Immunogenicity

The activity and immunogenicity of EPO produced in *P. tricornutum* is assayed in vivo in mice: after injection of recombinant EPO, the quantity of erythrocytes is analysed for determining EPO activity. Moreover, the immune response is analysed so as to determine that said recombinant EPO does not present any incompatibility with a therapeutic usage.

Transformation of *P. tricornutum* N-glycosylation Pathways:

Two strains of *P. tricornutum* were transformed with several human genes: the wild type and recombinant algae expressing mouse EPO.

These microalgae were transformed in two times.

First, *Phaeodactylum tricornutum* cells were cotransformed by two vectors: pG1GNTI wich confer resistance to chloramphenicol (and with human GNTI gene) and with vector pG3ManII (with human mannosidase II gene). After selection of the transformants with chloralphenicol, glycosylations pathways of algaes were analysed: recombinant EPO was purified and N-glycosylation was analysed by mass spectrometry. The alges presenting an activity of GNTI and ManII were isolated and co-transformed again but with: pG2GNTII wich confer Nourseothricin resistance (with human GNTII gene) and with vector pG3Fuctransf (with human Alpha 1,6 Fucosyl transferase). Transformed microalgae were selected on nourseothricin, and N-glycosylation of recombinant EPO was analysed by Mass spectrometry.

We are currently finishing these experimentations before introducing other genes to go further in the "humanization" of N-glycans of *P. tricornutum.*

Recombinant Human PTX3 Expression in *P. tricornutum:*

*P. tricornutum* strain CCAP 1052/1A was transformed by particle bombardment with the plasmid pZPTX3. Among transformants resistant to zeocine, 50 clones were tested for the presence of the gene of interest, PTX3.

The presence of the PTX3 gene was checked by PCR with the following primers: a couple of primers specific of the transgene, and a couple of primers FpZ and RpZ hybridizing upstream and downstream of the transgene within the vector pPHA-T1.

| | | |
|---|---|---|
| FpZ | TCAgTTCTgCACAAATTTgTCTgCCg | SEQ ID N° 14 |
| RpZ | CACgTCCCTggTTgAgTTCgATAgCA | SEQ ID N° 15 |
| FPTX3 | ATGCATCTCCTTGCGATTCT | SEQ ID N° 16 |
| RPTX3 | TGA AAC ATA CTG AGC TCC TC | SEQ ID N° 17 |

Among all zeocine-resistant clones of *P. tricornutum*, approximately 90% integrated PTX3 transgene in their genome.

Analysis of the presence of PTX3 transcripts and protein in zeocine-resistant clones of *P. tricornutum* is currently under investigation.

Transformation of the Prasinophyte *Tetraselmis suecica:*

*Tetraselmis suecica* ccmp904 were transformed by particle bombardment with the construct p35SshbleNos. We obtained clones resistant to zeocine, indicating that Sh ble protein is expressed in the microalgae. Despite the fact that Sh ble is not a glycosylated protein, this experimentation shows the feasibility of producing recombinant proteins in *Tetraselmis suecica*. As *Tetraselmis suecica* is able to N-glycosylate endogenous proteins (see page 45), we can assume that a polypeptide presenting N-glycosylation sites, when expressed in this microalgae, will present N-glycans structures.

Transformation of the Chlorophyte *Chlorella sorokiniana*:

Chlorella sorokiniana UTEX 1330 were transformed by particle bombardment with the constructs p35SshbleTnos and pUbi1barTNos. We obtained clones resistant to zeocine, indicating that Sh ble protein is expressed in the microalgae, and clones resistant to glufosinate indicating that bar gene is expressed in the microalgae. This highlights the fact that we have tools to transform the Chlorophyte *Chlorella sorokiniana*, especially vectors with functional promoters.

Despite the fact that Sh ble is not a glycosylated protein, this experimentation shows the feasibility of producing recombinant proteins in *Chlorella sorokiniana*. As this algae is able to N-glycosylate endogenous proteins (data not shown), we can assume that a polypeptide presenting N-glycosylation sites, when expressed in this microalgae, will present N-glycans structures.

The invention claimed is:

1. A method for producing at least one glycosylated polypeptide, comprising the steps of:
    (i) culturing a transformed microalgae so as to obtain the expression of said at least one glycosylated polypeptide;
    (ii) purifying glycosylated polypeptides from the cultured microalgae;
    (iii) determining the glycosylation pattern of the glycosylated polypeptides; and
    (iv) selecting said at least one glycosylated polypeptide having at least one $Man_9GlcNAc_2$ to $Man_5GlcNAc_2$ structure and not comprising β(1,2)-linked xylose, wherein,
    said transformed microalgae comprises a nucleotide sequence encoding said at least one glycosylated polypeptide operably linked to a promoter that drives expression of said nucleotide sequence in said microalgae, and
    the transformed microalgae do not have suppressed expression of β(1,2)-xylosyltransferase.

2. The method according to claim 1, wherein said microalgae is selected from the group consisting of green algae, red algae, chromalveolates, and euglenids.

3. The method according to claim 1, wherein said microalgae is selected from the group consisting of Chlorophytes, Euglenids, Haptophytes, Prasinophytes, and Diatoms.

4. The method according to claim 1, wherein said microalgae is one of Haptophytes or Diatoms.

5. The method according to claim 1, wherein the glycosylated polypeptide is selected from the group consisting of a polypeptide having a primary amino acid sequence of a human glycosylated polypeptide, a primary amino acid sequence of a non-human glycosylated polypeptide, a primary amino acid sequence of an antibody or an active fragment thereof, a primary amino acid sequence of a non-mammalian glycosylated polypeptide, and combinations thereof.

6. The method according to claim 1, wherein said glycosylated polypeptide is selected from the group consisting of erythropoietin, a cytokine, an antibody, a coagulation factor, a hormone, beta-glucocerebrosidase, pentraxin-3, and an anti-TNF.

7. The method according to claim 1, wherein the transformed microalgae do not have suppressed expression of α(1,3)-fucosyltransferase.

8. The method according to claim 1, wherein said microalgae is one of Chlorophytes or Prasinophytes.

9. The method according to claim 1, wherein said microalgae is a Euglenid.

10. The method according to claim 1, wherein said microalgae is *Phaeodactylum tricornutum*.

* * * * *